United States Patent [19]
McEvoy et al.

[11] Patent Number: 5,844,961
[45] Date of Patent: Dec. 1, 1998

[54] FILMLESS DIGITAL X-RAY SYSTEM

[75] Inventors: Steven P. McEvoy, San Carlos; Emilian S. Ochotta, Campbell; Kent R. Richardson, Mountain View; David C. Hatcher, Sacramento; Raymond T. Mah, Santa Clara, all of Calif.

[73] Assignee: MedFX Systems, San Carlos, Calif.

[21] Appl. No.: 690,471

[22] Filed: Jul. 26, 1996

Related U.S. Application Data

[60] Provisional application No. 60/001,531 Jul. 26, 1995.
[51] Int. Cl.$^6$ ...................................................... H05G 1/42
[52] U.S. Cl. ........................... 378/98.8; 378/191; 378/189
[58] Field of Search ............................... 378/38–40, 98.8, 378/98.2, 98.3, 169, 176, 182, 183, 186, 188, 189, 191

[56] References Cited

U.S. PATENT DOCUMENTS

| | | | |
|---|---|---|---|
| 4,188,537 | 2/1980 | Franke | 250/416 TV |
| 4,823,369 | 4/1989 | Guenther et al. | 378/22 |
| 4,878,234 | 10/1989 | Pfeiffer et al. | 378/40 |
| 5,434,418 | 7/1995 | Schick | 378/98.8 |
| 5,440,130 | 8/1995 | Cox et al. | 378/98.8 |
| 5,454,022 | 9/1995 | Lee et al. | 378/98.8 |
| 5,579,361 | 11/1996 | Augais et al. | 378/98.8 |

*Primary Examiner*—Don Wong
*Attorney, Agent, or Firm*—Wilson Sonsini Goodrich & Rosati

[57] ABSTRACT

A filmless digital x-ray cassette comprising the following. A standard sized x-ray cassette housing having external dimensions approximately equal to the external dimensions of a standard x-ray cassette. An array system having a plurality of light sensitive pixels, the array system being disposed at least partially within the standard sized x-ray cassette housing. An electronics system, coupled in communications with the array system, the electronics system converting pixel values received from the array system into a digital image. A communications circuit, coupled to the electronics system, having a digital image output.

19 Claims, 39 Drawing Sheets

FIGURE 4 — EXPLODED VIEW OF DIGITAL CASSETTE

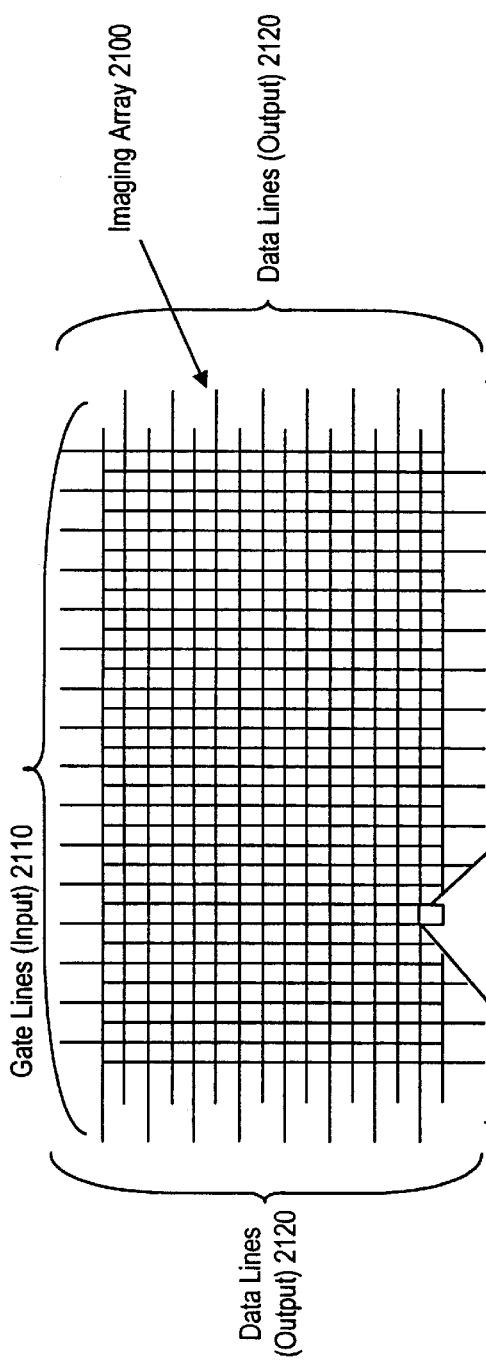
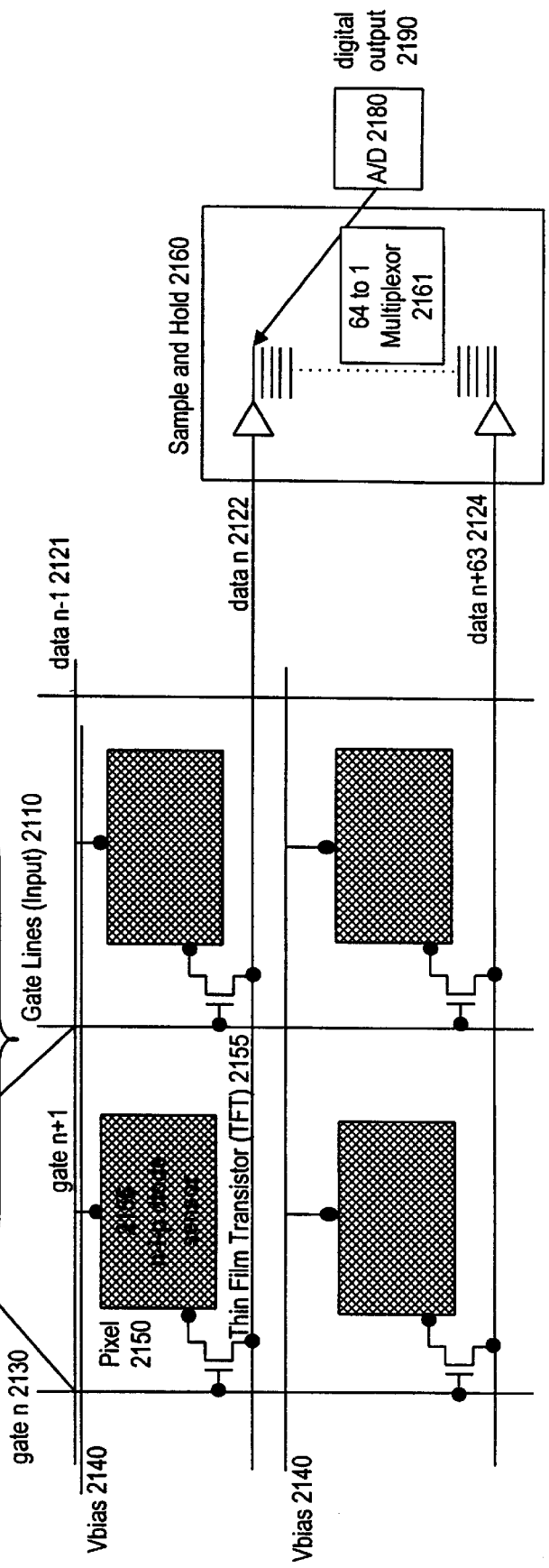
Figure 21

EXPLODED VIEW
OF REDUCED AREA DIGITAL
PANORAMIC CASSETTE
3100

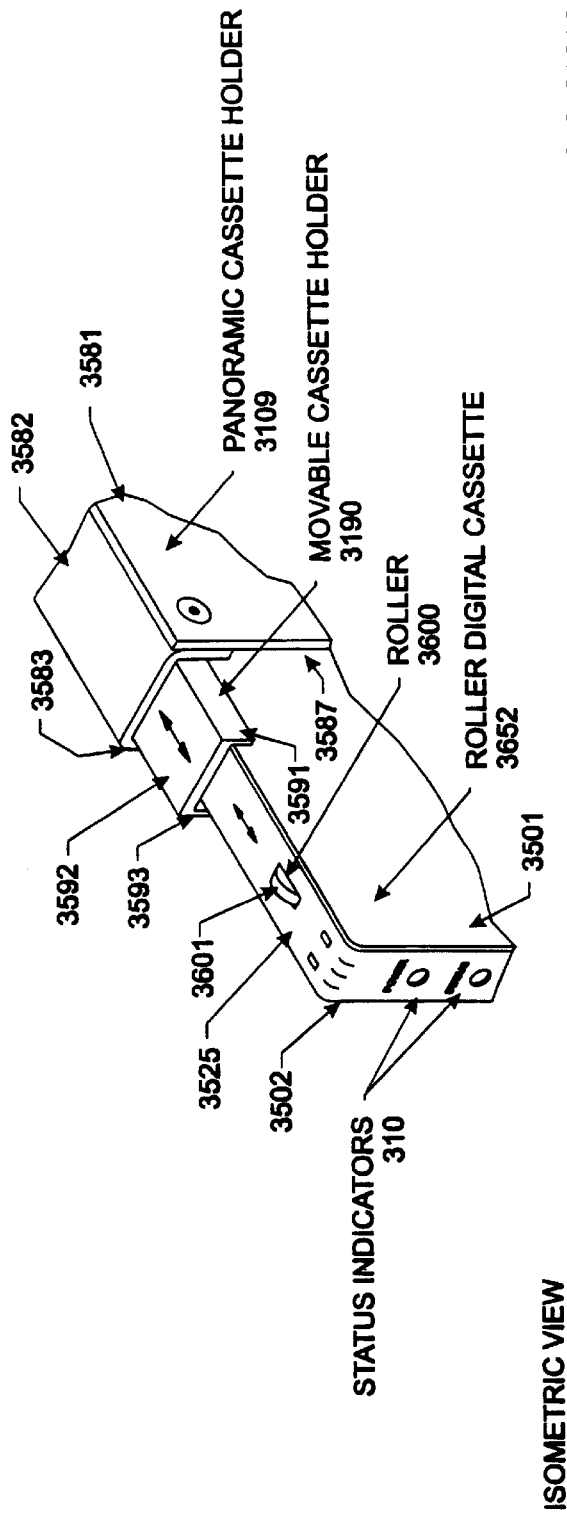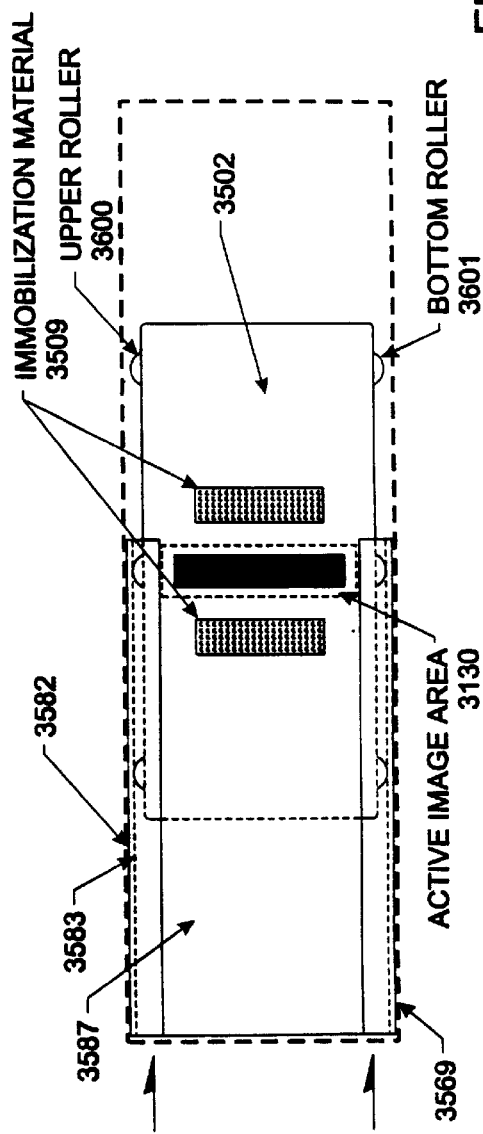
FIGURE 35

FILMLESS DIGITAL X-RAY SYSTEM

CROSS-REFERENCED APPLICATIONS

This invention is based upon U.S. Provisional Application Ser. No. 60/001,531, filed Jul. 26, 1995.

THE BACKGROUND OF THE INVENTION

A. The Field of the Invention

This invention relates to the field of medical imaging. In particular, the invention relates to a digital filmless x-ray cassette.

B. A Description of the Related Art

This invention relates to medical imaging systems. Film-based x-ray imaging has been in wide use since 1895. Film-based x-ray imaging is a proven and dependable method for capturing x-ray images. However, it fails to meet the emerging needs of modern imaging systems. With the greater use of personal computers in many industries, we see a shift towards modalities that produce digital images. In particular for the medical industry, digital images are becoming more and more important.

Certain proprietary, costly digital imaging systems have been developed, but none provide a low cost, high resolution system that is compatible with the current installed base of x-ray imaging machines.

Before exploring the limitations of present digital x-ray imaging systems, it is worth while to describe the limitations of present film-based x-ray systems.

FIG. 1 illustrates a typical x-ray system. The x-ray machine 101 has an x-ray source 110 and a film cassette 199. The x-ray tube 100 generates an x-ray beam that passes through a collimator 120 through the patient 180 and on to the film cassette 199. The film cassette 199 typically includes an illuminating screen and a light sensitive film. The x-rays cause the illuminating screen to glow producing an image on the film. Where the anatomic structures of the patient 180 block the x-rays, the illuminating screen will receive fewer x-rays. Thus those portions of the film will receive less exposure.

The following describes the typical process of taking an x-ray using a film-based x-ray system. First the film cassette 199 is loaded with the correct illuminating screen and the film. The illuminating screen is a rare earth element that glows when it is irradiated by the x-ray source 110 (emitter). Unfortunately this raises the first problem in taking an x-ray image, that is selecting the correct illuminating screen and film.

Different illuminating screens glow at different levels given the same amount of x-rays and have different response and retention characteristics. Similarly, different types of film will register an image at different rates given the same amount of light from the illuminating screen. Further, the screens and the film must be free of debris. However, every time a new film is placed in the cassette, there is a possibility of contaminating the screen or the film (such as a fingerprint). A contaminated screen or film will cause an obstructed image.

When the film is loaded in the film cassette 199, the cassette must be sealed light tight. Some x-ray cassettes from 3M, Inc. of Minnesota, (e.g., the Tri-max™ x-ray cassette), have two latches and a light tight barrier to help prevent light from entering the x-ray cassette and ruining the image. One of the problems with the present film cassette 199 is that once the film has been placed in the cassette it is possible to either forget that the film has been placed in the cassette or to double expose a given film. The problem lies in that the film cassette 199 does not typically indicate whether a film is inside the cassette or whether that film has been exposed.

The insertion of the film into the cassette is performed in the darkroom. No light can enter a darkroom or the film will become fogged. Similarly, if any light enters a darkroom the rest of the film not in the cassette, but in the darkroom, can also become fogged. The fogged film will then produce lower quality images.

Next the film cassette 199, having the film loaded in it, is inserted in the x-ray machine 101. The film cassette 199 has a front and a back. However, conventional film cassettes 199 can usually fit in either direction. Therefore, it is possible to load a film cassette 199 in backwards into the x-ray machine 101. This will result in an improperly taken x-ray.

One aspect of taking an x-ray is recording information identifying the patient and the date of the x-ray (tag information). The tag information is sometimes included in the x-ray image. In some systems a different processing machine is used to generate the tag information. In other systems the tag information is included as part of the film cassette 199. However, such a system does not typically allow you to collimate, that is reduce the area of x-ray exposure to the patient 180, because the tag information would then be excluded from the x-ray image. Further, identifying the top and bottom of the cassette now becomes important because of where the tag information is a concern. Although a cassette image can be taken on a film that is essentially upside down with respect to the tag image, the office standards will be compromised because of this. Therefore, it is desirable to include tag information in the x-ray image while avoiding the problems discussed above.

An additional problem to inserting the x-ray cassette into the x-ray machine 101 is that the technician needs to actually insert the film cassette 199 every time a new x-ray image is to be captured. This means both the film cassette 199 and the x-ray cassette holder 300 suffer mechanical wear.

Further, some systems provide motorized cassette holders that allow multiple x-ray images to be taken on one piece of film, each x-ray image being next to the previous x-ray image. Such systems are available from Imaging Systems, Inc. in Philadelphia, Pa. However, to simplify construction and increase reliability, it would be desirable to obviate the need of an x-ray motorized cassette holder but still allow multiple images to be taken with the same installed film cassette 199.

After the x-ray cassette has been loaded into the x-ray machine 101, the exposure factor for the x-ray source 110 must be determined. Typically three variables are used to set the exposure factor: the time of the exposure (the more exposure time the more radiation the patient receives), the amps supplied to the x-ray source 110, and the volts supplied to the x-ray source 110. The amperage determines the flow of the x-rays while the volts determine the intensity of the x-rays.

Setting exposure can introduce a number of problems. First, an incorrect exposure time, amps or volts setting can saturate a film image. That is, the exposure is too long and the image is over exposed. Similarly, it is possible to under expose an image. Moreover, overexposure to x-rays poses increased medical risk to the patient. Therefore it would be desirable to supply an imaging system that compensates for incorrect exposure settings on the x-ray source 110.

Next, the x-ray image is taken. The film cassette 199 is removed and taken into the darkroom. The film is then developed in the dark room. Typically the developing involves a number of hazardous chemicals and a relatively expensive developing machine. It is desirable to remove the need to have the hazardous chemicals and the developing machine. Further, it is desirable to provide x-ray images much faster than are provided in film-based x-ray systems. Film developing systems usually take between 90 seconds and 5 minutes or more to produce a single image.

Regarding present digital x-ray systems, these systems tend to be expensive and involve proprietary digital imaging hardware and x-ray machines. Therefore, medical facilities wishing to use digital x-ray imaging systems are required to purchase entirely new x-ray machines with the integrated digital imaging systems. Thus, present digital imaging systems do not provide a digital imaging solution for the large installed base of x-ray machines 101 that presently support film cassettes 199. It is therefore desirable to supply a digital x-ray imaging system that is backwards compatible with the large installed base of x-ray machines 101.

Typically, digital x-ray systems use either charge coupled devices (CCDs) or charged phosphors (CR) to capture digital x-ray images. CCD digital x-ray systems are available from Trophy, Inc. and Schick, Inc. CR digital x-ray systems are available from Sordex-Findndent, Inc. and Fuji, Inc.

CCD systems directly capture a portion of the x-ray image. CCD systems include a relatively small CCD sensor (adequate for intra-oral applications, for example, but not to replace large film sizes). It is desirable to have a direct capture digital x-ray cassette that has external dimensions approximately equal to a large size standard film cassette and has an active sensing area comparable to the size of the corresponding film for that large size standard film cassette. Further, because the sensor size is small, to capture images of the complete area of interest in some anatomic structures, additional exposures need to be taken. This has the undesirable effect of increasing the radiation dosage received by the patient.

CR systems have a sensing area approximately the same as the film that they replace. However, CR systems require a scanning of the phosphor after an image has been captured on it. This is somewhat analogous to scanning processed film images. This additional scanning step processes the image captured on the phosphor and turns it into a digital x-ray image. CR systems therefore require more time to capture the digital x-ray image than direct capture systems, such as CCD systems. Therefore, it is desirable to have a direct capture digital x-ray system. Also, present CR systems are integrated with the x-ray tube and the x-ray machine generator, thereby increasing the capital equipment costs of the CR systems. As noted above, it is desirable to reduce the capital equipment costs of the digital x-ray capture system by using already installed x-ray machine.

An example of an x-ray diagnostic apparatus using radiation detectors rather than film is described in U.S. Pat. No. 4,188,537 (hereinafter referred to as Franke). Franke describes an apparatus where, instead of having a film holder for the carrier and film for the radiation receiver, the apparatus has a plurality of radiation detectors which are transducer means for measuring radiation intensity. However, Franke has a number of drawbacks. In particular, Franke does not teach a radiation detector that is capable of being used in present x-ray machines. That is, the Franke radiation detector does not have external dimensions that would enable the radiation detector to be used in an x-ray machine that accepts standard x-ray film cassettes.

Additionally, Franke does not describe how the radiation detector would be powered if the detector were to be used in a standard x-ray machine. Franke does not describe how images from the detector could be easily transmitted from the detector to the display device if the detector were to be used in a standard x-ray machine. Further Franke does not describe how to begin capturing an image when the radiation detector is used in a standard x-ray machine. Thus, Franke has a number of limitations.

Another example of an x-ray diagnostic apparatus using radiation detectors instead of film is described in U.S. Pat. No. 4,878,234 (hereinafter referred to as Pfeiffer et al.). Pfeiffer et al. discloses a system where the x-rays cause a scintillation layer to emit visible light. The visible light is transmitted, via a light transmitter(s), to one or more CCD sensors. The sensors the provide digital signals corresponding to the light. One drawback of the Pfeiffer et al. is the need to include the light transmitter(s). The light transmitters increase the size of the radiation detector, reduce the amount of light transmitted to the detectors, and increase the complexity of manufacturing the radiation detector. Like Franke, Pfeiffer et al. does not teach a radiation detector that is capable of being used in place of a standard x-ray film cassette.

Another example of an x-ray diagnostic apparatus using radiation detectors instead of film is described in U.S. Pat. No. 4,823,369 (hereinafter referred to as (Guenther et al.). Guenther et al. uses an amorphous silicon image recorder having a scintillation layer applied thereto, or coupled to the image recorder via a fiber-optic plate. As with the other inventions, Guenther et al. does not describe a radiation detector that can be substituted for a standard x-ray machine film cassette. Additionally, the scintillation layer is taught to be a layer formed on the image recorder or coupled to the image recorder by a fiber optic plate. Where the scintillation layer is formed directly on the image recorder, this arrangement does not make clear how one would be able to change the scintillation layer without having replace the relatively expensive image recorder. Additionally, forming the scintillation layer on the image recorder introduces one more manufacturing step in the processing of the image recorder. Where the scintillation layer is coupled to the image recorder by the fiber optic plate, the fiber optic plate increases the size of the x-ray detector and increases the cost of manufacturing the image detector.

Therefore, it is desirable to have a digital x-ray imaging system that does not suffer from the above-noted problems with present x-ray systems including present digital x-ray systems.

2. A SUMMARY OF THE INVENTION

A filmless digital x-ray cassette comprising the following. A standard sized x-ray cassette housing having external dimensions approximately equal to the external dimensions of a standard x-ray cassette. An array system having a plurality of light sensitive pixels, the array system being disposed at least partially within the standard sized x-ray cassette housing. An electronics system, coupled in communications with the array system. The electronics system converts pixel values received from the array system into a digital image. A communications circuit, coupled to the electronics system, having a digital image output.

3. A BRIEF DESCRIPTION OF THE DRAWINGS

The figures illustrate the invention by way of an example, and not limitation, like references indicate similar elements.

FIG. 21 illustrates an imaging array.

FIG. 35 illustrates a digital panoramic cassette having upper and lower rollers.

4. THE DESCRIPTION OF THE PREFERRED EMBODIMENT

A. AN OVERVIEW OF AN EMBODIMENT OF THE INVENTION

In the following description, specific details are given such as the dimensions of various components within a digital cassette, to provide a thorough understanding of the invention. In other instances known structures and techniques have not been described in detail so as not to obscure the invention.

B. A DIGITAL X-RAY IMAGING SYSTEM

Figure 1:
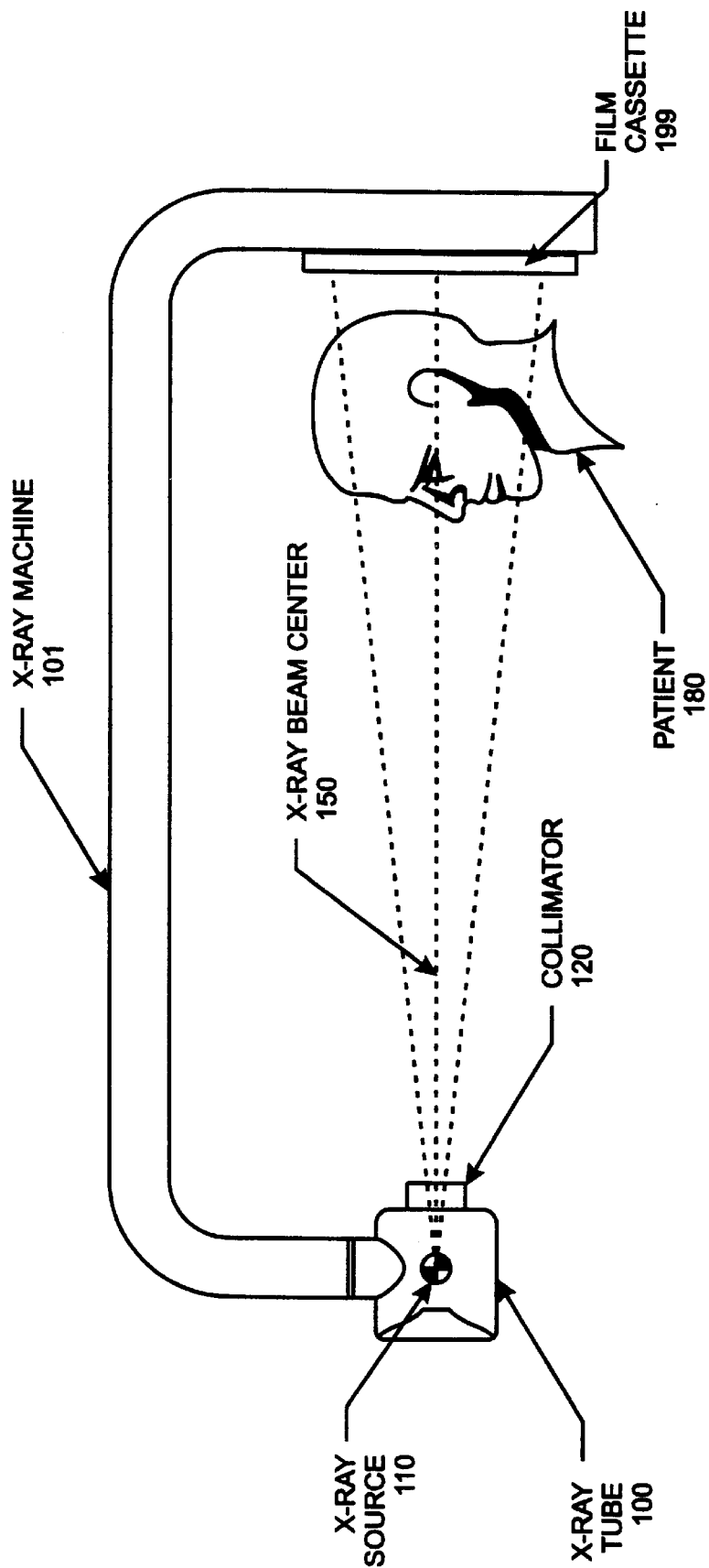
FIG. 1 illustrates a film-based x-ray imaging system.
Figure 2:
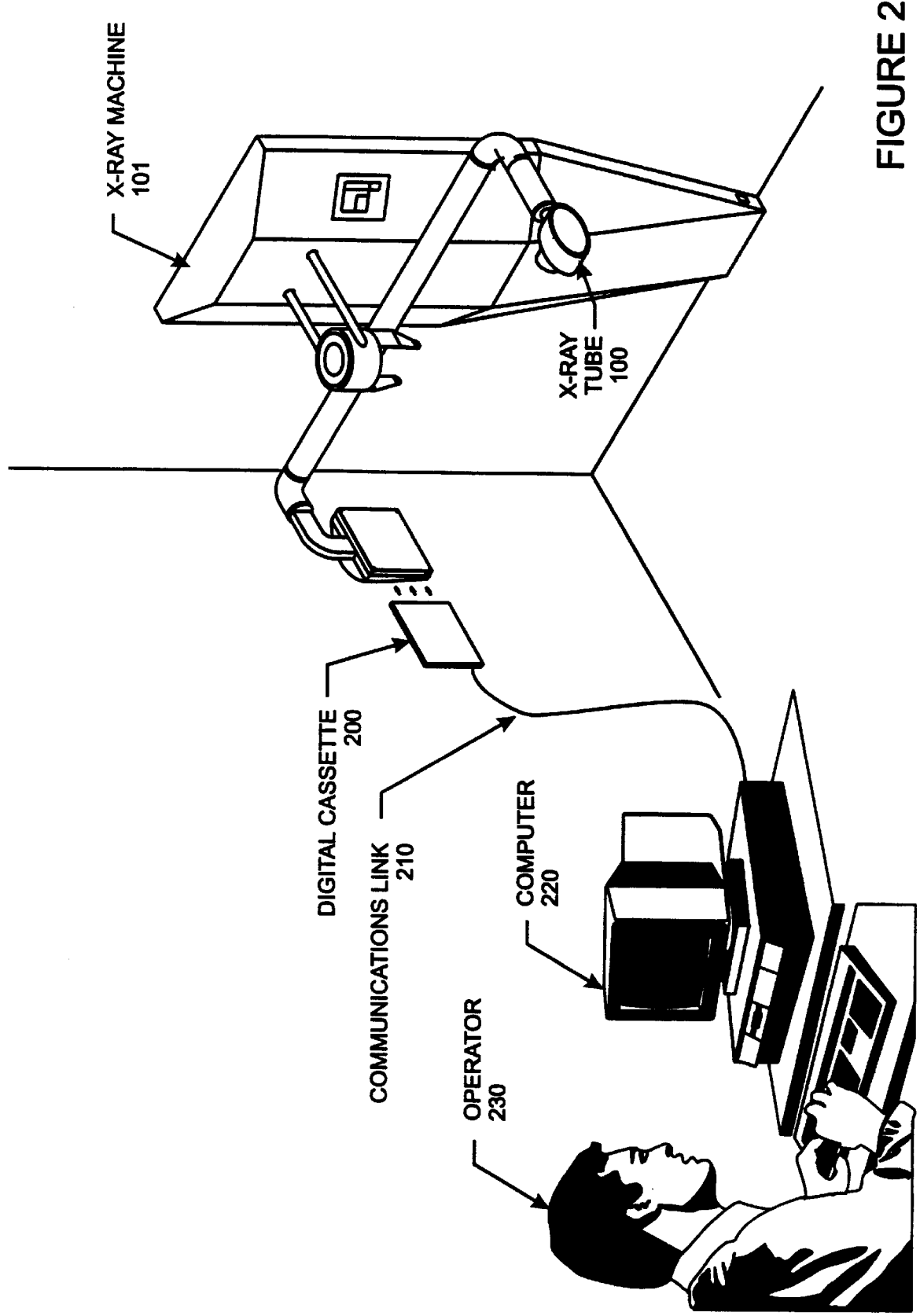
FIG. 2 illustrates a filmless digital x-ray imaging system.

FIG. 2 illustrates a filmless digital x-ray imaging system. Under the guidance of a human operator 230 a digital cassette 200 captures images in the digital x-ray imaging system. The digital x-ray imaging system includes the x-ray machine 101, a computer 220, the digital cassette 200, and a communications link 210 between the digital cassette 200 and the computer 220.

The digital cassette 200 is loaded into the x-ray machine 101 as would a normal film cassette 199 be loaded into the x-ray machine 101. A communications link 210 is established between the digital cassette 200 and the computer 220. To digitally capture the x-ray image, the operator 230 initiates the x-ray sequence of the x-ray machine 101 normally as when using a film cassette 199. However, rather than having to develop an x-ray film, the digital cassette 200 directly captures the x-ray image. The digital cassette 200 communicates the image to the computer 220. The operator 230 can then view the x-ray image on the computer 220.

The computer 220 can be executing image display software from, for example, Tau Corporation of Los Gatos, Calif.

Of particular importance is that digital cassette 200 is designed to match the size of traditional film cassettes 199. By matching the standard exterior dimensions of the existing film base cassettes, the digital cassette 200 will be compatible with the entire existing installed base of x-ray machines 101, and with all manufacturers' new systems built to film-based standards. Table 1 illustrates three typical traditional film cassette sizes.

TABLE 1

| Film Size | Approximate Cassette Exterior Dimensions |
|---|---|
| 5" × 12" | 6" H × 13" W × 9/16" D |
| 8" × 10" | 9" H × 11" W × 9/16" D |
| 15 cm × 30 cm | 7" H × 13" W × 9/16" D |

C. A DIGITAL CASSETTE

Figure 3:
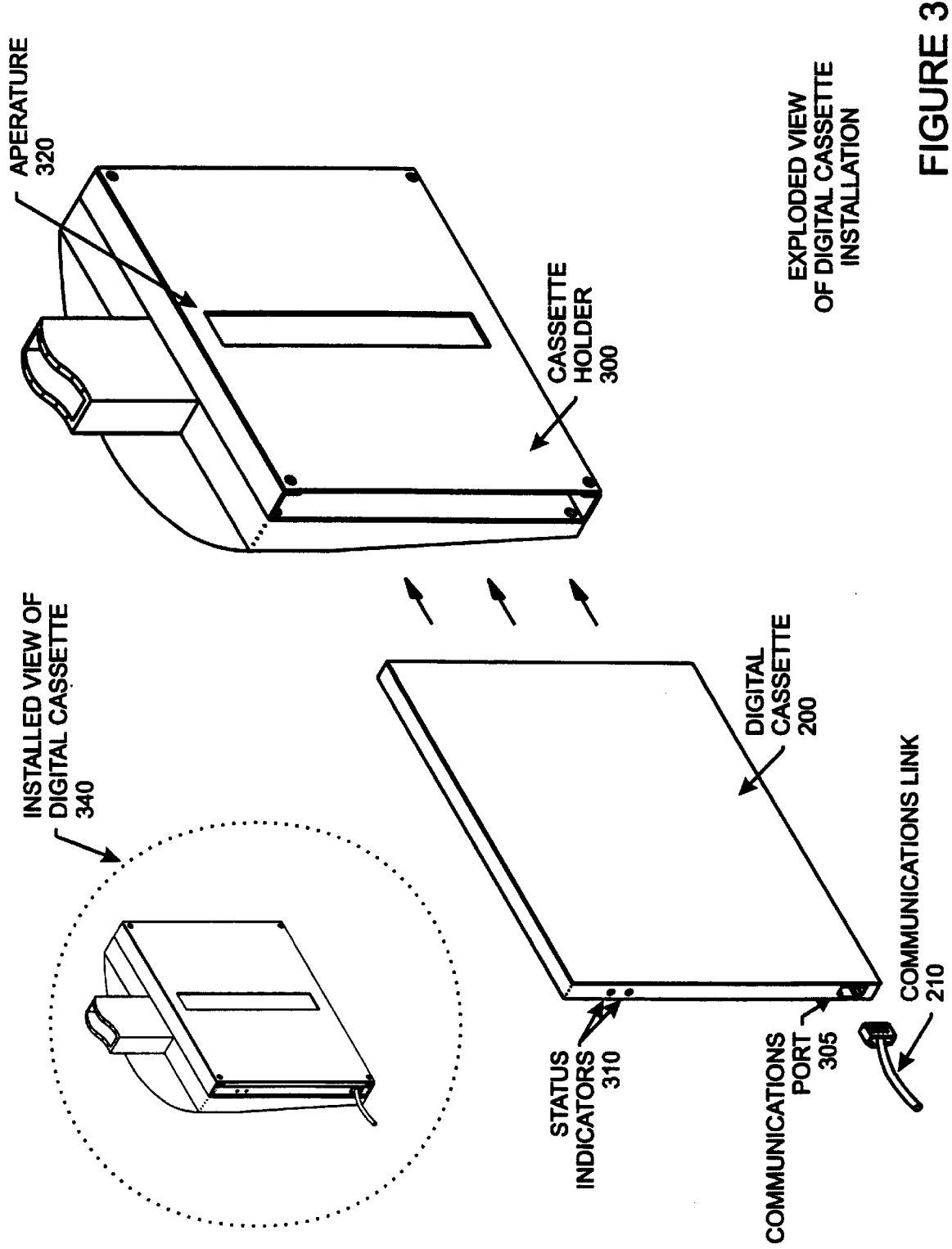
FIG. 3 illustrates a digital cassette and cassette holder.

FIG. 3 illustrates a digital cassette 200 and cassette holder 300. FIG. 3 illustrates digital cassette 200 as about to be installed in cassette holder 300 and a view of the installed digital cassette 340.

Again, what is particularly important here is that digital cassette 200 has the same form factor (external dimensions) of standard film cassettes 199.

In one embodiment, the digital cassette 200 has the almost identical external appearance to a standard film cassette 199.

In one embodiment, the digital cassette 200 includes a communications port 305 and status indicators 310 to provide information to the operator 230. The communications port 305 is for establishing communications link 210 between the digital cassette 200 and the computer 220.

FIG. 3 also illustrates a cassette holder 300. In this example the cassette holder 300 is a cassette holder for a limited area of exposure x-ray picture such as is used on tomographic or panoramic x-ray imaging. This is described in greater detail below and it is worthwhile to point out that the cassette holder 300 includes aperture 320 that allows x-rays to pass through the cassette holder 300 and onto the digital cassette 200. The cassette holder 300 is typical of the current x-ray systems that rely on industry standard sized film cassettes.

Some x-ray system manufacturers offer their own line of film cassettes 199, but so as not to exclude themselves from advances in screen and film technology, most manufacturers support the industry standards. Most x-ray machines 101 are designed with a specific function in mind, such as a panoramic x-ray machine, and use, the most suitable standard cassette sizes for their applications. In order to accept cassettes from various manufacturers, most cassette holders 300 provide some allowances for variation in standard cassette dimensions. Cassette holders 300 can have fixed mounting channels that are slightly larger than the standard cassette sizes, or include adjustable mounts that clamp a cassette into position. However, most systems allow an operator to manually install a cassette by sliding it into position.

One embodiment of the digital cassette 200 has approximately the same dimensions as a standard film cassette 199. That is, no status indicators 310 or a communications port 305 are included in the digital cassette 200. To provide for the widest compatibility among different x-ray machines 101, whenever possible, the communications port 305 and the status indicators 310 are mirrored on both ends of the digital cassette 200. This allows the status indicators 310 to be viewable from either end of the digital cassette 200. Further, this allows the communications link 210 to be established at either end of the digital cassette 200.

As shown in the view of the installed digital cassette 340 the digital cassette 200 slides into the cassette holder 300 as a regular film cassette 199 would.

D. 8½"×10" DIGITAL CASSETTE

Figure 4:
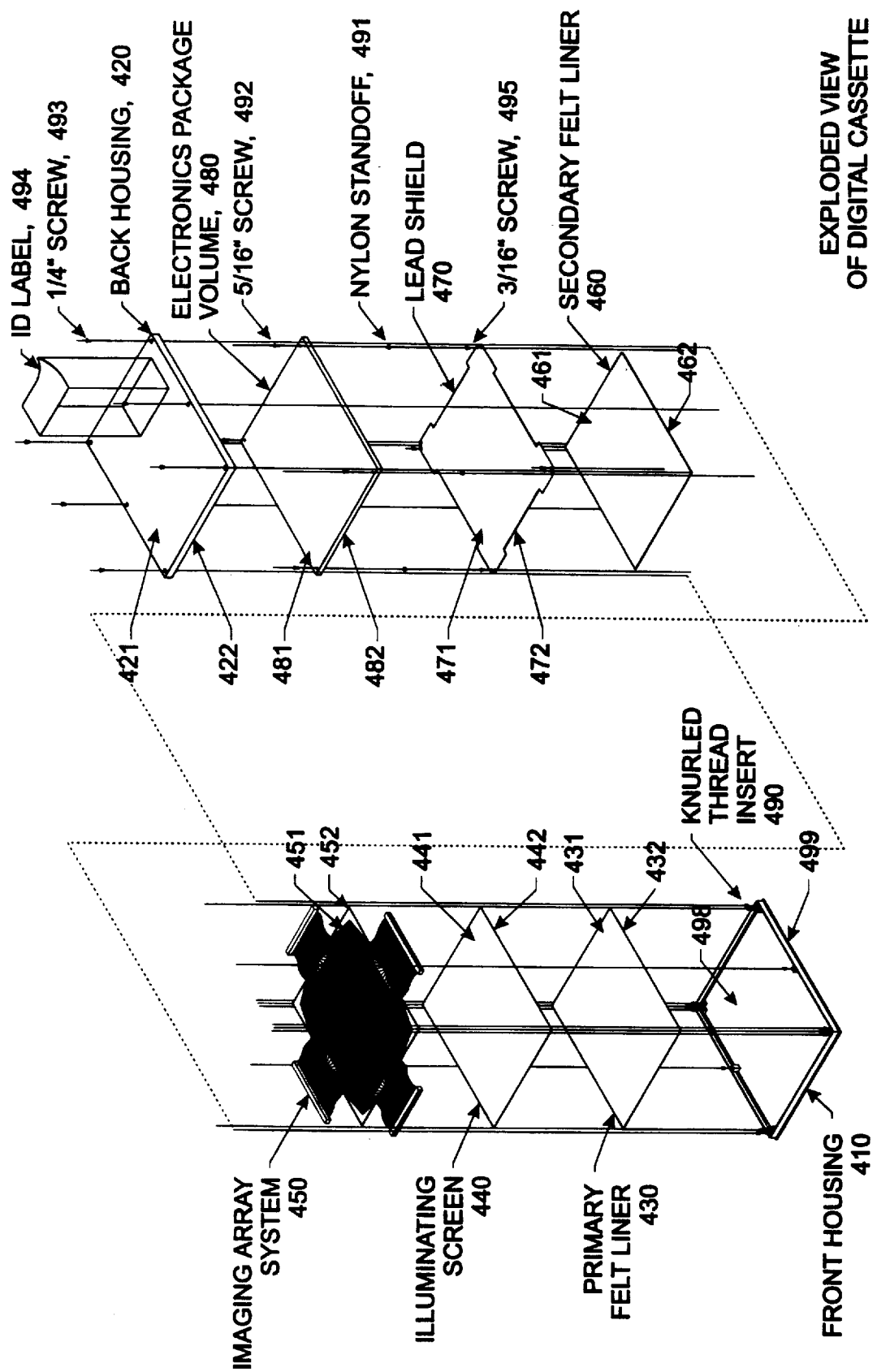
FIG. 4 illustrates an isometric view of a digital cassette
Figure 5:
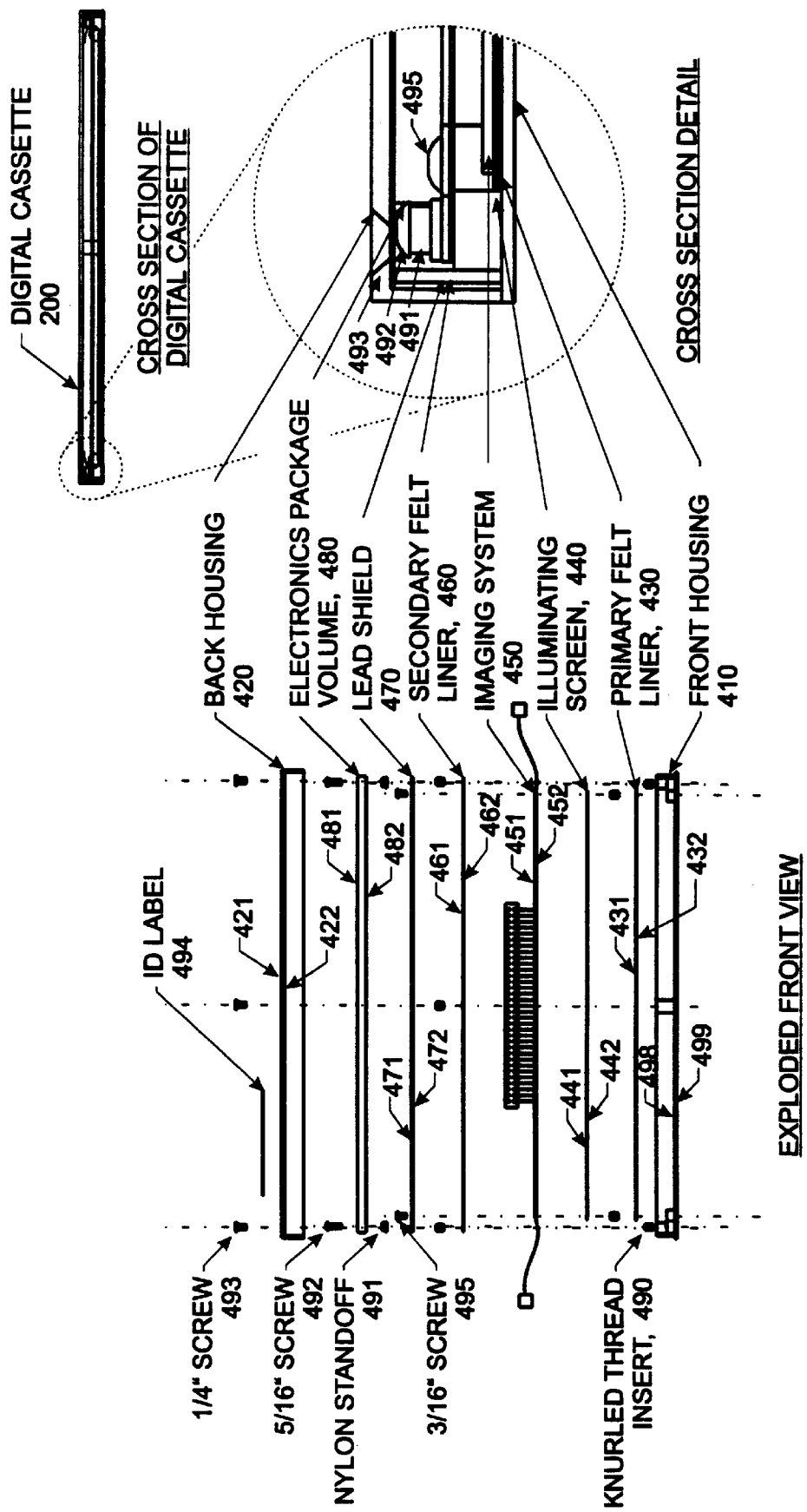
FIG. 5 illustrates a cross-section view of a digital cassette.

FIG. 4 illustrates an exploded isometric view of a digital cassette 200. FIG. 5 shows a cross-sectional view of a digital cassette 200. The combination of the components of FIG. 4, in one embodiment, correspond to the digital cassette 200. The digital cassette shown in FIG. 4 is illustrative of one embodiment of an 8½"×10" standard form factor cassette. However, by varying the proportion of the components in FIG. 4, various standard sizes of digital cassettes can be realized. For example, a 5"×12" form factor could also be realized using the components of FIG. 4.

Figure 6A:
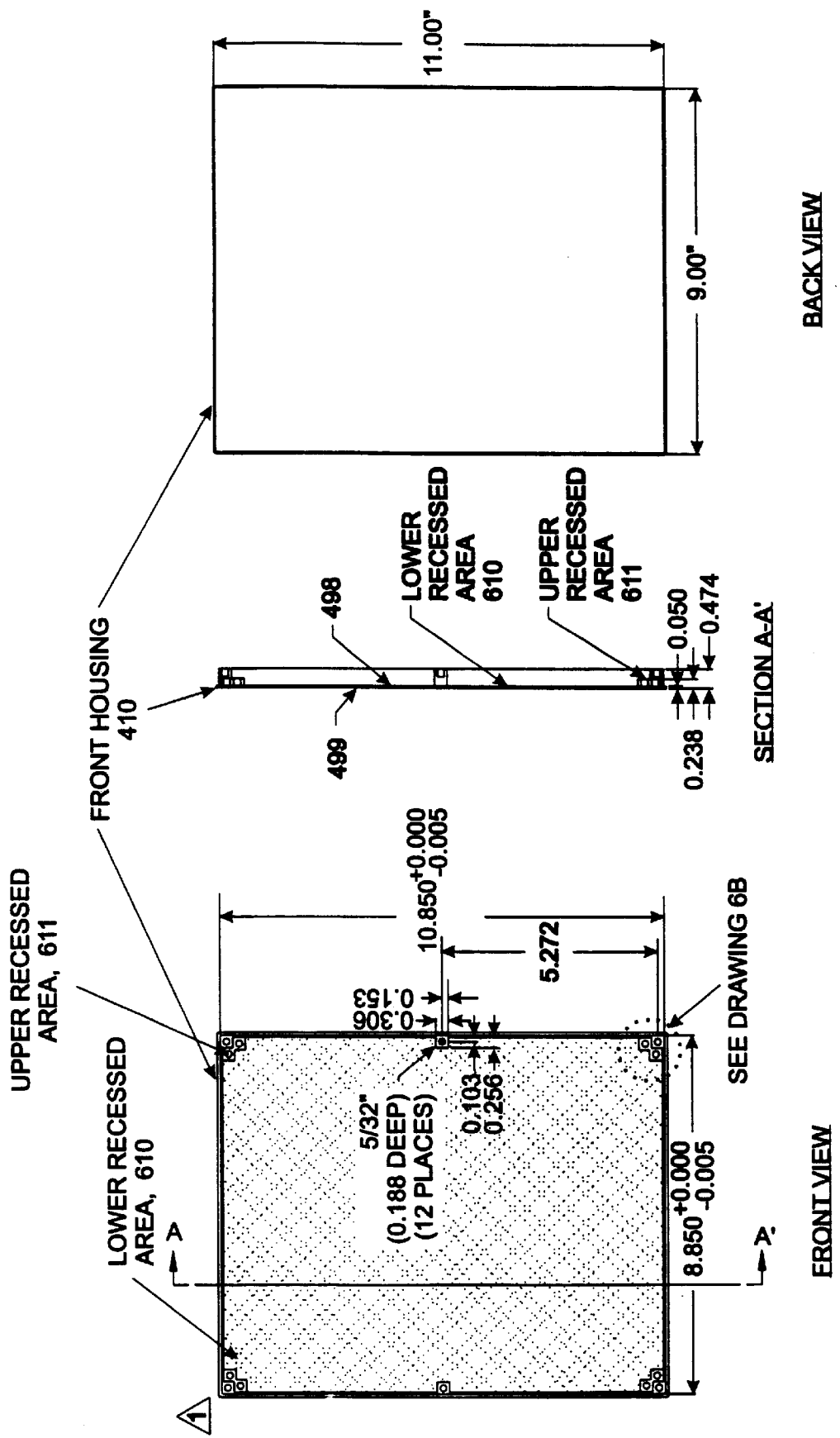
FIG. 6A and FIG. 6B illustrates a front housing of a digital cassette.
Figure 6B:
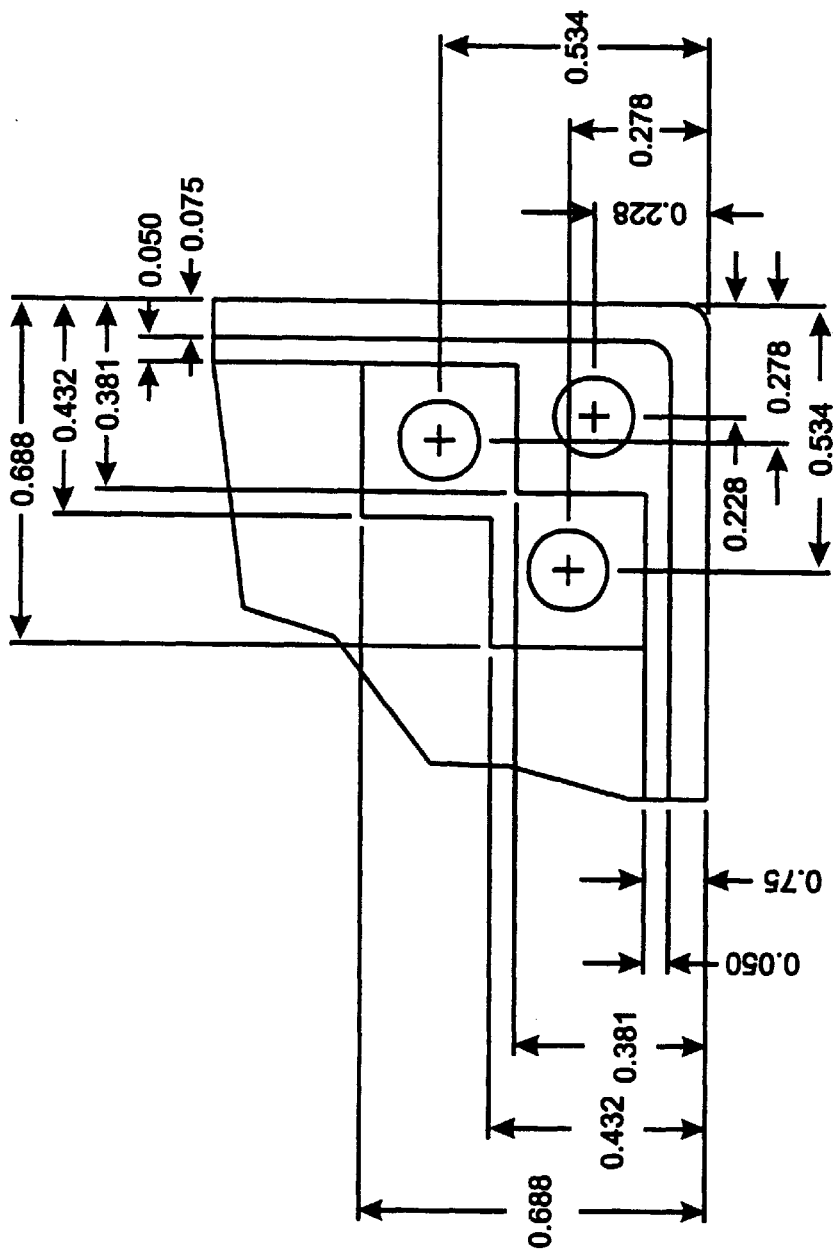
Figure 7:
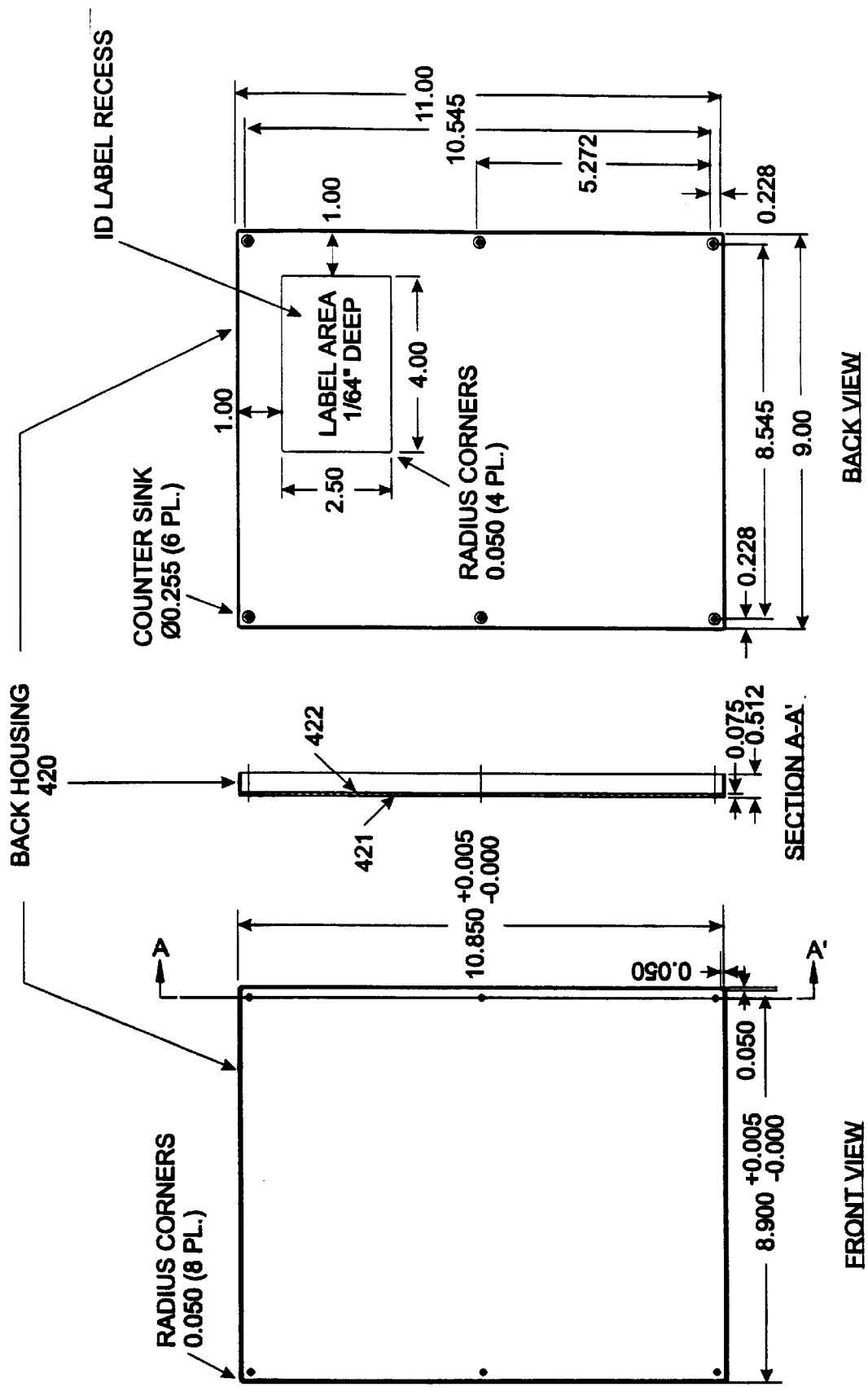
FIG. 7 illustrates a back housing of a digital cassette.

The digital cassette 200's housing is comprised of two halves, a front housing 410 shown in FIG. 6A and FIG. 6B and a back housing 420 shown in FIG. 7. When assembled the front housing 410 and the back housing 420 form a rigid, light tight assembly to house the internal components of the digital cassette 200. Importantly, the front housing 410 and the back housing 420 combine to form dimensions corresponding to a standard film cassette 199.

In one embodiment the two housing components, front housing 410 and back housing 420, are joined by screws, one-quarter inch screw 493, for example. One-quarter inch screw 493 passes through counter-sunk holes in the back housing 420. One-quarter inch screw 493 threads into knurled thread insert 490. Knurled thread insert 490 is pressed into holes in the corners of the front housing 410.

In one embodiment, the front housing 410 and the back housing 420 are molded plastic. In another embodiment front housing 410 and the back housing 420 are machined aluminum or some other rigid material. One important aspect of the front housing 410 and the back housing 420 is that they provide structural support for the other components contained within the digital cassette. As noted below, the imaging array system 450 includes a thin glass plate, that will need structural support from the front housing 410 and the back housing 420.

In another embodiment, the digital cassette 200 has a front housing 410 and a back housing 420 that are glued or snap fitted together.

In one embodiment, the back housing 420 includes a shallow recess for the ID label 494. The ID label 494 can include information such as the digital cassette 200's serial number, model number, and other manufacturing information as required by the FDA, or other regulatory agency.

Front housing 410 and back housing 420, in one embodiment, also include openings for status indicators 310 and communications port 305. In one embodiment, front housing 410 and back housing 420 are modified slightly to allow for these openings but still maintain light tight housing. Layered into the front housing 410 are the components required for sensing the x-ray image: primary felt liner 430, illuminating screen 440, imaging array system 450, secondary felt liner 460, and a lead shield 470. The remaining space between the lead shield 470 and the back housing 420 defines an electronics package volume 480.

Figure 8:
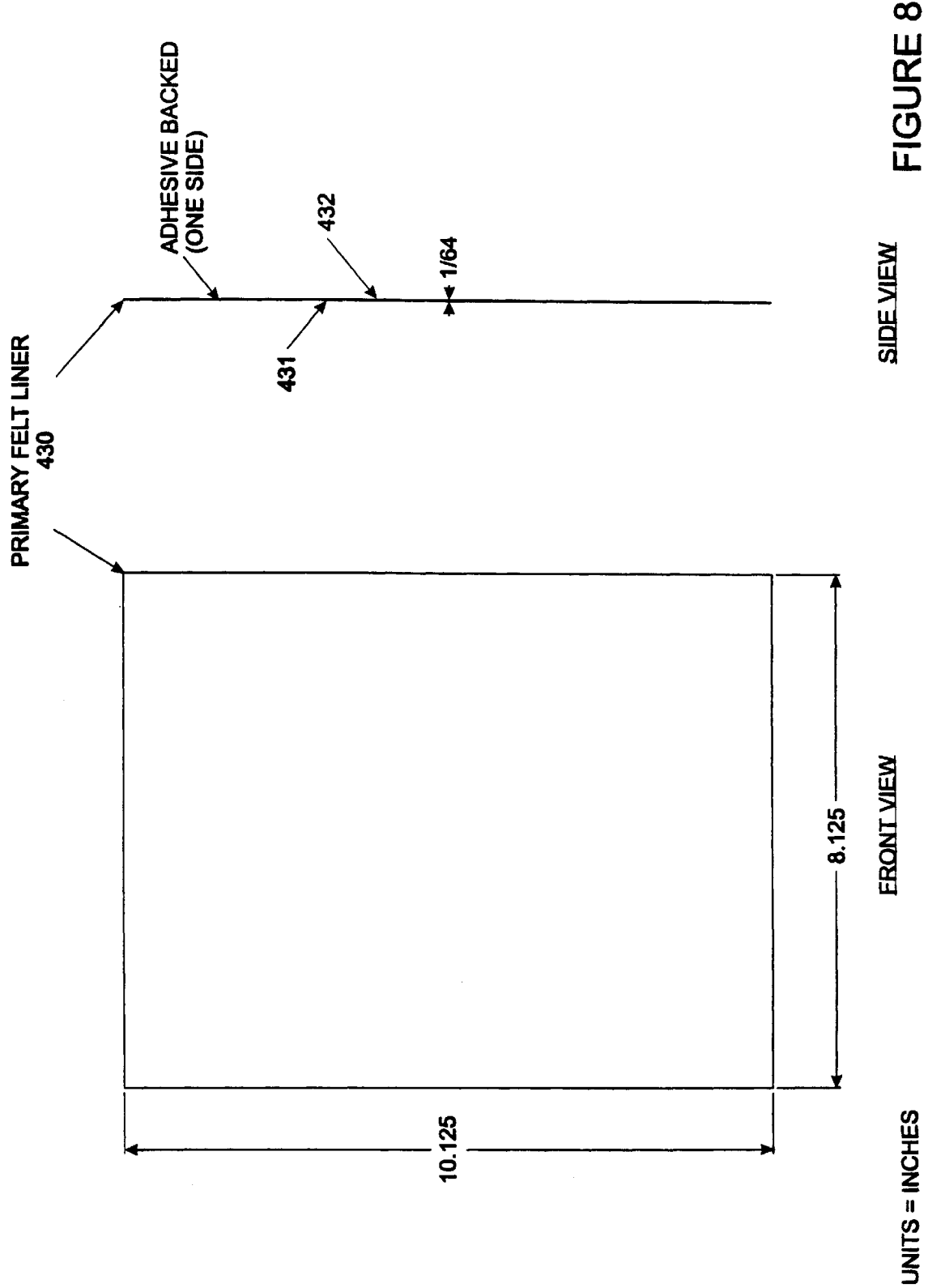
FIG. 8 illustrates a primary felt liner.

The primary felt liner 430 is placed into the bottom of the internal recess in the front housing 410. The primary felt liner 430 provides a cushion for the remaining components and compensates for irregularities in the manufacture of the front housing 410. As shown in FIG. 8, the primary felt liner 430 matches the width and height dimensions of the recess in the front housing 410 (shown in FIG. 6A and 6B ). FIG. 8 illustrates the primary felt liner 430. The primary felt liner 430 has an adhesive bottom surface 432. The adhesive bottom surface 432 helps to keep the primary felt liner 430 from moving during manufacture and use of the digital cassette 200.

Figure 9:
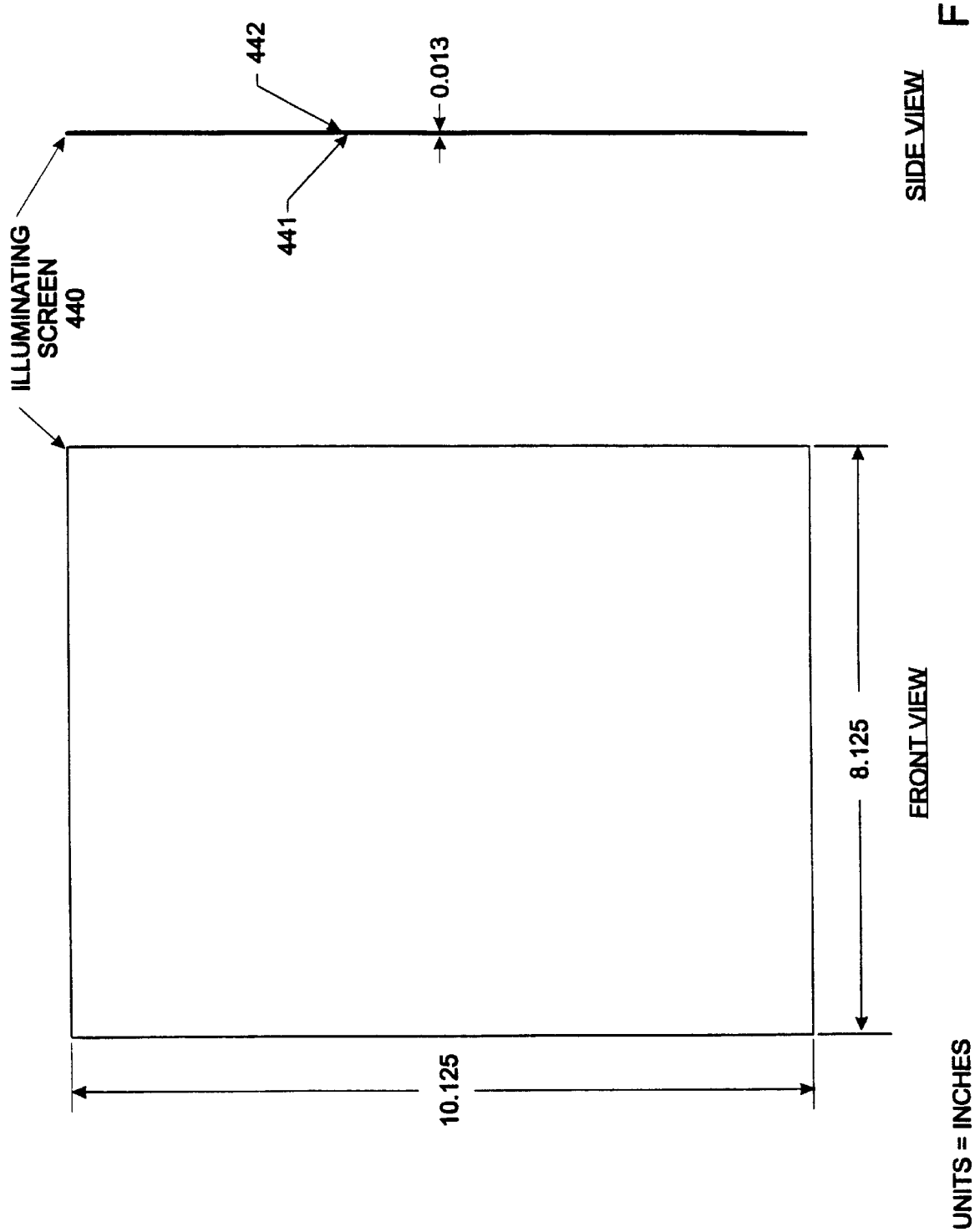
FIG. 9 illustrates an illuminating screen.
Figure 10:
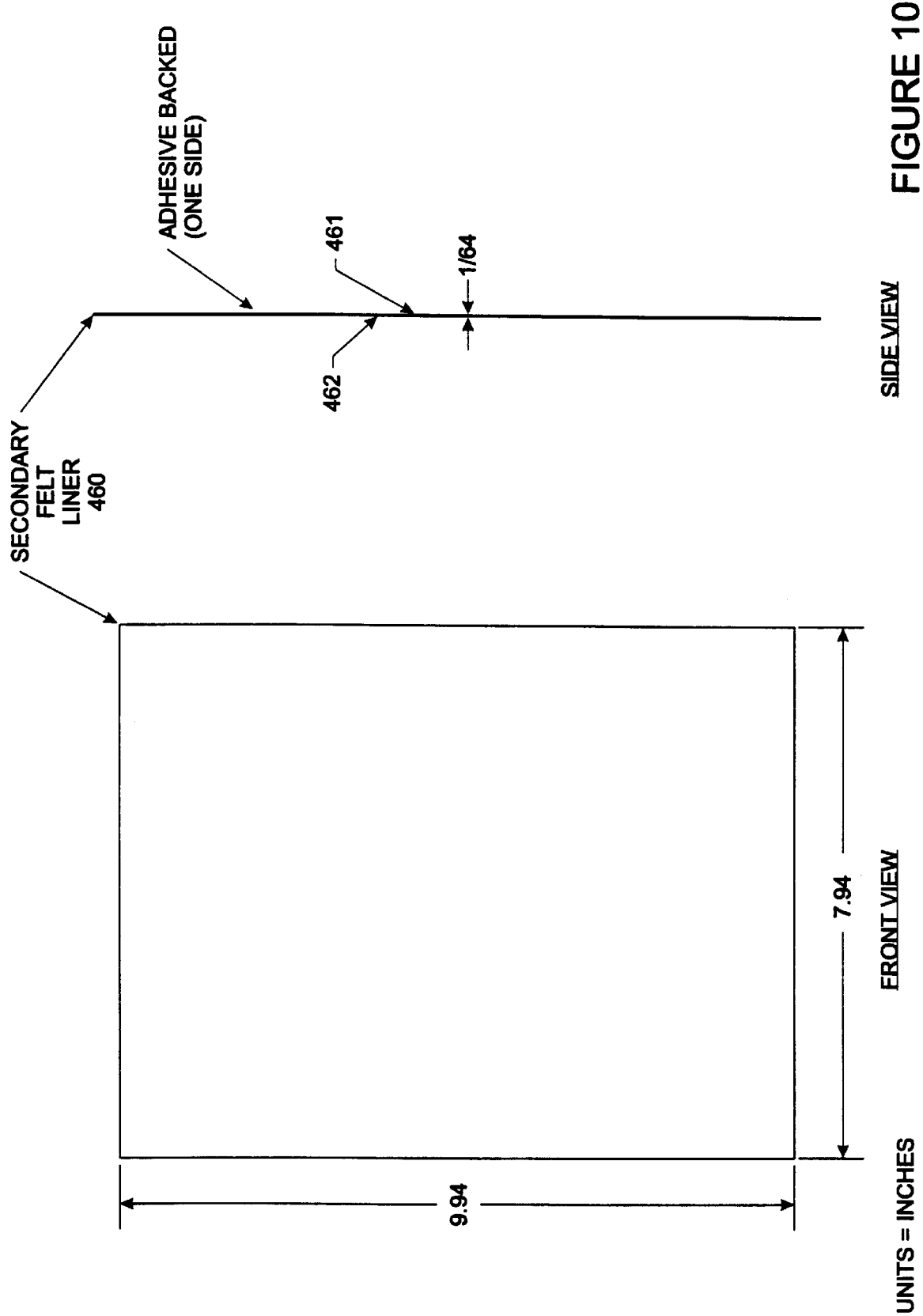
FIG. 10 illustrates a secondary felt liner.

Next, the illuminating screen 440 is placed in direct contact with the back surface of the primary felt liner 430. The illuminating screen 440 performs the same function as it would in a traditional film-based x-ray system, producing light when the illuminating screen 440 is bombarded with x-rays. The light is then converted into a digital image by light sensitive circuitry that covers the majority of the imaging array system 450. An example, illuminating screen 440 is a Kodak Lanex™ screen. Suitable illuminating screens 440 can be obtained from other manufacturers. The width and height of the illuminating screen 440 matches the full available space of the recess in the front housing 410. This insures that illuminating screen 440 covers all the light sensitive areas of the imaging array system 450. In one embodiment, the illuminating screen 440 has notches in the edges of the screen to allow room for the passage of ribbon cables from the front surface of the imaging array system 450. FIG. 9 shows the dimensions of one embodiment of illuminating screen 440.

In one embodiment, the illuminating screen 440 is not included in the digital cassette 200. In this embodiment, the imaging array system 450 directly detects the x-rays. However in one embodiment, the illuminating screen 440 is included because the imaging array system 450 better detects visible light than x-rays.

Figure 12:
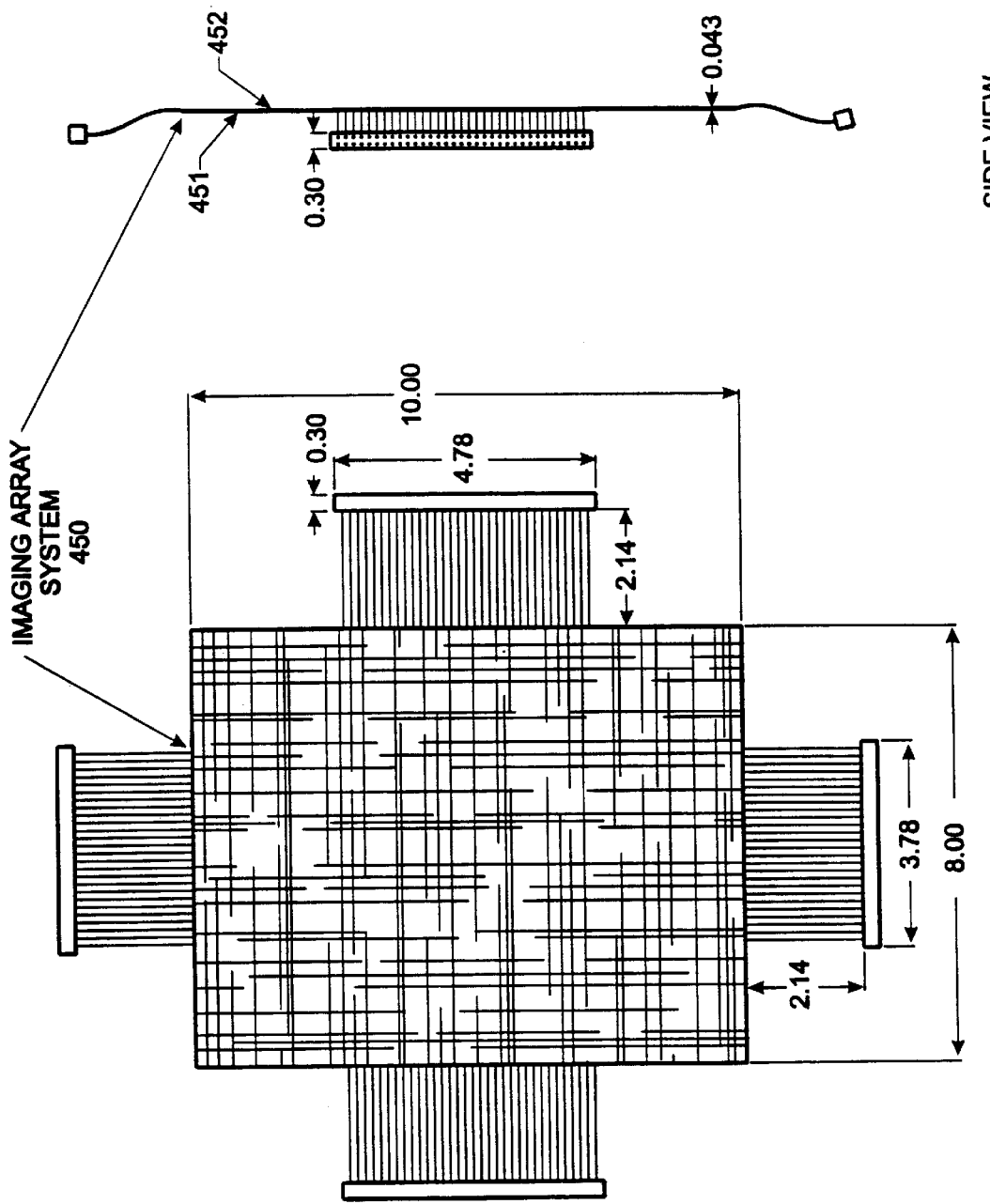
FIG. 12 illustrates an imaging array system.

The imaging array system 450 is placed in direct contact with the illuminating screen 440. FIG. 12 illustrates the dimensions of one embodiment of the imaging array system 450. Note the glass substrate on which the light sensitive pixels are located is relatively thin. In one embodiment the glass substrate is 0.043". This relatively thin piece of glass requires a significant amount of structural support from the digital cassette 200 housing. The imaging array system 450 includes a glass substrate having a number of pixels that sense light. The areas of the imaging array system 450 that include these light sensitive pixels find the active area of the imaging array system 450. In one embodiment, the active area of the imaging array system 450 is centered within the overall height and width of the front housing 410. In one embodiment, the imaging array system 450 is restrained from any lateral motion because of the recess of the front housing 410.

In one embodiment, flat ribbon cables are wire bonded to the front surface of imaging array system 450. The flat ribbon cables are curled towards the electronics package volume 480. Thus, the flat ribbon cables can communicate information between the light sensitive pixels and the electronics package volume 480.

In one embodiment, rather than flat ribbon cables, tab packaging with flex circuits are used to form the communications link between the electronics package volume 480 and the imaging array system 450.

In one embodiment, it is important that the back surface of the front housing 410 is in direct contact with the front surface of the primary felt liner 430, that the back of the primary felt liner 430 is in direct contact with the front of the illuminating screen 440, that the back of the illuminating screen 440 is in direct contact with the front of the imaging array system 450. The direct contact between these components allows for a good quality image as the light from the illuminating screen 440 is directly communicated to the light sensitive pixels in the imaging array system 450.

After the imaging array system 450, the secondary felt liner 460 is placed in direct contact of the rear surface of the imaging array system 450. The secondary felt liner 460 protects the imaging array system 450 from damage and acts as a cushion between the imaging array system 450 and the lead shield 470. The adhesive surface 461 of the second felt liner 460 helps to keep the secondary felt liner 460 from moving during the manufacture and the use of the digital cassette 200.

Next, a lead shield 470 is placed in direct contact with the adhesive surface 461 of the secondary felt liner 460 and secured in place using three-sixteenth screw 495. The lead shield 470 is an optional sheet of lead that helps to prevent the further transmission of x-rays into the electronics package volume 480 and beyond the back housing 420. Lead shield 470 acts as a retaining bracket securing the primary felt liner to illuminating screen 440, the imaging array system 450, and the secondary felt liner 460. The lead shield 470 also acts as a heat shield and evenly distributes heat generated by the imaging array system 450 and the electronics package volume 480. Finally, the lead shield 470 acts as a light shield protecting the back surface 451 of the imaging array system 450 from any stray light that may enter the digital cassette 200. For example, if holes are made in the back housing 420 to allow for the status indicators 310 and the communications port 305 then it is possible that light may enter the digital cassette 200 when assembled. However, the lead shield 470 will help to prevent this stray light from coming in contact with imaging array system 450.

Figure 11:
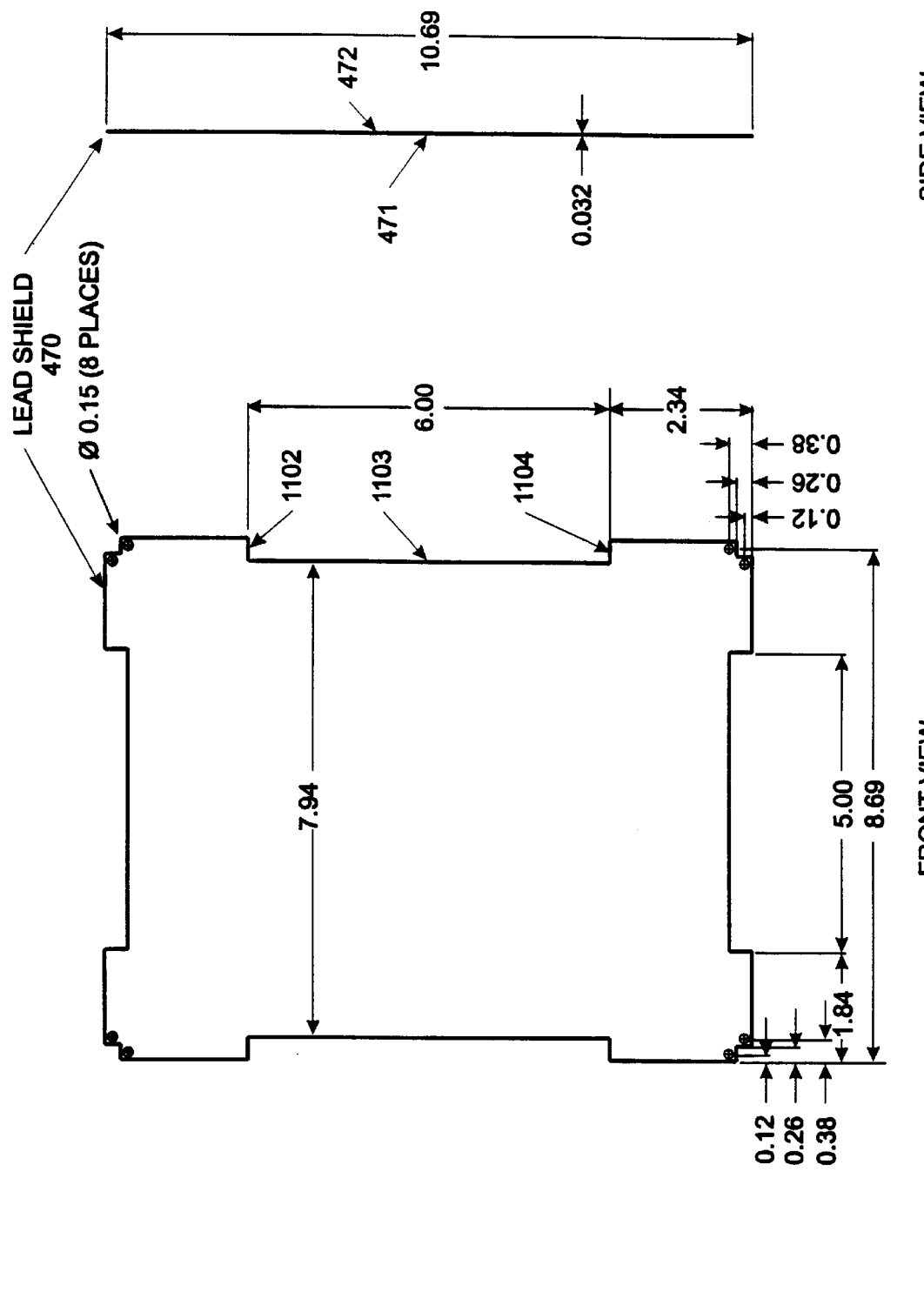
FIG. 11 illustrates a lead shield.

FIG. 11 illustrates one embodiment of the lead shield 470. The width and height of the lead shield 470 covers the full available height and width of the lower recessed area 610. In one embodiment, lead shield 470 includes notches. One notch is defined by edge 1102, edge 1103, and edge 1104. The notches allow for the passage of the communications cable from the imaging array system 450 to the electronics package volume 480.

The electronics package volume 480 defines an area that will allow for an electronic system being included in digital cassette 200. The electronics system will be able to process the information captured by the imaging array system 450 and communicate that information to the computer 220. The electronic system is described in greater detail below.

Note the lead shield 470, the secondary felt liner 460, and the illuminating screen 440, and the primary felt liner 430 are all optional. Removing these components will allow for greater electronics package volume 480. However as noted above, each of these components has certain advantages.

In one embodiment, the electronics system is mounted directly behind the lead shield 470 on, for example, nylon standoff 491. The electronics system is secured in place by, for example, five-sixteenth screw 492. Note the nylon standoffs, such as nylon standoff 491 allow for a thin air space between the electronics package volume 480 and the lead shield 470. The thin air space acts as an insulating buffer of air, reducing heat transfer to the imaging array system 450.

In one embodiment, the electronics package volume 480 has the following approximate dimensions: 0.27"×8.5"× 10.5".

The one-quarter inch screw 493 is available from McMaster-Carr of Los Angeles, Calif., part number 91253A106. Also available from McMaster-Carr, of Los Angeles, Calif., are the three-sixteenth screw 495, part number 92949A105; the knurled thread insert 490, part number 92394A112; the nylon standoff 491, part number 91145A129; and the five-sixteenth screw 492, part number 92949A107.

E. POWER SOURCES

Figure 13:
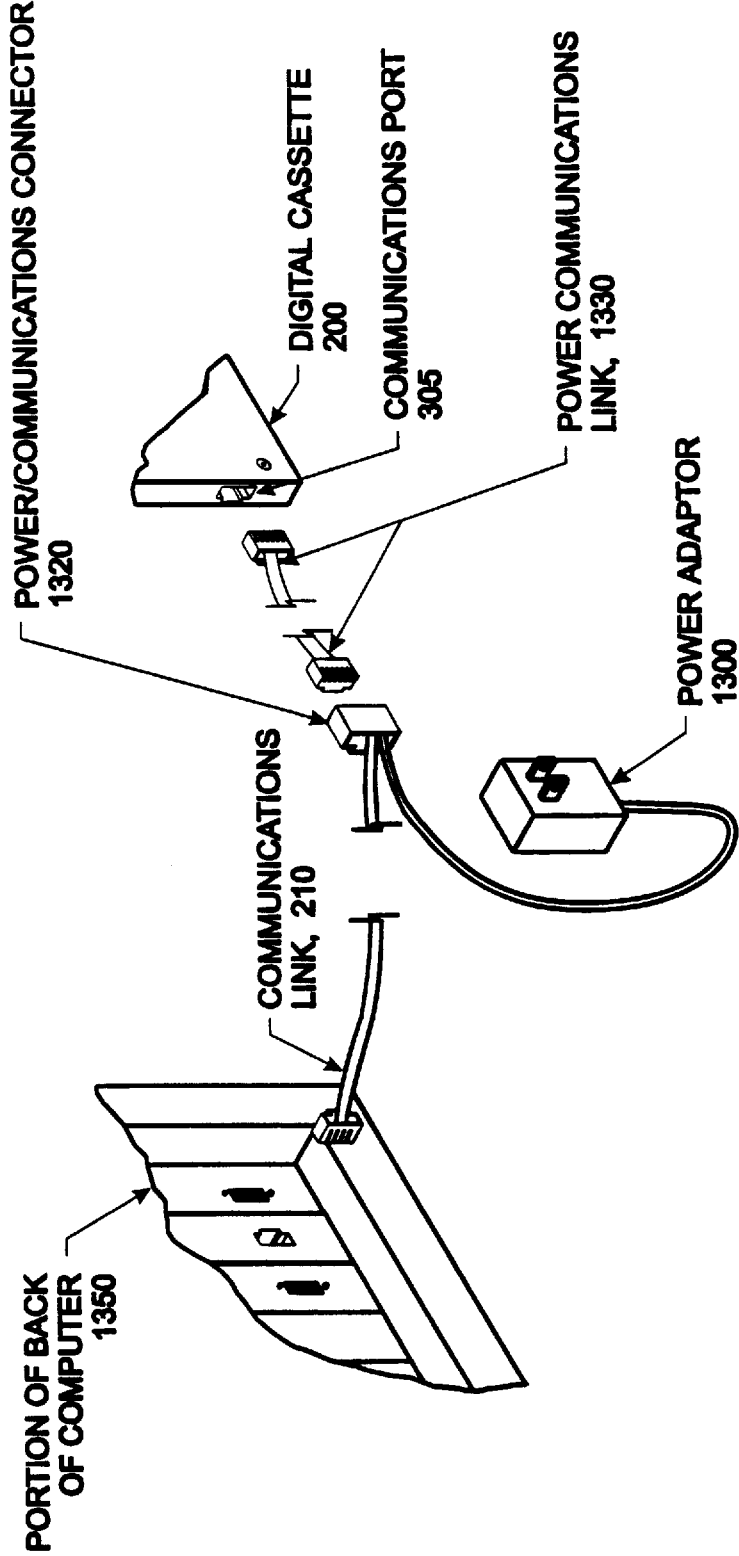
FIG. 13 illustrates a combined communications and power link to a digital cassette.
Figure 14:
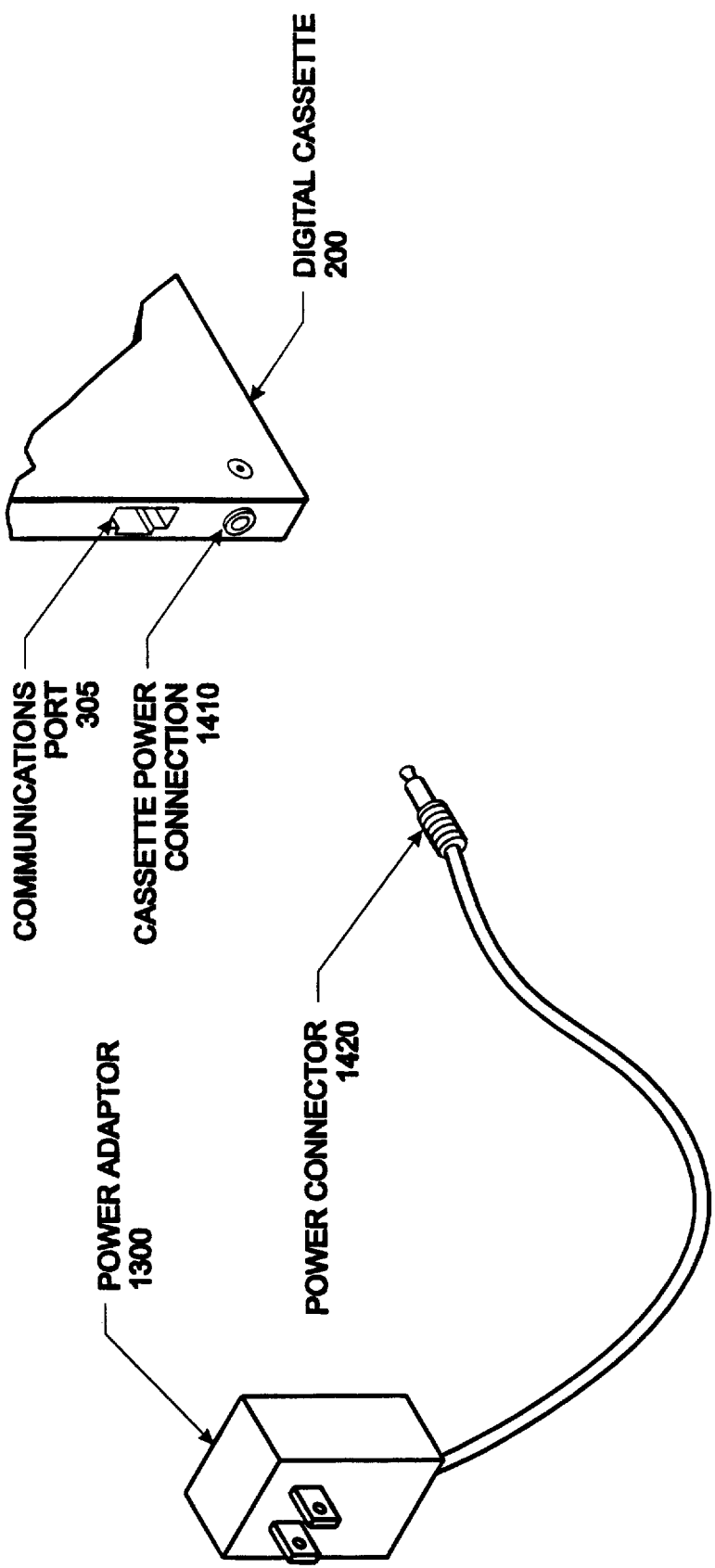
FIG. 14 illustrates an external power source for a digital cassette.

An important aspect of the digital cassette is the power supply for the electronics package volume 480. FIG. 13 and FIG. 14 illustrate possible solutions for the need to supply power to the electronics package volume 480.

FIG. 13 illustrates a combined communications and power link to a digital cassette 200. The digital cassette 200 is supplied power through the power communications link 1330. Power communications link 1330 supports a power supply for the digital cassette 200 and communications to the computer 220. The power/communications connector 1320 combines the communications link 210 and the power from the power adaptor 1300.

FIG. 14 illustrates an external power source for a digital cassette 200. The power adapter 1300 is connected directly to the cassette power connection 1410 on the digital cassette 200. The power connector 1420 connects the power adapter 1300 to the cassette power connection 1410.

Of course, the above two power supply methods rely on a direct cabled connection to the digital cassette 200. In one embodiment it is undesirable to have any direct cable connections to the digital cassette 200. Therefore in one embodiment, the digital cassette 200 includes a power supply, such as a battery. In another embodiment, digital cassette 200 is supplied with power by a battery connection that is attached to the x-ray machine 101. Periodic recharging of the internal battery can be performed by temporarily connecting the digital cassette 200 to a DC power source or by removing the digital cassette 200 to a remote charging station with a DC power source. However, generally it is preferable not to have to remove the digital cassette 200 from the x-ray machine 101 as this increase the risk of dropping the digital cassette 200 and thereby damaging it.

In another embodiment, the DC power required by the electronics package volume 480 is derived from the computer 220's internal power supply and combined in the communications link 210.

F. DIGITAL CASSETTE AND THE COMPUTER COMMUNICATIONS

Figure 15:
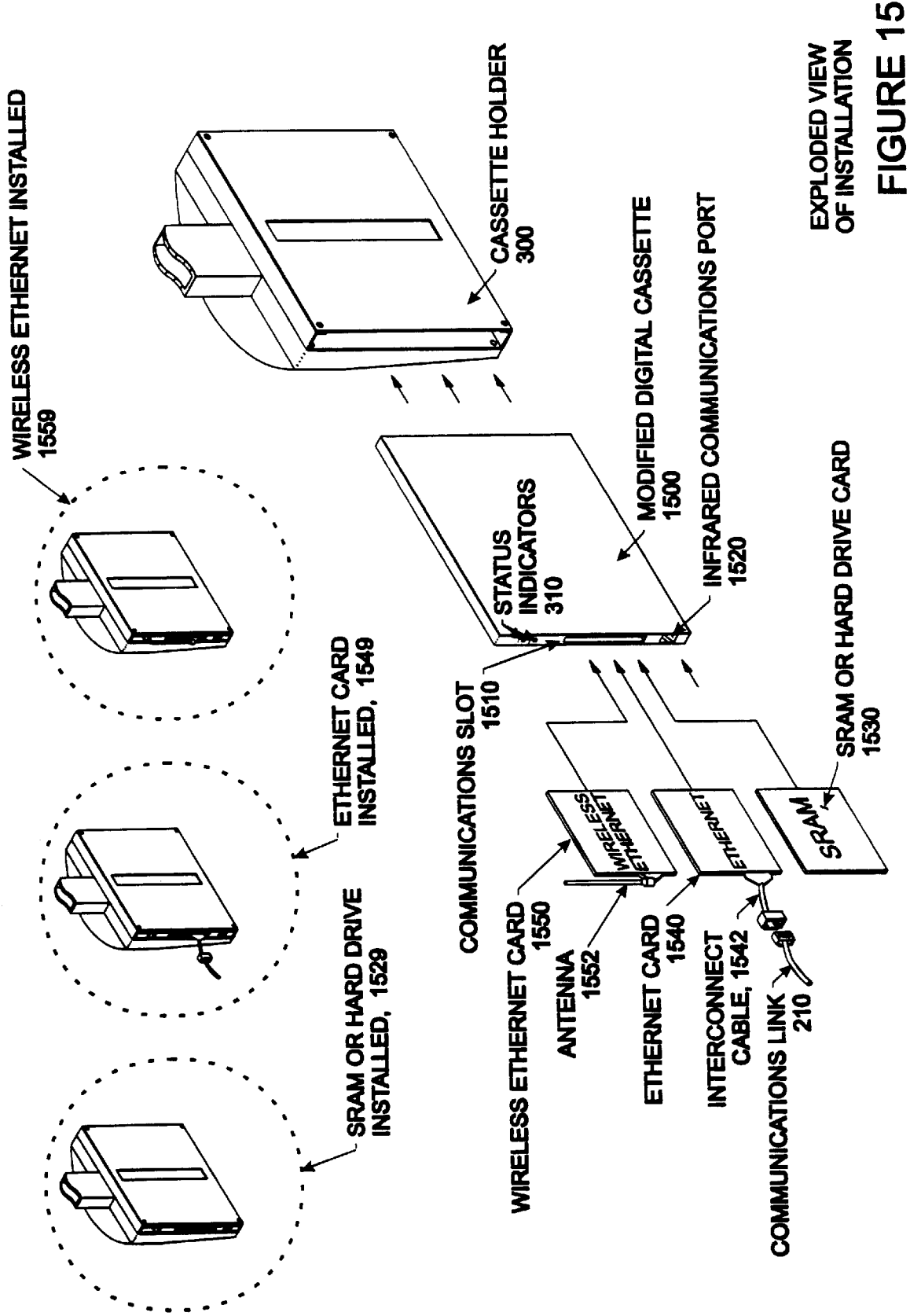
FIG. 15 illustrates a number of communications methods for communicating with a digital cassette.
Figure 16:
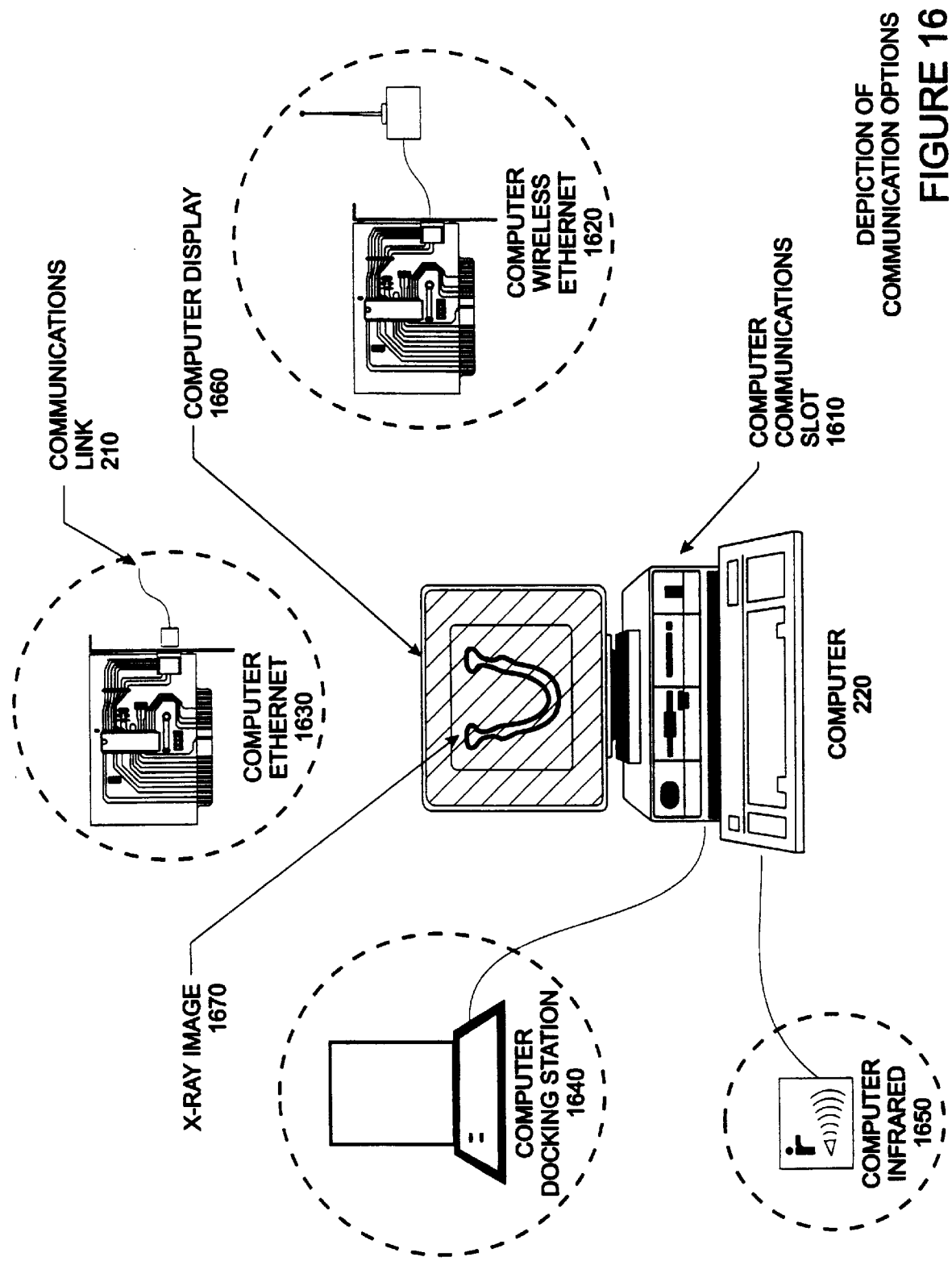
FIG. 16 illustrates a computer and a number of communications devices for communicating with a digital cassette.

FIGS. 15 and 16 illustrate a number of different communications solutions for digital cassette 200. It is important to note that the digitally captured images will contain a great deal of information. For example, an 8"×10" image may have 200 dots per inch and have eight bits of resolution per pixel. This results in an image that is over three megabytes. It is desirable to communicate the information from the digital cassette 200 to the computer 220 as quickly as possible.

One embodiment provides the standard cabled connection between the digital cassette 200 and the computer 220. This is shown in FIG. 3. In another embodiment, in order to reduce development costs, the electronics package volume 480 supports an industry standard communications slot 1510, for example, the PCMCIA or PC-card standard. In this embodiment a type-2 PCMCIA communications slot 1510 is integrated into the electronics package volume 480 and the back housing 420. The PCMCIA communications slot 1510 facilitates the installation and removal of PCMCIA cards. As more advanced PCMCIA cards become available, upgrading the digital cassette 200's communications links to the computer 220 becomes a simple matter of replacing the PCMCIA card and upgrading the software on the digital cassette 200.

In one embodiment, a PCMCIA ethernet communications adapter is incorporated in the digital cassette 200. That is, an ethernet card 1540 can be placed in the communications slot 1510. The ethernet card 1540 communicates via an interconnect cable 1542 to the communications link 210. The ethernet card 1540 is shown installed in the modified digital cassette 1500 in the ethernet card installed view 1549.

Using a standard network communication protocol, such as ethernet, allows any computer 220 on the same network to communicate directly with the digital cassette 200. Other network communications topologies could be used such as FDDI or ATM or some other high bandwidth format.

In another embodiment, a wireless ethernet card 1550 can be inserted into communications slot 1510. The wireless ethernet card has an antenna 1552 that communicates with the computer 220. In one embodiment, this configuration is particularly useful because no cables are required for the communications link 210. Having a wireless connection makes inserting the modified digital cassette 1500 into the cassette holder 300 a simpler process and eliminates any problems associated with routing a communications cable from the computer 220 to the modified digital cassette 1500.

The wireless ethernet card 1550 is shown installed in the modified digital cassette 1500 in the wireless ethernet installed view 1559.

In another embodiment, a memory card such as a static RAM or hard drive card 1530 can be inserted in the communications slot 1510. The digital image would then be stored in the static RAM or hard drive card. This is shown in the SRAM or hard drive card installed 1529 view. The memory card allows the modified digital cassette 1500 to store the digital image directly in the memory card. The memory card can then be removed from the modified digital cassette 1500 and inserted in the computer 220. Thus, the memory card embodiment obviates the need for a communications cable and reduces the complexity of the internal electronics in the modified digital cassette 1500. Further, the memory in the memory card can be used directly by the modified digital cassette 1500 for processing of the digital images. The disadvantage of this embodiment is that the host computer does not have direct access to the modified digital cassette 1500. The modified digital cassette 1500 then independently captures and stores one or several digital x-ray images on the SRAM or hard drive card 1530.

In another embodiment, an infrared communications port 1520 is incorporated into the modified digital cassette 1500. The infrared communications port is particularly useful where cabling is problematic and other wireless solutions do not work well.

FIG. 16 illustrates the computer 220 communications system for communicating with the digital cassette. The computer 220 can include a computer communications slot 1610 such as a PCMCIA slot. The PCMCIA communications slot 1610 would be able to accept similar cards to that of the modified digital cassette 1500. For example, a PCMCIA communications slot 1610 in the computer 220 could accept the SRAM or hard drive card 1530 used in the modified digital cassette 1500. A PCMCIA communications slot 1610 can also be used with a second ethernet card similar to the ethernet card 1540 or a similar wireless ethernet card. In another embodiment, the computer 220 includes a card for communicating on ethernet such as the computer ethernet 1630 solution. In another embodiment, the computer 220 includes a wireless ethernet card such as a computer wireless ethernet 1620 communicating with wireless ethernet card 1550. In another embodiment, the computer 220 can include a computer infrared 1650 solution. The infrared solution will allow the computer 220 to communicate with an infrared communications port 1520.

In another embodiment, computer 220, can include a computer docking station 1640. The computer docking station 1640 would accept the modified digital cassette 1500. After an x-ray image was captured in the digital cassette the operator 230 removes the modified digital cassette 1500 from the x-ray machine 101. The modified digital cassette 1500 is then placed in the computer docking station 1640. The computer docking station provides the communications electronics to communicate the digital image stored in the modified digital cassette 1500 to the computer 220. In another embodiment, the computer docking station also provides a recharge feature for the digital cassette 200 where digital cassette 200 includes batteries. However, as noted with the memory storage device embodiment, the computer docking station 1640 solution does not allow the computer 220 to communicate directly with the digital cassette while the images are being captured. However, in another embodiment, the computer docking station 1640 solution also includes an infrared or wireless port for infrared port communications link between the computer 220 and the modified digital cassette 1500.

The modified digital cassette 1500 includes an internal memory storage system that stores the digital x-ray image. The modified digital cassette 1500 could rely on an internal rechargeable battery system as describe above. In one embodiment, the modified digital cassette 1500 would typically be stored in the computer docking station 1640. To capture a digital x-ray image, the operator 230 removes the modified digital cassette 1500 from the computer docking station 1640 and inserts the modified digital cassette 1500 into the cassette holder 300. After making the exposures, the operator 230 then removes the modified digital cassette 1500 and re installs the modified digital cassette 1500 into the computer docking station 1640. The computer docking station 1640 has connections for providing power to recharge the internal rechargeable batteries and to make a communications connection to modified digital cassette 1500 to download the captured digital x-ray images.

Computer display 1660, as part of the computer 220, displays the x-ray image 1670.

G. MECHANICAL ALTERNATIVES TO PROVIDE ADDITIONAL SPACE.

Figure 17:
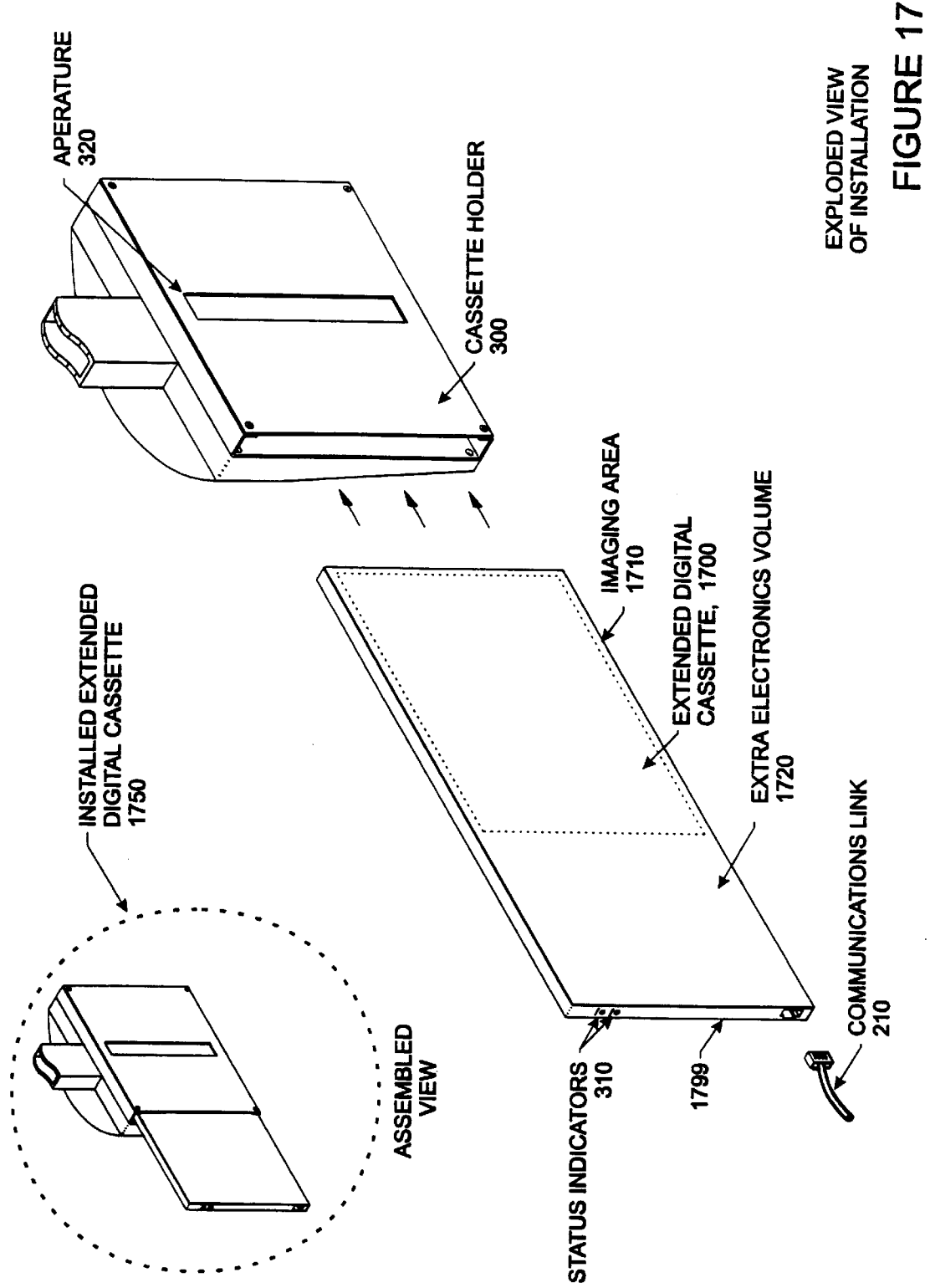
FIG. 17 illustrates an extended digital cassette.
Figure 18:
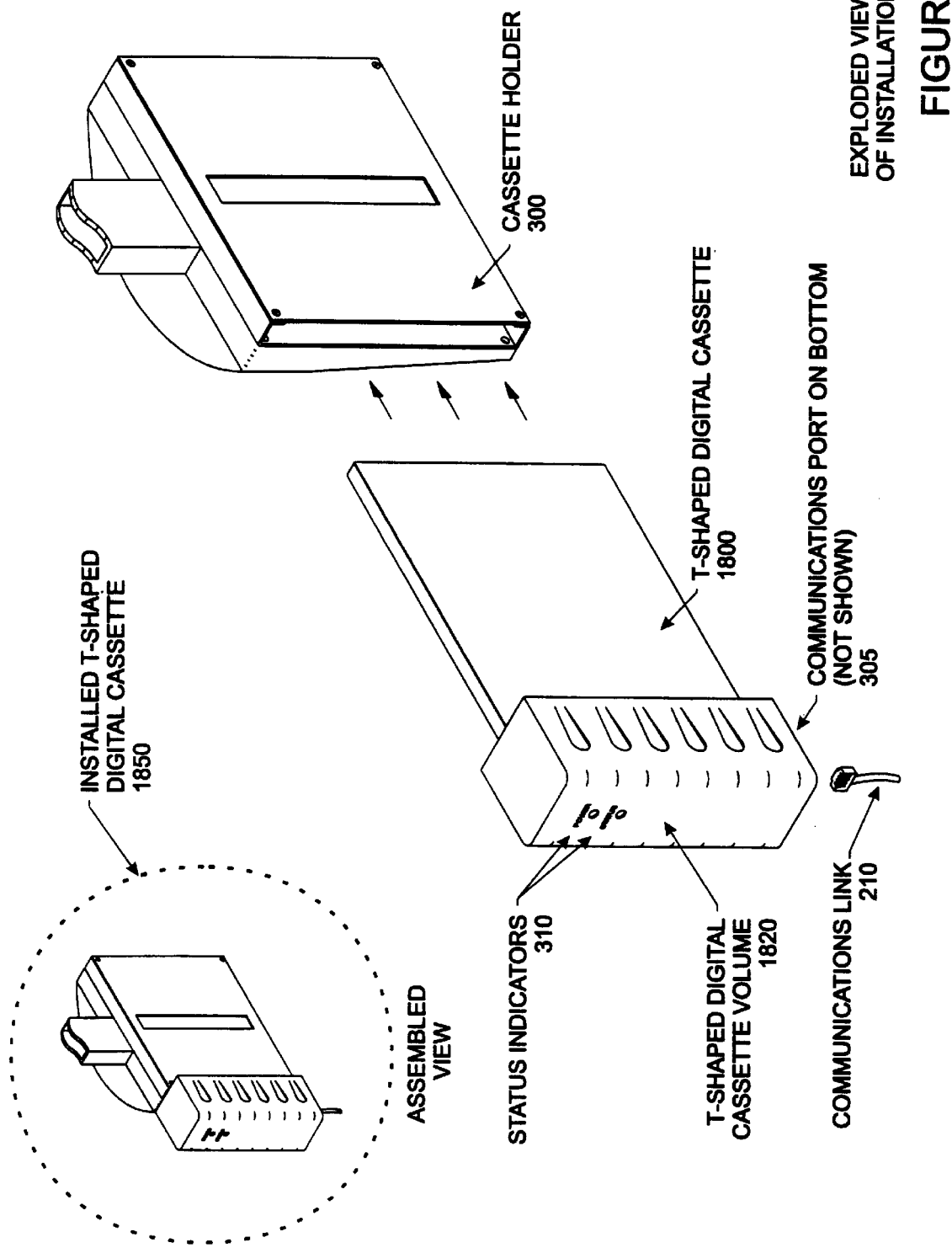
FIG. 18 illustrates a T-shaped digital cassette.
Figure 19:
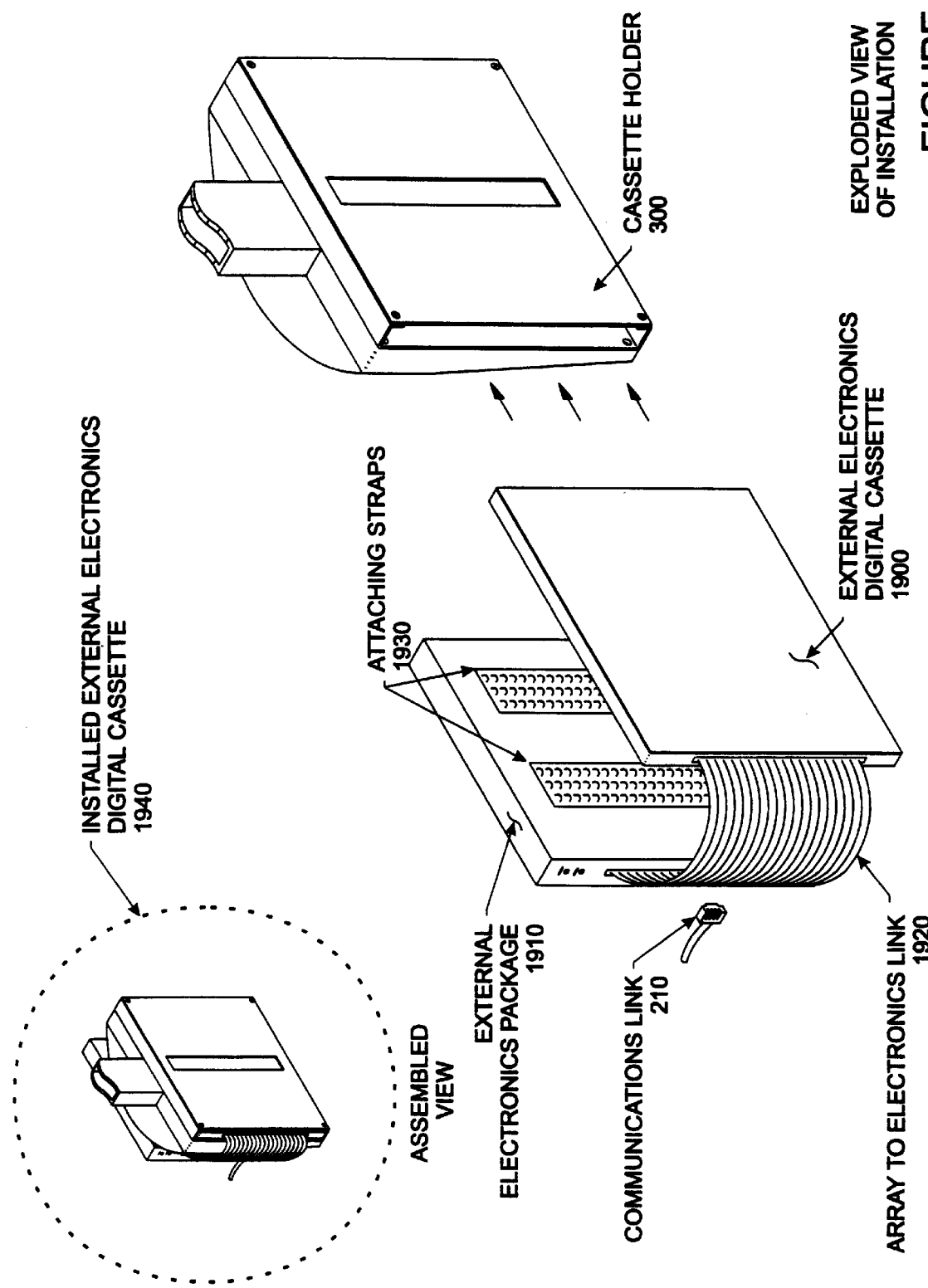
FIG. 19 illustrates an external electronics digital cassette.

FIG. 17, FIG. 18, and FIG. 19 illustrate alternative embodiments of the digital cassette 200 that allow for additional space within the cassette housing.

FIG. 17 illustrates an extended digital cassette as noted above. The extended digital cassette 1700 has an extra electronics volume 1720 within the housing. The imaging area 1710 stays in front of the aperture 320. The extra electronics volume 1720 can house additional electronics or a power supply, for example. Note the installed extended digital cassette 1750 view has the extra electronics volume 1720 extending out of the cassette holder 300.

Of course, one disadvantage of the extended digital cassette 1700 is that it does not have exactly the same form factor as a standard film cassette 199. However, because the height and depth of the extended digital cassette 1700 complies with standard film cassette 199, the extended digital cassette 1700 can be used in most cassette holders 300.

One advantage of the extended digital cassette 1700 is that it provides more convenient access to the end of the cassette 1799 once loaded into the x-ray machine 101, aiding the operator 230 in handling the cassette and viewing the status indicators 310.

FIG. 18 illustrates a T-shaped digital cassette. The T-shape digital cassette 1800 includes a T-shaped digital cassette volume 1820. As with the extended digital cassette 1700, the T-shaped digital cassette 1800 provides additional space for the electronics package volume 480. In one embodiment, the T-shaped digital cassette volume 1820 is detachable from the T-shaped digital cassette 1800. The T-shaped digital cassette volume 1820 then includes the memory and power supply such as a battery. The T-shaped digital cassette volume 1820 can then be walked over to the computer 220. The computer 220 can read the digital image from the T-shaped digital cassette volume 1820. In this embodiment, like the SRAM or hard disk drive solution, the T-shaped digital cassette 1800 need not be removed from the cassette holder 300 to communicate the image to the computer 220.

The T-shaped digital cassette 1800 does have the limitation where the T-shaped digital cassette volume 1820 would interfere with the x-ray machine 1O 1's operation. This may happen, where the cassette holder 300 translates the cassette within its housing during the exposure.

In another embodiment the external electronics digital cassette 1900 includes all the electronics for communicating with the imaging array system 450 externally from the external electronics digital cassette 1900. Thus, the external electronics digital cassette 1900 includes the imaging array system 450 and an array to electronics link 1920. Array to electronics link 1920 can be a flat cable or some other communications link. The external electronics package 1910 is attached to the outside of the cassette holder 300 or to somewhere else on the x-ray machine 101, for example. The external electronics package 1910 would include the electronics of the electronics package volume 480. FIG. 19 also includes a view of the installed external electronics digital cassette 1940. This embodiment allows for more space for the imaging array system 450. Additionally, the size and capacity of the support electronics can be configured as necessary. Generally, however, it is desirable to have the array to electronics link 1920 to be relatively short to insure data communications integrity. The external electronics package 1910 can be attached to cassette holder 300 by the attaching straps 1930. The attaching straps 1930 can be Velcro, for example. However, in other embodiments, other attaching mechanisms are used.

An important aspect of the alternative embodiments of FIG. 17, FIG. 18, and FIG. 19 and digital cassette 200 is that standard x-ray machines 101 need not be modified to accept any of these cassettes. Commercially, this means that each of these embodiments can be used in the large, installed base of standard x-ray machines 101.

Where a form factor larger than 8"×10" is needed, it may be advantageous to use unchanged components of the digital cassette of FIG. 4. The 8"×10" components would then have the active sensing area centered within the larger cassette form factor. This smaller sensing area in a larger cassette may be practical in cases where the peripheral areas of the x-ray image contain little anatomic information of interest.

H. ELECTRONIC SYSTEM

The following describes the basic electronic system of a digital filmless cassette. Many alternative embodiments of the following electronic system are within the scope of this invention. The electronic system, in one embodiment, fits entirely within the electronics package volume 480.

i. System Overview

The capture of a digital x-ray image begins with a trigger. A trigger is a signal that tells the digital cassette 200 to begin acquiring a digital x-ray image. A trigger can be either an external trigger received from a dedicated external trigger input such as may be part of the communications link 210 or from some other port on the digital cassette 200's housing. In one embodiment, an external trigger from the x-ray machine 2002 can be generated from the x-ray machine 101. For example, a button press on x-ray machine 101 can correspond to the external trigger from the x-ray machine 2002. The external trigger can also be generated from computer 220. Computer 220 generates a trigger initiated from, for example, the operator 230. The computer 220 using the communications link 210 communicates the trigger to the electronic system.

The digital cassette 200 can also be self triggering. That is, when the electronic system detects light being received by the imaging array system 450, then an internal trigger will be generated.

What is important is that the trigger is processed by the interrupt controller 2062 to start the capture of a digital x-ray image.

To capture a digital x-ray image, the imaging array system 450 and the electronics system acquire a frame of the digital image and transfer this frame to the RAM 2030. A frame is a single snapshot taken with the imaging array system 450. A frame is an image generated by incident x-ray light causing the illuminating screen 440 to glow in the visible light spectrum. The sensor pixels in the imaging array system 450 are sensitive to light and turn the light into an electrical charge which the pixels store. This charge is read from the pixels by using the address generator 2016 and the read out electronics 2012. When a specific sensor pixel's address is sent to the imaging array system 450, that pixel's charge is transferred to the read out electronics 2012. The read out electronics 2012 converts the pixel's charge into a digital number, called a pixel value, that represents the amount of charge that was stored and hence, how much light fell on that pixel.

In one embodiment, the pixel values are temporarily stored in the frame buffer 2014 before sending them to more permanent storage in the RAM 2030. In one embodiment, the pixel values will need to be reordered since sequential order is not the most convenient method of reading pixel values from the imaging array system 450.

In another embodiment, frames will be processed to improve their quality. In one embodiment, the CPU 2050 performs the image quality improvement under software control. In another embodiment, the image processing 2094 circuitry performs this image improvement. In one embodiment, the frame processing takes place as the frame is transferred from the frame buffer 2014 to the RAM 2030. In one embodiment, processing includes compensating for spot defects (dead pixels) and line defects (rows or columns of dead pixels) in the imaging array system 450, adjusting individual pixel values to compensate for variations in sensitivity, and equalizing pixel values in the frame to improve dynamic range or other image characteristics. In another embodiment, the final digital image is derived from a single frame.

In one embodiment, input/output circuit 2060 controls the interface communications link 210. CPU 2050 provides general control for the electronic system. ROM 2035 includes the software necessary to run the digital cassette 200. Compression 2090 is an optional circuit that will compress a digital image, or frames, for improved efficiency of transmission to the computer 220. Compression 2090 greatly reduces the amount of information that would be transferred to computer 220. The compression circuit also reduces the storage requirements on the computer 220 and possibly in the digital cassette 200. In one embodiment the compression 2090 can use one of a number of compression schemes, such as JPEG. In one embodiment the compression 2090 uses specialized hardware that is readily available that implements one of these compression schemes. In another embodiment, the CPU 2050 performs a compression directly under software control.

The captured image can be tagged with additional information as noted above. For example, the date, the image serial number, the digital signature, and other information can be included with the digital image. In one embodiment, the additional information is stored in a non-volatile read-write memory 2037, such as flash memory.

The encryption circuit 2092 provides security and a way to authenticate the image. The encryption can be performed by dedicated hardware components or via software control in the CPU 2050. Encryption circuit 2092 is optionally included in digital cassette 200 for encrypting at least a portion of the image or tag information.

Non-volatile read-write memory 2037 may be used in place of or in addition to RAM 2030 and ROM 2035. Non-volatile read-write memory 2037 may be optionally decoupled from the digital cassette, such as SRAM or hard drive card 1530.

Clock generator 2080 generates clocking signals for the digital cassette 200.

Power supply 2085 powers the electronic components of the digital cassette 200.

Bus 2020 communicates information among the various components of the electronics system.

The input/output circuit 2060 is responsible for communicating the digital image to the computer 220. Computer 220 stores the digital image and displays it for the operator 230.

I. ARRAY SUBSYSTEM

The array subsystem 2010 is an important and unique part of the digital cassette 200. The array subsystem 2010 includes the imaging array system 450, the read out electronics 2012, and the address generator 2016. In one embodiment, the array subsystem 2010 includes a frame buffer 2014, as described below.

i. The Imaging Array

From an electronics perspective the imaging array 2100 can be thought of as a two-dimensional image sensor. As noted above, physically the imaging array 2100 should fit within a standard x-ray film cassette 199 form factor. In one embodiment the imaging array 2100 has spatial resolution of 150 spots per inch and a usable dynamic range of at least fifty decibels (about eight bits).

In one embodiment, the imaging array 2100 includes hydrogenated amorphous silicon (a-Si:H). The a-Si:H is deposited as a thin film on glass and allows thin film transistors (TFTs) and sensors to be manufactured on extremely large substrates (in excess of fifteen inches diagonally). This technology is analogous to the creation of flat panel displays.

One such a-Si:H array is available from Xerox PARC of Palo Alto, Calif. The imaging array 2100 includes a number of gate lines which select individual pixels in the imaging array 2100 and a number of data lines 2120 that output the values of the select pixels.

For various form factors of a digital cassette 200, different imaging array 2100 sizes may be needed. Define $n_{gate}$ as the number of gate lines 2110 and $n_{data}$ as the number of data lines 2120. Thus the imaging array, 2100 has $n_{data}$ by $n_{gate}$ separate light sensitive pixels (sensor cells). These pixels are formed at the intersection of the gate and data lines. Each pixel is generally square and has dimension of $l_{pix}$ by $l_{pix}$. Thus, the size of an imaging array 2100 depends on $l_{pix}$, $n_{data}$, and $n_{gate}$. The dimensions of the imaging array 2100 are approximately $n^{gate}$ by $l_{pix}$ by $n_{data}$, horizontal by vertical. In one embodiment, there is a fixed overhead of approximately a half an inch on all sides of the imaging array 2100 required by the data and gate lines.

Numerous arrays are available from Xerox, for example. In imaging array 2100 from Xerox $l_{pix}$=127 microns, $n_{gate}$=1920, and $n_{data}$=1536. This provides dimension of approximately 9.6"×7.7" and has a resolution of approximately 200 spots per inch. In one embodiment, this is adequate for the core of the 8½"×10" standard film cassette 199.

Table 2 shows imaging array 2100 dimension for principle variance of the standard cassette form factors.

TABLE 2

| Desired Dimensions | n$_{gate}$ (length) | n$_{data}$ (length) | Actual Dimensions |
|---|---|---|---|
| 10 × 8 | 1920 (9.6) | 1536 (7.7) | 10.4 × 8.5 |

Of particular importance, is that each of these imaging arrays 2100 fit within the internal dimensions of the digital cassette 200's housing. Pixel 2150 is an enlarged view of the pixel from the imaging array 2100. Pixel 2150 contains a n-i-p diode sensor 2156 and a thin film transistor (TFT) 2155. Pixel 2150 is connected to three lines: gate-n 2130 line, the voltage bias line Vbias 2140, and data-n 2022 line. Vbias 2140 helps to prevent image lag (where pixels remember the previous image). In one embodiment, Vbias is two volts.

Each pixel 2150 is associated with a fill factor. In one embodiment, the imaging array 2100 has a fill factor of 37%. Fill factor determines the sensitivity of pixel 2150. The greater the fill factor, the more sensitive a pixel is and the less x-ray dosage required to obtain an adequate image. The fill factor is defined as a ratio of the area of the n-i-p diode sensor 2156 to the overall area of the pixel 2150. It is desirable to have a greater fill factor than 37%.

In one embodiment, pixel 2150 contributes the light it senses to the overall digital x-ray image as follows: Light falls on the n-i-p diode sensor 2156 and causes an electrical charge to build up there. TFT 2155 behaves as a switch. When the n-i-p diode sensor 2156 is charging, the TFT 2155 is off, allowing the charge to build on the diode. The amount of charge is directly proportional to the amount of light received by the n-i-p diode sensor 2156. To sense the built up charge, a voltage is placed on gate-n 2130 line. This turns on all of the TFTs attached to gate-n 2130 line. Thus, an entire column of TFTs are turned on simultaneously. Over the entire imaging array 2100, only one gate line is turned on at a time. When TFT 2155 is turned on, the charge stored in the n-i-p diode sensor 2156 is transferred through the TFT 2155 to the data-n 2022 line. Thus, although only a single line of the gate lines 2110 is active, all of the data lines 2120 will be active, reading the charge from all of the n-i-p diode sensors in the corresponding active column. The charge from the data lines 2120 are then read in parallel from both sides of the imaging array 2100. Note that the data lines 2120 are staggered where one line is sensed from the one side of the imaging array 2100 while the next line is sensed from the opposite side of the imaging array 2100.

The read out electronics 2012 performs the task of converting an analog signal from the data lines 2120 into digital data that can be further processed. Data lines 2120 are connected to a number of sample and hold circuits. In one embodiment the sample and hold 2160 includes a number of amplifiers and a multiplexor. The multiplexor provides a way to divide the number of data lines 2120 down to a more manageable number. For example, a 64 to 1 multiplexor 2161 is included in the sample and hold 2160. This reduces the number of A/D converters by a factor of 64. That is, the output of the 64 to 1 multiplexor 2161 is coupled to the input of the A/D converter 2180. Using a multiplexor in the sample and hold 2160, reduces the wiring problems associated with the array subsystem 2010. However, to minimize the time taken to capture a frame, the read out electronics 2012 should run faster than the imaging array system 450 can feed the image data.

Once the charge from a n-i-p sensor 2156 is stored in the sample and hold circuits 2060 the imaging array 2100 can be reset to read out the next column of data. The charge value held by each of the 64 sample and hold amplifiers is then multiplexed through to the A/D converter 2180.

In one embodiment, sample and hold 2160 and the multiplexor are combined in a single integrated circuit called an SVX chip. The SVX chip supports 128 analog inputs and two outputs. The SVX chip was developed by Lawrence-Berkeley Laboratory for silicon vertex detectors in high energy physics experiments.

The SVX chip must be connected to the very finely pitched data lines 2120. In one embodiment, the SVX chips are exposed and bonded to the edge of the imaging array 2100. The data lines 2120 are then wire bonded directly to the pads of the SVX chips. This is a very expensive and rather unorthodox manufacturing technique. In another embodiment, tab packaging is used. In this embodiment, the tab includes a SVX chip. One edge of the package fans out so that it can be attached directly to the surface of the imaging array 2100, thereby connecting the package to the data lines. A/D converter 2180 can be any one of a number of different A/D converters. In one embodiment, the A/D converters should be fast enough to process the data from the imaging array 2100 and provide enough accuracy for use in medical imaging. Accuracy can be defined in many ways, but the one important characteristic is the number of bits usable from the output from the A/D converter 2180. Although in one embodiment the imaging array 2100 has theoretical dynamic range of approximately sixteen bits, eight bits of resolution may be sufficient from the A/D converter 2180. However, other A/D converters can be used which provide a higher number of usable bits.

In one embodiment, because only every second data line of data lines 2120 are available at a given side of the imaging array 2100, the data generated by the output of the A/D converters on that side will be out of order. In one embodiment, the data must be rearranged to create the final correctly captured image.

ii. Address Generator

Figure 20:
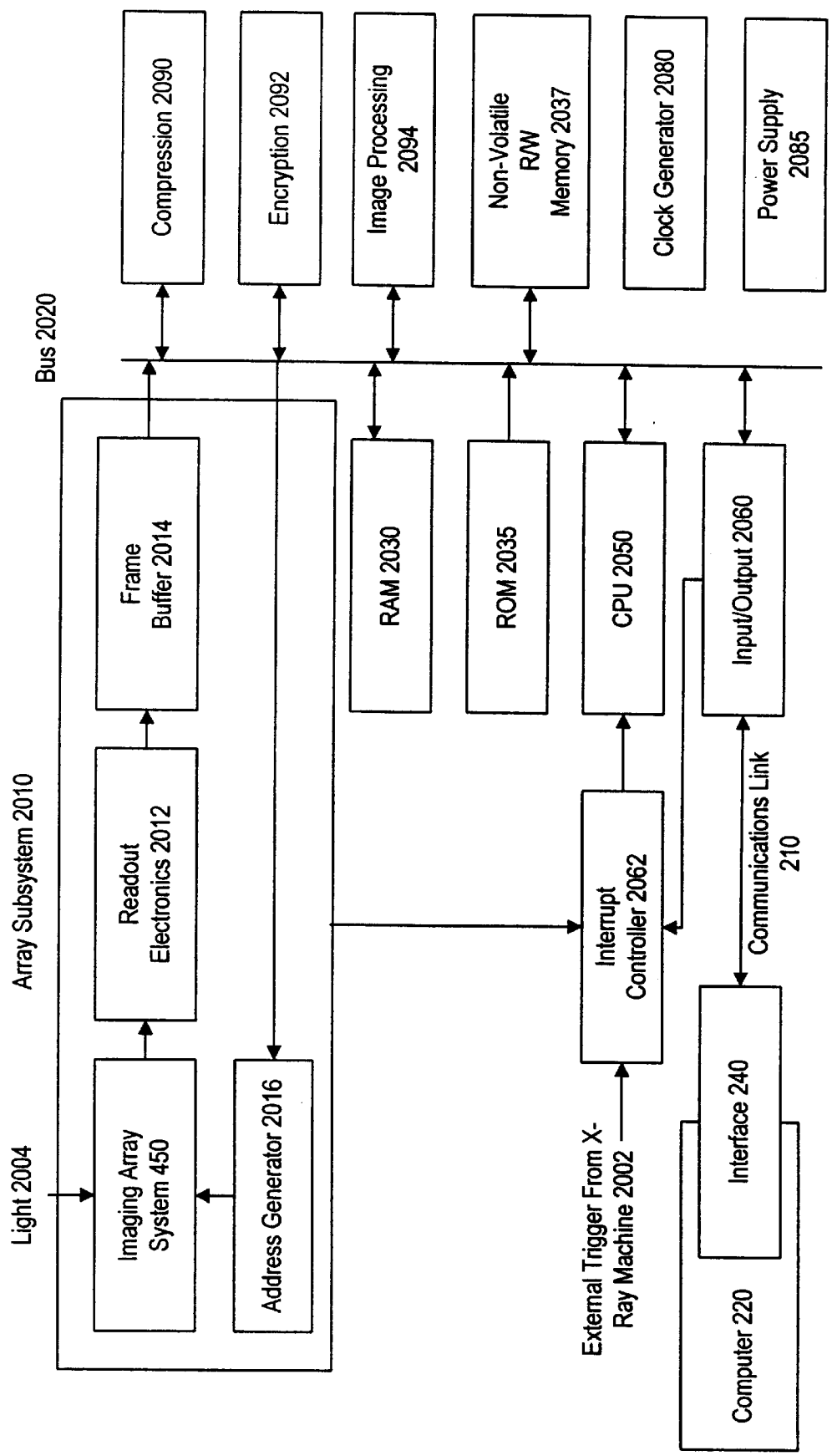
FIG. 20 illustrates the electronic system of a digital cassette.

Returning to FIG. 20, the address generator 2016 drives the gate lines 2120 to enable columns of pixels. Only a single gate line should be driven at a given time. Further, recall that only every second gate line appears at a given edge of the imaging array 2100. Thus, the address generator 2016 should drive a gate line at the top of the imaging array 2100 and then the adjacent gate line at the bottom of the imaging array 2100.

A gate line represents a substantial capacitance and resistance. A line is about ten microns wide and may be almost a foot long. In one embodiment, a relatively powerful gate drive circuit must be used to overcome this impedance and resistance quickly. In one embodiment, Supertex HV04 and HV06 drivers are used for this purpose. These drivers are parallel input, 64 output drivers for electrolumenesence applications.

Like the SVX chips, the gate drivers can be tab packaged onto the imaging array 2100. Of course, other types of connection mechanisms can be used to connect the gate driver circuits to the gate lines 2110.

iii. Electrical Behavior and Design Considerations of the Array Subsystem

The following discussion relates to the events that occur from when a given gate line is turned on until the analog data is processed by the A/D converter.

Generally, it is important to be able to capture images as quickly as possible. Since the time to capture a single frame will definitely be some fraction of a second, the amount of time the patient or doctor waits is not necessarily an issue. However, if we slowly scan from one side of the imaging array 2100 to the other side, there will be a systematic offset in the pixel values introduced because pixels read later will have had more time to capture light. Therefore, speed in capturing a frame is important. Similarly, the n-i-p diode sensor 2156 slowly loses its charge over time due to leakage current. Again, speed in capturing the image frames is important.

Figure 22:
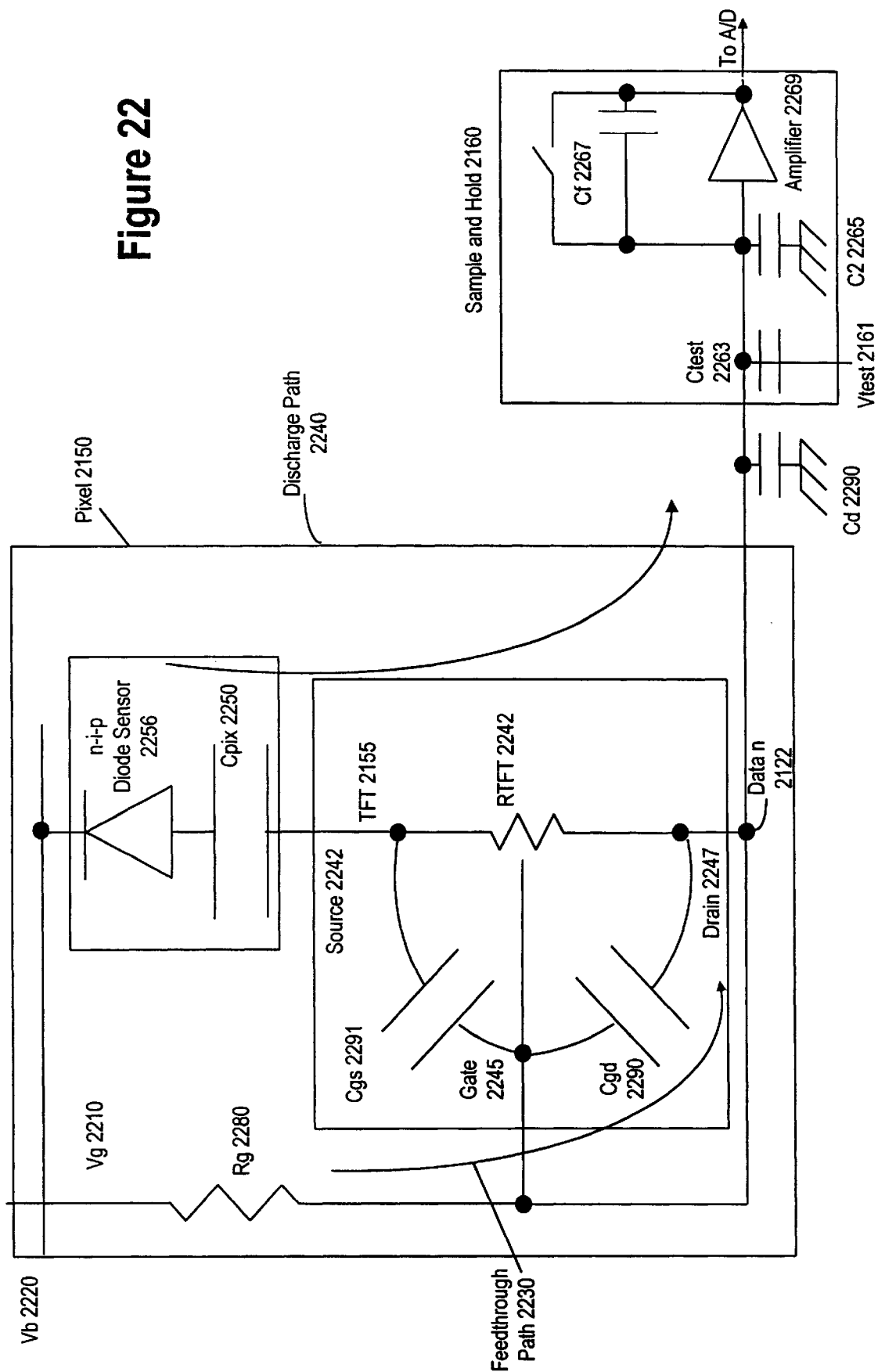
FIG. 22 illustrates an electronic circuit for a pixel and a sample and hold circuit.

FIG. 22 illustrate an electronic circuit of a pixel and a sample and hold circuit. In one embodiment, the gate drive voltage, Vg 2210 swings between plus or minus five volts. TFT 2155 is on when the gate bias is positive. In the FIG. 22, source 2242 is at the top of the TFT 2155 while the drain 2247 is at the bottom. However, these designations are somewhat arbitrary.

As mentioned above, TFT 2155 can be thought of as a switch. Because TFT 2155 is a transistor, the value of the TFT source-drain resistance, $R_{TFT}$, changes when the transistor is turned on and off. When TFT 2155 is off, $R_{TFT} = 10^{13}$ ohms. In one embodiment, when the transistor is on, $R_{TFT} = 4 \times 10^6$ ohms.

A connection between the n-i-p diode sensor 2256 to the data n line 2122 can be modeled as a single series resistor capacitor circuit. This is labeled as discharge path 2240. In such a circuit, current discharges at a rate exponentially proportional to the product of R and C values. The sensor capacitor Cpix 2250, in one embodiment of the invention, is 0.8 picofarads. When the TFT 2155 is turned off, the RC time constant is given by equation 1. Thus, current is lost relatively slowly when the transistor is off. When the transistor is on, the time constant becomes equation 2.

$$T_{off} = (10^{13} \Omega)(0.8 \text{ pF}) = 8 \text{ s} \quad \text{Equation 1)}$$

$$T_{on} = (4 M\Omega)(0.8 \text{ pF}) = 3.2 \text{ } \mu s \quad \text{Equation 2)}$$

Thus, when a transistor is on, the charge flows from the n-i-p diode sensor 2256 to the data n line 2122 relatively quickly.

The actual exponential charging equation for an RC series circuit is given by Equation 3 where $\tau$ is used for the time constant and t is time. To calculate the charge stored, one must integrate the current. Taking the integral of Equation 3 from 0 to t results in Equation 4. From Equation 4, one can calculate that it takes approximately five RC time constants to transfer 99% of the charge stored in the n-i-p diode sensor 2256. Thus, the time to discharge a pixel $T_{PIX}$, can be calculated from Equation 2 and Equation 4. For one embodiment this is approximately sixteen microseconds.

$$I_{out} = I_{in} e^{-\frac{t}{T}} \quad \text{Equation 3)}$$

$$I_{out} = I_{in} T [1 - e^{\frac{-T}{t}}] \quad \text{Equation 4)}$$

However, there is a second path from the gate line Vg 2210 through the parasitic capacitance $C_{GD}$ 2290 to the data n line 2122. This path is marked as feedthrough path 2230. Associated with this path is another time constant given by Equation 5.

$$T_{ft} = R_g C_{gd} \quad \text{Equation 5)}$$

Figure 23:
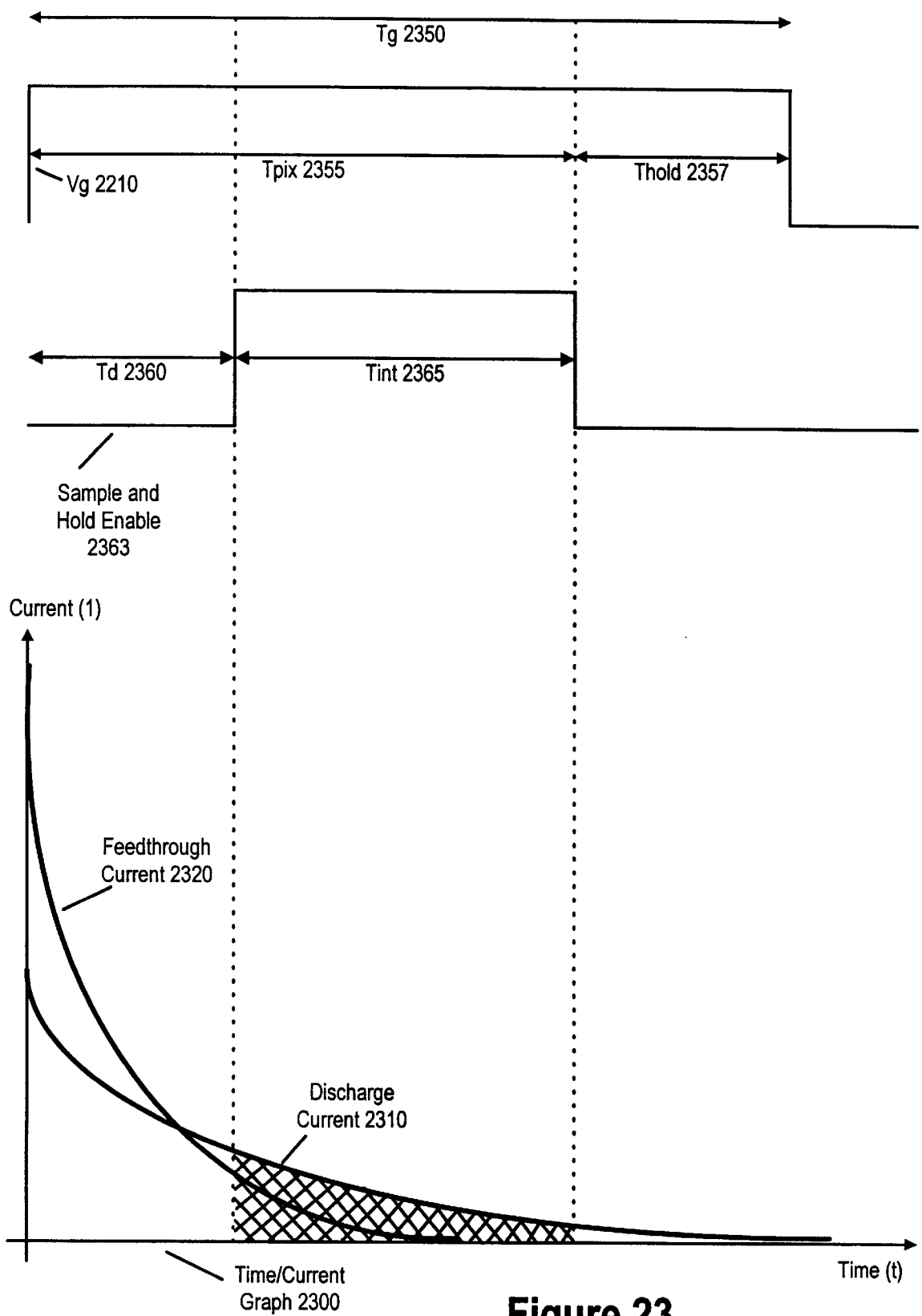
FIG. 23 illustrates the time characteristics associated with a pixel electronic circuit.

FIG. 23 illustrates the time characteristics associated with a pixel. That is, FIG. 23 illustrates the discharge characteristics of the pixel 2150 and the timing required to correctly read the pixel charge.

In one embodiment, the voltage on the gate line Vg 2210 is greater than the voltage stored in the n-i-p diode sensor 2156. Thus, in order for the array subsystem 2010 to read out the values stored on the pixel 2150, the feedthrough time constant, $\tau_{FT}$, must be smaller than $\tau_{ON}$. In this case, an SVX chip can be enabled after a slight delay during which the feedthrough current 2320 will have decayed so that it contributes only a proportionally small value to the output voltage.

Again, the feedthrough path 2230 introduces an error current onto the data line. Thus, the feedthrough current is large enough to overload the sample and hold (SVX chip) and result in an incorrectly read pixel value. To reduce this error, a delay Td 2360 is introduced between the time Vg 2210 rises and when the sample and hold enable 2363 is enabled. While the SVX chip is enabled, it integrates the current received from the data n line 2122 and stores the result on its feedback capacitor, $C_F$ 2267.

Given that the SVX chip is enabled only from $T_D$ 2360 to $T_D + T_{INT}$, the charge accumulated through an RC circuit is given by Equation 6. This is the integral of equation 3 evaluated from $T_D$ 2360 to $T_D + T_{INT}$ 2365. For the feedthrough path 2230, $\tau$ is $\tau_{ft}$. For the discharge path 2240, $\tau$ is $\tau_{on}$. The total charge sensed by the SVX chip will be the sum of the charge contributed by the feedthrough current 2320 and the discharge current 2310.

$$Q_{out} = Q_o \left( \exp \frac{-T_d}{T} \right) \left[ 1 - \exp \frac{T_{int}}{T} \right] \quad \text{Equation 6)}$$

The feedthrough current 2320 will be the same regardless of the amount of light sensed by the pixel 2150. Thus, given fixed values for $T_D$ 2360 and $T_{INT}$ 2365, the contribution of the feedthrough current 2320 can be determined by reading the pixel 2150 when no light is being sensed. However, it is important that $T_D$ 2360 is large enough that the SVX chip is not overloaded, or that its dynamic range is not reduced significantly. For accuracy, the integration time $T_{INT}$ 2365, should be as long as practical, but will be limited by the amount of time that can be budgeted for reading out each pixel given the desired frame read out time.

Since all the data in a given column is processed in parallel, the time required to read an entire frame of the array can be estimated based only on the number of gate lines 2110 and $T_{PIX}$. Thus, equation 7 provides a time to acquire an entire frame. For additional safety, in one embodiment 64 microseconds rather than 16 microseconds can be used for $T_{PIX}$ 2355. However, 32 microseconds can also be used.

$$T_{frame} = n_{gate} \times T_{pix} \quad \text{Equation 7)}$$

Other secondary effects may affect the computation of the frame time including the following. The resistance of the gate line increases as the line grows longer, so more data lines will slow down the array. Further, several elements are not discussed in the equations above, these include the resistance of the data line and the gain and capacitance of the SVX chip; these will change the results by a small amount.

Since speed depends only on the number of gate lines 2110, it matters a great deal whether the gate lines 2110 are along the short or the long side of the imaging array of the imaging array system 450. Since the SVX chips are relatively expensive, the cost of the hardware, in one embodiment, is traded off against the speed of capturing a frame. That is, if there are more data lines 2120 than gate lines 2110, the array will be faster but cost more.

The speed of the A/D converters 2180 is independent of the imaging array 2100 but depends on the value of $T_{PIX}$2355. This is because each A/D converter 2180 must convert the 64 analog signals held by each half of an SVX chip, and the conversions must all happen before the next gate is turned on. Thus, this time is shown as $T_g$2350. $T_g$2350 is $T_{PIX}$2355 +$T_{HOLD}$2357. If we assume that $T_{HOLD}$2357 is 0 (worse case assumption), then the time allowed for one A/D conversion is given by Equation 8. Using a value of 64 microseconds for $T_{PIX}$2355, it is easy to see that a conversion must take place in one microsecond. Inverting this gives an A/D converter speed of one megahertz, which is quite reasonable with today's technology.

$$T_{A/D} = \frac{T_{pix}}{64} \qquad \text{Equation 8}$$

Another design issue is the speed with which the frame buffer 2014 can store the outputs of the A/D converters. The speed requirements are relaxed substantially by using parallel buffering. That is, multiple frame buffers reduce the complexity and delay of the multiplexors required to intertwine output from the A/D converters. Including this effect, the frame buffer 2014 speed can be modeled by Equation 9. Here, $N_{RAM}$ is the number of banks of Random Access Memory (RAM) working in parallel, $N_{SVX}$ is the number of SVX chips that feed the frame buffer 2014 (128 pixels per SVX chip), $T_{RAM}$ is the worse case write time into the frame buffer 2014, $T_{MUX}$ is the worse case propagation delay through an N:1 multiplexor. Solving for $T_{RAM}$ gives Equation 10. Assuming $N_{RAM}$ is 12 (1 bank of memory for each SVX chip) and $T_{MUX}$ is negligible, the values of $T_{RAM}$ are given in the last column of table 3.

TABLE 3

| Desired Dimensions | $n_{gate}$ | Max Frame Rate (Hz) | SVX Chips | RAM Speed (ns) |
| --- | --- | --- | --- | --- |
| 10 × 8 | 1920 | 8 | 12 | 500 |

The dynamic range The dynamic range is approximately $10^6$. This indicates that pixel values generated by the array subsystem 2010 that differ by only one part in a million in that the light 2004 actually differed by one part in a million. The important part is the random noise and systematic errors that are part of the system limit the precision of the pixel values. Thus, for dynamic range of $10^6$, all the digits after the sixth significant digit are invalid. $10^6$ also equates to a dynamic range of 120 db. Dynamic range can also be stated in bits. Since a 16 bit number can represent 65536 number, it has an inherent dynamic range of approximately 96 decibels.

The factor influencing dynamic range in the array subsystem 2010 before the A/D conversion process is noise. In one embodiment, the amplifier 2269 in the sample and hold 2160 (for example, a SVX chip), is a source of noise. In one embodiment, the dynamic range of the SVX chip is approximately 14 bits. Therefore, the A/D converter need not provide more than 14 usable bits. In practice however, a 12 bit A/D converter may be sufficient. In another embodiment, an 8 bit A/D converter will be sufficient. Of course the above analysis is dependent upon the fabrication technology for the imaging array system 450. As pixel sizes reduce, frame captures must be faster. Also, the $T_{PIX}$2355 is proportional to the area of the n-i-p diode sensor 2256. Further, smaller TFTs 2155 will reduce the feedthrough current 2320.

iv. The Frame Buffer

As mentioned above, a frame buffer 2014 can be optionally included in the array subsystem 2010. In one embodiment frame buffer 2014 includes RAM dedicated to the array subsystem 2010. Digital pixel values from the sample and hold 2160 circuits are stored in the frame buffer 2014, temporarily. This allows the pixel values to be read quickly as required by the rest of the electronic system in the digital cassette 200. The frame buffer 2014 also reads from all the SVX chips in parallel. This is described in greater detail below.

J. 8"×10" ELECTRONICS SYSTEM

Figure 24:
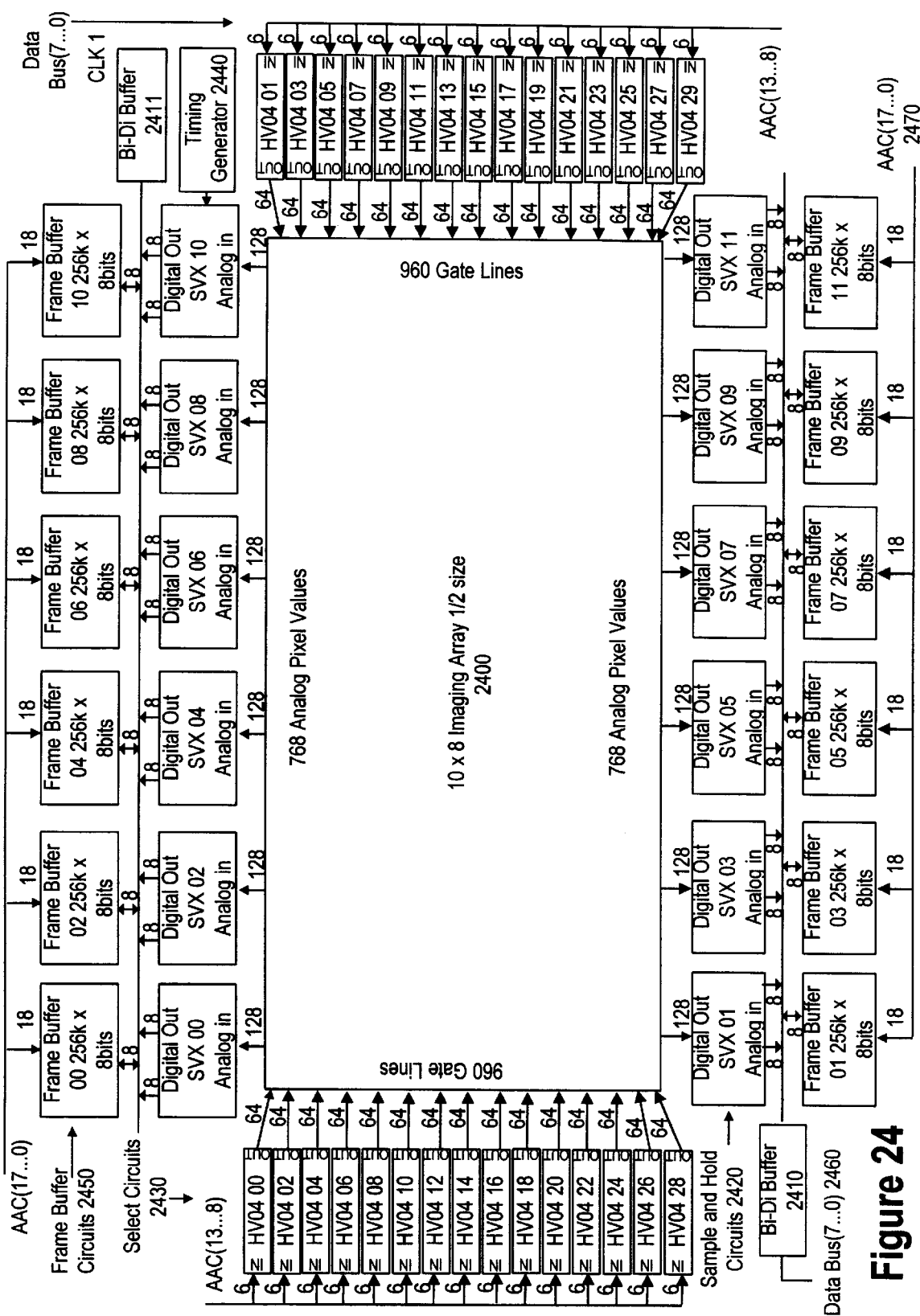
FIG. 24 illustrates an array subsystem.

FIG. 24 illustrates one embodiment of an array subsystem. FIG. 24 includes an 8"×10" imaging array 2400. The 8"×10" imaging array includes 960 gate lines per side and 768 data lines per side. Gate lines are driven by select circuits 2430. In one embodiment, these select circuits 2430 include HV04 gate driver chips. The HV04 chips perform 6 to 64 bit decodes. Thus, given a six bit address, a HV04 chip will select one of 64 output lines. Thus, to drive a single gate line on the 8"×10" imaging array 2400, a single HV04 driver is enabled and the appropriate address is asserted on its inputs. The analog pixels values are read out via the sample and hold circuits 2420 (12 SVX chips) shown on the top and bottom of the 8"×10" imaging array. Each SVX chip accepts 128 analog input lines and has two 8 bit digital lines out. Thus, the 12 SVX chips handle 1536 data output lines the 8"×10" imaging array 2400.

Sample and hold circuits 2420 require special timing clocks to enable them at the appropriate time as discussed above. The sample and hold circuits 2420 produce 128 8 bit outputs every $T_{PIX}$2355. Each SVX chip has output fed into a corresponding frame buffer chip. The frame buffer circuits 2450 include a number of frame buffer chips. The bi-di buffer 2410 and bi-di buffer 2411 allow the frame buffer circuits 2450 to optionally be coupled to the main data bus in the digital cassette 200. This allows the CPU 2050 to be coupled to the frame buffers. In one embodiment, the frame buffer circuits 2450, the select circuits 2430, the sample and hold circuits 2420, and the bi-di buffer 2410, and bi-di buffer 2411 are controlled by a hardware control system. This allows fast timing generation for the various components. In another embodiment, CPU 2050 directly enables the various components.

i. The Interrupt Controller

In one embodiment, the interrupt controller 2062 establishes priorities among the hardware components of the digital cassette 200 when they request attention from the CPU 2050.

Interrupt controller 2062 prioritizes the interrupts as follows, (from highest to lowest): array subsystem 2010 interrupts, input/output 2060 interrupts, and external trigger from the x-ray machine 2002 interrupts.

ii. The Clock Generator

The clock generator provides the timing for the electronic system. In one embodiment, a two megahertz clock drives the array subsystem 2010. The clocks for the CPU 2050 and other components will likely be much faster. All the clocks will be derived from the clock generator 2080.

iii. RAM

The RAM 2030, in one embodiment, will be a standard RAM as found in a personal computer, for example.

RAM 2030 will be used to store both programs and data in particular. In one embodiment, RAM 2030 includes 16 megabytes of memory.

iv. ROM

ROM 2035, in one embodiment, includes approximately one megabyte of memory. ROM 2035 will include not only the software for the digital cassette 200, but also such information as the specific digital cassettes' serial number.

v. Central Processing Unit

CPU 2050, in one embodiment, is a standard central processing unit such as an Intel 80386 central processing unit. In one embodiment, the central processing unit and the other components are organized in a standard personal computer architecture. This has the advantage of reducing the costs and providing a design environment similar to PCs.

vi. Input/Output and Communications

The input/output 2060 and the communications link 210 can be any of a number of standard or proprietary communications systems. For example, they may support standard serial, parallel, disk drive or network connections. For example, SCSI standard, ethernet, token ring, PCI bus, VME, FDDI, ATM.

K. SOFTWARE DESCRIPTION

Figure 25:
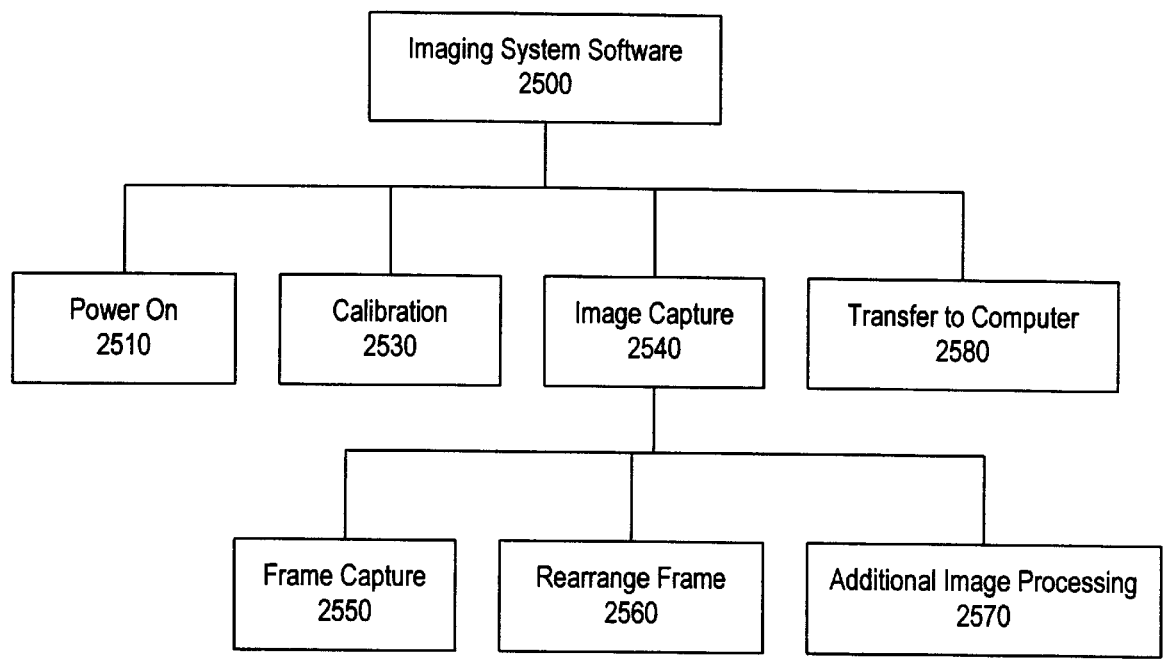
FIG. 25 illustrates a basic software system for a digital imaging system.
Figure 26:
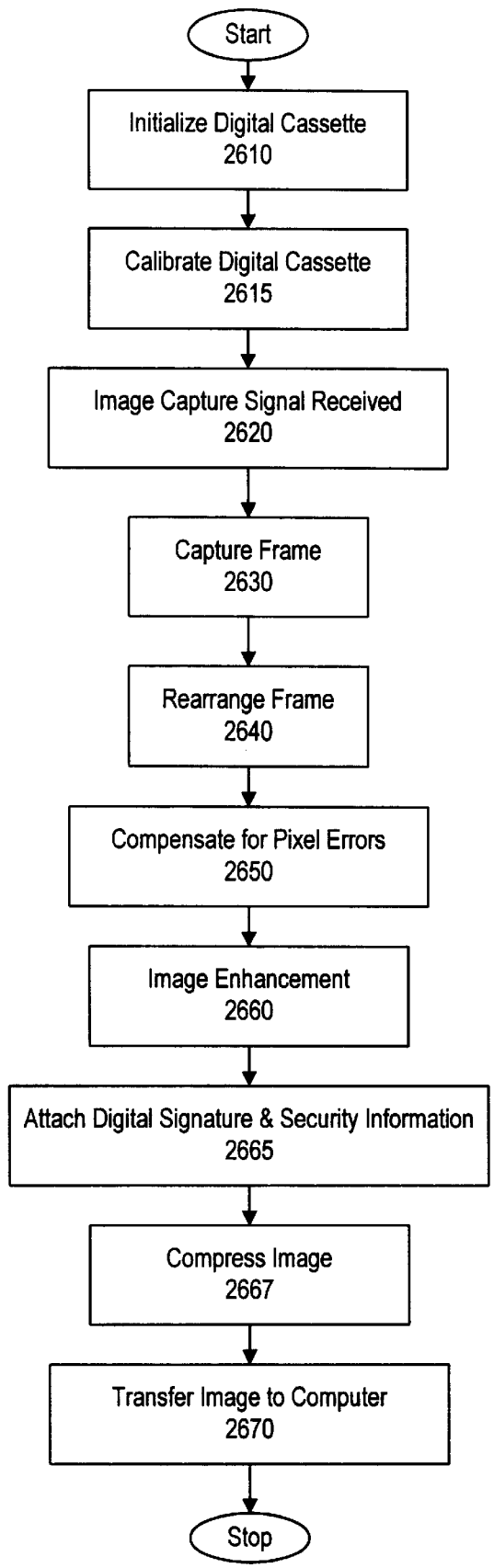
FIG. 26 illustrates an embodiment of a method of capturing and viewing an image.

FIG. 25 illustrates the structure of a software system for a digital cassette. The imaging system software 2500, of FIG. 25, can be implemented using the electronics of FIG. 20. The imaging system software 2500, in one embodiment, includes a power on block 2510, a calibration block 2520, an image capture block 2540 and a transfer to computer block 2580. FIG. 26 illustrates one embodiment of a method, using the system software, of initializing the digital cassette, capturing a digital image and transferring the image to the computer 220.

The power on block 2510 initializes the digital cassette 200. In one embodiment, the power on block 2510 is stored in ROM 2035. Power on block 2510 is responsible for setting global variables and the like. Power on block 2510 performs a self test of the digital cassette 200, including testing the communications link 210, if necessary. If the self test passes, power on block 2510 communicates this fact to the computer 220 and/or lights the corresponding status indicators 310.

i. Calibration

In one embodiment, the calibration block 2530 performs two related tasks. First, calibration block 2530 determines dead spots when the digital cassette 200 is manufactured and at other times as deemed necessary (e.g. during a servicing of the digital cassette 200). Secondly, calibration block 2530 determines the gain and the offsets of the digital cassette 200. This second task will be performed more often than the first task.

The calibration block 2530 compensates for any defects in the imaging array system 450. The imaging array system 450 can include a number of manufacturing defects. Theses defects can include defects in gate lines 2110, data lines 2120, and individual pixels, which impair or prevent columns, rows, or individual from working properly (called dead spots). Other defects can include differences in the offset and gain of pixels. In one embodiment, the gain of pixels drift over a continuous period of use.

In one embodiment, both tasks use an x-ray source 110. First a bright image is captured. In one embodiment, the bright image is captured with enough exposure to cause one (or some predetermined number) pixel to reach its maximum value. The dark image is taken without any light.

From the light image, the calibration block 2530 can detect the dead spots. In one embodiment, dead spots are pixels whose value falls below a predetermined value. The location of these dead spots can then be stored in ROM 2035 and compensated for during image captures.

The calibration block 2530 also compensates for offset and gain errors. Offset and gain errors occur when a pixel value is not zero in the dark image and/or not the maximum value in the bright image (e.g. 255). In one embodiment, we assume that the gain is linear. Therefore, the following equations illustrate how the gain and offset values for each pixel can be determined:

$$pix_{eq} = \text{gain} \times pix_{actual} + \text{offset}$$

$$pix_{max} = \text{gain} \times pix_{br} + \text{offset}$$

$$0 = \text{gain} \times pix_{dk} + \text{offset}$$

$$\text{gain} = \frac{pix_{max}}{(pix_{br} - pix_{dk})}$$

$$\text{offset} = -(\text{gain} \times pix_{dk})$$

The following pseudocode illustrates one embodiment of a method of determining the gain and offset for each pixel in the imaging array system 450. Note that the value 65408 is used as $pix_{max}$ rather than 255. 65408 is 255.5×256 and is used to shift the answers to the left (with proper rounding). This prevents the result of the division from being one and obviates the need to use floating point arithmetic in the digital cassette 200. The larger numbers can be compensated for elsewhere.

```
extern int *Gains;
extern int *Offsets;
Pixel_Calibration ( pix_t *br_img, pix_t *dk_img, int rows,
int cols)
{
    int *gain = Gains;
    int *offset = Offsets;
    for( int i - 0; i < rows; i++)
       for (int j=0; j < cols; j++, br_img++, dk_img++,
gain++, offset++)
       {
          *gain = 65408 / (*br_img - *dk_img);
          *offset = -(*gain * *dk_img);
       }
}
``` ii. Image Capture

Image capture block 2540 performs the image capture functions of the digital cassette 200. When the operator 230 has positioned the patient 180 in front of the x-ray source 110, the digital cassette 200 has been placed in the movable cassette holder 3190, the operator 230 can initiate the image capture feature by beginning the x-ray exposure. The image capture block 2540 then captures the digital x-ray image and stores it in the digital cassette 200s memory (or transfers it directly to the computer 220).

The image capture block 2540 includes a frame capture block 2550, a rearrange frame block 2560, and an additional image processing block 2570. In one embodiment, an image corresponds to a single frame. In another embodiment, an image is created from the average of a number of frames. In another embodiment, an image is created from a number of overlapping frames. What is important is that the pixel charges of the imaging array system 450 are turned into pixel values, these pixel values are captured and turned into the image.

(1) Frame Capture

The frame capture block 2550 retrieves a frame of pixel values from the imaging array system 450. In one embodiment, the frame capture block 2550 initiates a frame capture by enabling the frame capture hardware of the array subsystem 2010. The readout electronics 2012 retrieves the pixel values from the imaging array system 450 and stores them in the frame buffer 2014. In one embodiment, this completes the frame capture block 2550's function. In another embodiment, the frame capture block 2550 retrieves the captured frame from the frame buffer 2014 and stores the frame in RAM 2030.

(2) Frame Rearrange

As noted above, in one embodiment, the frame is needs to be reordered so that its rows and columns are consecutive. The rearrange frame block 2560 accesses the stored frame and reorganizes. The following code illustrates one way of reordering the frame so that the rows and columns are stored in order in memory.

```
/* returns address of row, col in frame buffer */
ptr_t Unmap_Frame_Buffer(int row, int col)
{
    // bit 0 in the row is odd or even data line
    // bit 18 in the addr selects frame buffer odd or even
    unsigned long addr = (row & 0x01) << 18;
    // bits 8-10 of the row form rest of FB select
    // slide bit 8 to bit 19
    addr |=(row & 0 x700) << 11;
    // The other 7 bits of the row slide up just
    // before FB select
    addr |= (row & 0xFE) << 10;
    addr |= col & 0x3FF // AND to be safe
    return (ptr_t) addr;
}
```

(3) Image Processing

The additional image processing block 2570 performs image processing on the frames and or the image.

In one embodiment, the additional image processing block 2570 compensates for dead spots and any gain and offsets needed for specific pixel values. The following pseudocode illustrates one method of compensating for dead spots and gain and offset errors. After the compensation, the frame represents at least a portion of the final image.

```
/* Initialized from ROM Table */
extern vecOf<int> BadRows;
extern vecOf<int> BadCols;
extern vecOf<point_t> BadPixels;
extern int *Gains;
extern int *Offsets;
int Equalize_Frame (pix_t *frame)
{
    foreach pix in frame
        pix = (Gains[pix] * pix + Offsets[pix]) >> 8;
    foreach r in BadRows
        Median_Filter_Row(frame,r)
    foreach r in BadCols
        Median_Filter_Col(frame,c)
    foreach p in BadPixels
        Median_Filter_Pixel(frame, p)
}
```

In one embodiment, the additional image processing block merges the frame into the image. This is discussed in greater detail below.

The additional image processing block 2570 may then perform additional image processing on the image. For example, the additional image processing block 2570 may perform histogram equalization on the image or some other image processing technique.

(4) Other Image Capture Processing

Image capture block 2540, in one embodiment, includes other processing blocks. For example, image capture block 2540 may include a security block and/or a compression block. The security block is responsible for associating security information, such as a digital signature, with the captured image. This is described in greater detail below. The compression block compresses the image before it is transferred to the computer 220.

iii. Transferring Images

Transfer to computer block 2580 configures the input/output 2060. The image is then transferred from the digital cassette memory (e.g. RAM 2030), via the communications link 210, to the computer 220, under the control of the transfer to computer block 2580.

iv. Initializing the Cassette, Capturing an Image, and Transferring the Image FIG. 26 illustrates an embodiment of a method of capturing and viewing an image.

At step 2610, the power on block 2510 initializes the digital cassette 200 as described above. Step 2610 can be executed in response to the digital cassette 200 being powered on, the computer 220 transmitting a reset signal, or a reset button being selected on the digital cassette.

At step 2615, the calibration block 2530 performs the necessary calibration steps, if any.

At step 2620, the digital cassette 200 receives the initiate image capture signal.

At step 2630, the frame capture block 2550 captures a frame.

At step 2640, the rearrange frame block 2560 rearranges a frame.

At step 2650, the additional image processing block 2570 compensates for pixel errors (dead spots, gain and offset errors).

At step 2660, the image capture block 2540 optionally performs additional image processing on the image, as described above.

At step 2665, the image capture block 2540 optionally attaches a digital signature to the image and encrypts at least a portion of the image. This is described in greater detail below.

At step 2667, the image capture block 2540 optionally compresses the image to reduce the bandwidth requirements of the communications link 210.

At step 2670, the transfer to computer block 2580 transfer the image to the computer 220 for viewing by the operator 230.

v. Transmitting an Image to a Second Location

Figure 27:
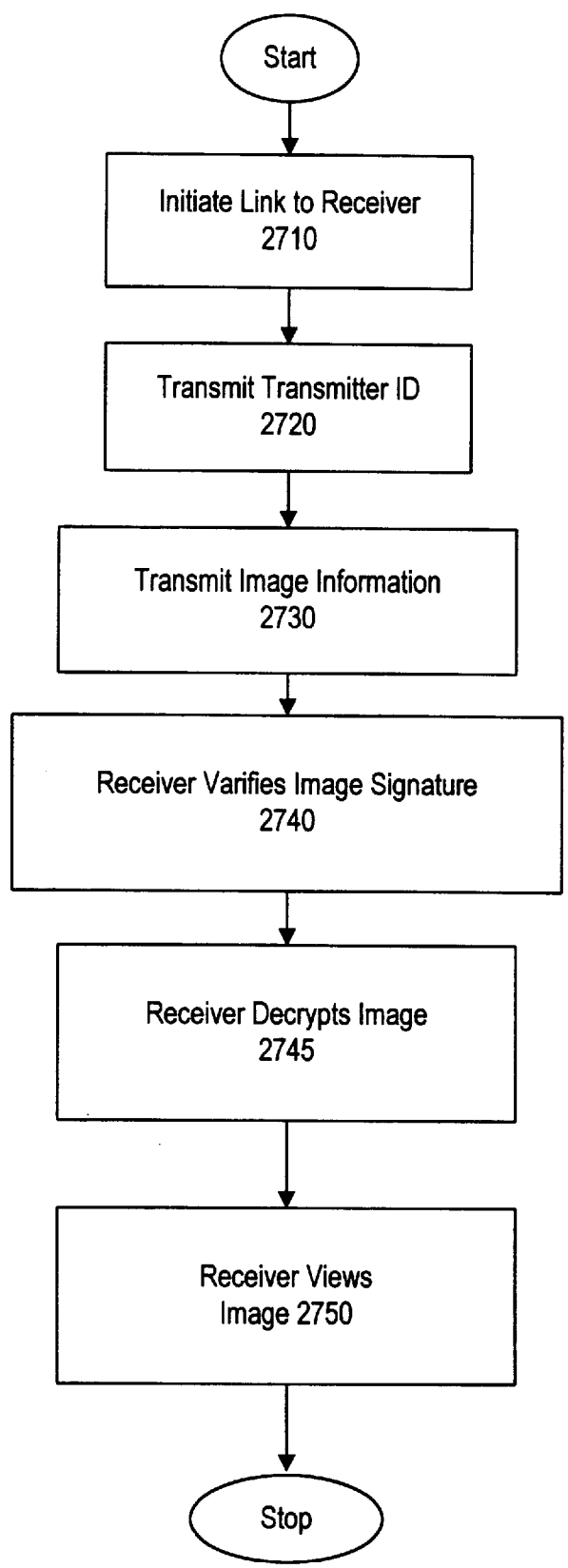
FIG. 27 illustrates a method of communicating a digitized x-ray image to an external location.

FIG. 27 illustrates one embodiment of a method of transferring the digital image captured by the digital cassette 200 to a second location. For example, the operator 230 may wish to communicate the digital image to an insurance company to begin processing of an insurance claim. Importantly, in one embodiment, the digital cassette attaches a digital signature to the image data and encrypts at least a portion of the image data. This allows, for example, greater patient information security and helps to prevent erroneous or fraudulent claims (e.g. using the digital signature, a claim submission using the same image for different patients can be detected).

Before describing FIG. 27 in detail, the encryption and the authentication capabilities of a digital cassette 200 is described. Encryption helps prevent unauthorized access to image data. Authentication helps prevent fraud.

In one embodiment, the digital cassette encrypts the image data. In one embodiment, a public key encryption scheme, such as the RSA encryption scheme, and/or a private key encryption scheme, such as DEA/DES encryption scheme, are used. In one embodiment, all, or a portion of, the captured image is encrypted by the digital cassette 200 before the image is transferred over communications link 210. The encrypted image can then be decrypted by the computer 220 before displaying the image. The encrypted image data can be securely transmitted to another computer for display.

In one embodiment, the computer 220 encrypts the data, rather than the digital cassette 200. However, it is important, in one embodiment, that the digital cassette 200 encrypts the data before transmitting it to the computer 220, because this embodiment provides greater security for the image data.

As noted above, digital images can be authenticated. For example, a digital signature can be associated with an image when the image is captured. A digital signature is encrypted information created using a secret key and authenticated with a public key. Therefore, digital cassette 200's authentication capabilities have an advantage over film based x-ray systems in that each digital x-ray image can be uniquely and easily identified. Therefore, for example, the same digital image cannot be submitted to the same insurance company for two different patients. The insurance company need only authenticate the digital signatures to find a fraudulent claim. The encryption scheme used to create the digital signature makes it very difficult to fraudulently create an authentic digital signature.

In one embodiment, a public key authentication system is used. In one embodiment, a digital cassette 200 includes a secret key, assigned at the time of manufacture, or assigned by, for example, an insurance company. In either case, the secret key should be securely transmitted to the digital cassette 200 and stored in non-volatile memory 2037 before the digital cassette 200 captures digital images. The secret key is used to create a digital signature from the tag information stored in the digital cassette 200. A corresponding public key is used to authenticate a match between the digital signature and the tag information (also sent with the digital signature).

In one embodiment, each digital cassette 200 has a unique identifier associated with it when it is manufactured (e.g. a serial number). The tag information can include the unique identifier and other information such as the date, the image number (corresponding to the number of images taken by the digital cassette 200), and/or some portion of the captured image. The tag information can include other information such as the identity of the patient 180, the doctor or dentist's insurance identifying number, and/or the operator 230's identity.

FIG. 27 illustrates one embodiment of a method of transferring the digital image captured by the digital cassette 200 to a second location. This embodiment can be implemented using the digital imaging system of FIG. 2 and a receiver computer such as a personal computer or main frame.

At step 2700, the digital cassette 200 establishes captures the image, creates the digital signature, and encrypts the image data. The encrypted image data is then transmitted to the computer 220.

At step 2710, the computer 220 (e.g. at a doctor's office) initiates a communications link between the computer 220 and a receiver computer (e.g. at an insurance company). This can be done, for example, using a modem or a dedicated communications link.

At step 2720, the computer 220 transmits its identifying information (e.g. doctor's name and id, digital cassette 200's information). This allows the receiver to access the corresponding public keys and/or private keys for that doctor and/or digital cassette 200.

At step 2730, the computer 220 transmits its the encrypted image data, the digital signature and the tag information for that image.

At step 2740, the receiver verifies the digital signature (image signature) using the public key for that doctor (digital cassette 200). The tag information within the digital signature is compared to the tag information sent with the image.

At step 2745, the receiver decrypts the image data.

At step 2750, the receiver can view the image data knowing that it is an authentic image and that it was transmitted to the receiver securely.

vi. Automatic Shut-Off

Figure 28:
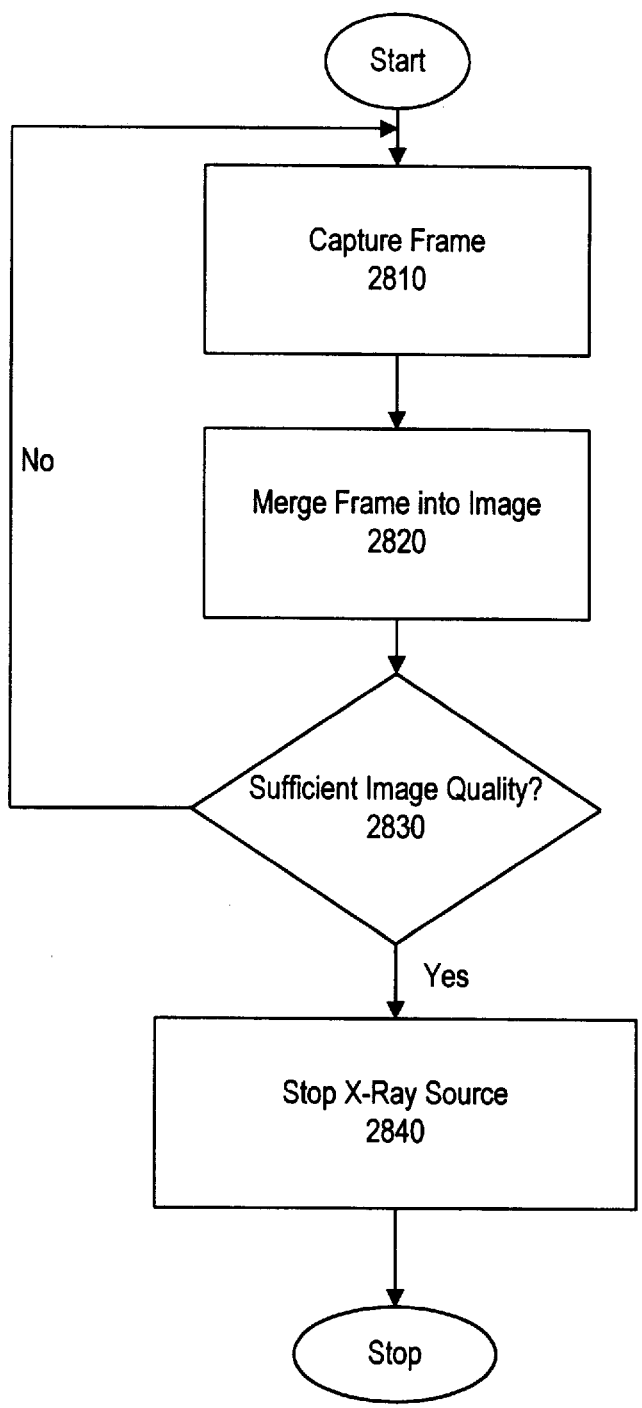
FIG. 28 illustrates one embodiment of a method of performing an auto shut-off in a digital x-ray capture system.

FIG. 28 illustrates one embodiment of a method of performing an auto shut-off in a digital x-ray capture system. In one embodiment, the digital cassette 200 and the computer 220 have control of the x-ray machine 101. In combination, the digital cassette 200 and the computer 220 can reduce the x-ray dosage to a patient by stopping, or reducing, the amount of x-rays from the x-ray source 110 when a sufficient quality digital image is captured.

Generally, the digital cassette 200 provides feedback to the computer 220 regarding the image that is being captured. The computer 220 uses the information to determine whether the x-ray source 110 can be turned off or reduced.

In one embodiment, a sufficient quality digital image is determined by the range of the pixel values in the digital image (the dynamic range). The dynamic range is determined from the maximum pixel value minus the minimum pixel value in an image. If the maximum pixel value is one and the minimum pixel value is zero, the digital image would only be represented by black and white pixels. In one embodiment, a sufficient dynamic range is determined for an image by the operator 230 (e.g. one hundred different gray levels between maximum and minimum values). In another embodiment, rather than dynamic range, a sufficient image quality is determined when a sufficient number of pixel values have reached a predetermined level (e.g. two hundred and fifty-five).

In one embodiment, importantly, an image is made from a number of merged frames. The frames are added together and averaged to form the image. The image quality can be tested as the frames are accumulated. When the accumulated frames reach the desired image quality, the x-ray source 110 is turned off.

At step 2810, a frame of an image is captured.

At step 2820, the frame is accumulated into the previously captured frames.

At step 2830, a test is made to determine whether a sufficient image quality has been achieved. (See above.) If the image quality is not sufficient, then step 2810 through step 2830 are repeated.

At step 2840, the image quality is sufficient, the digital cassette 200 can transmit a stop x-ray source 110 command, through computer 220 or directly to the x-ray machine 101. In another embodiment, the computer 220 or the digital cassette 200 only indicates to the operator 230 that the x-ray exposure can be stopped. Thus, in the embodiment, the computer 220 does not have to control the x-ray machine 101. Also communicated, in one embodiment, are suggested settings for time, amps and/or volts. In these embodiments, the digital cassette 200 provides exposure feedback in already installed x-ray machines 101 not previously designed to provide this type of information.

In one embodiment, the operator 230 sets the x-ray machine 101's amps, volts, and time for exposure. The digital cassette 200 can only stop the x-ray source before the time for the exposure elapses or can reduce the amps or volts. This prevents a failure in the digital cassette 200 or the computer 220 from increasing the x-ray dosage received by patient 180.

In another embodiment, the digital cassette 200 directly controls the x-ray source 110, without help from the computer 220.

L. PANORAMIC DIGITAL X-RAY CASSETTE i. Panoramic Basics

Figure 29:
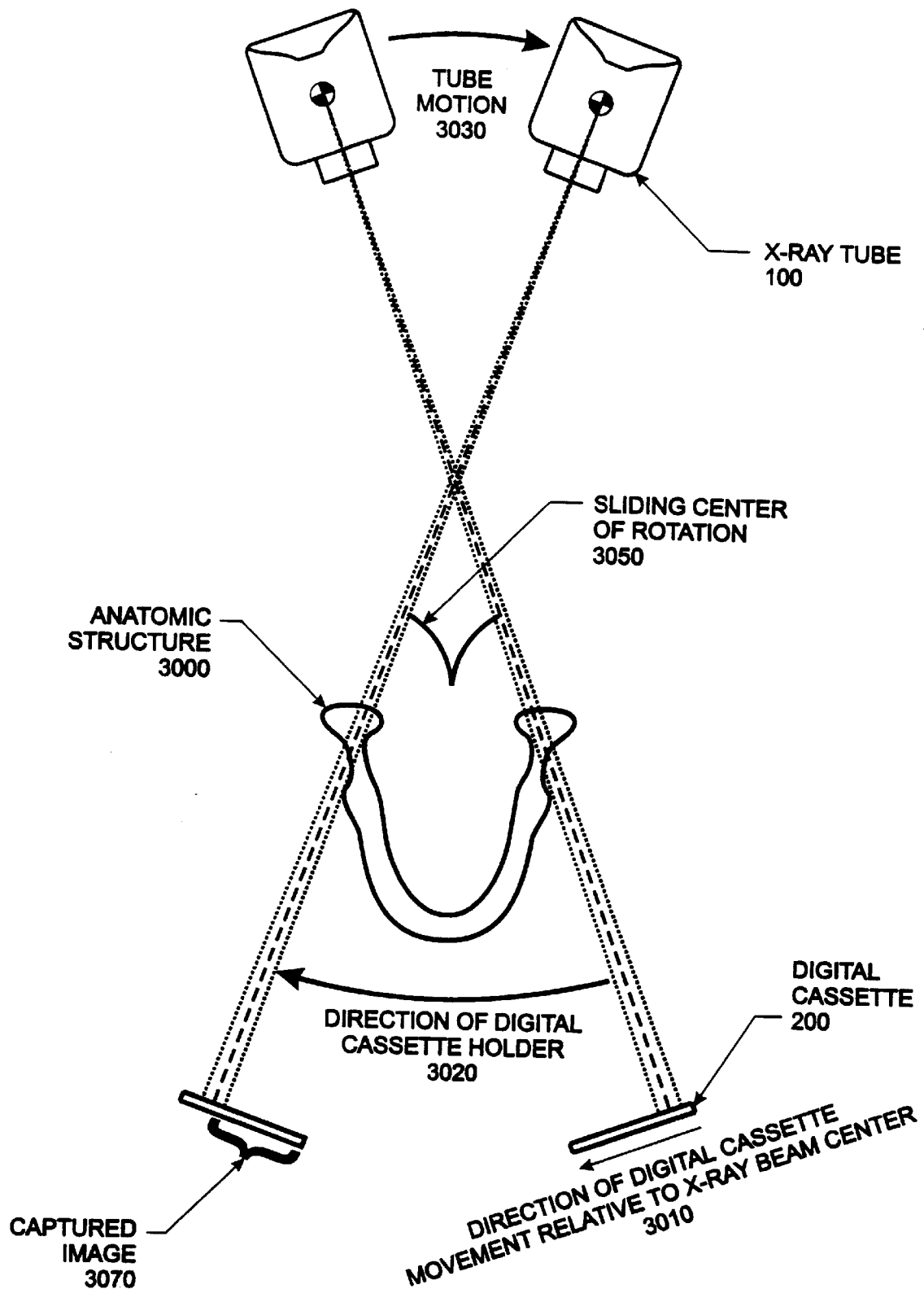
FIG. 29 illustrates the mechanics of taking a panoramic digital x-ray image.

FIG. 29 illustrates the mechanics of taking a panoramic x-ray image. Panoramic x-ray images are captured by moving a film cassette 199 past panoramic cassette holder 3109's aperture 320 while rotating the holder and tube about the sliding center of rotation 3050. The x-ray tube 100 and panoramic cassette holder 3109 rotate along the sliding center of rotation 3050, during an exposure, constantly realigning the tomographic slice to a new region of the anatomic structure 3000.

Importantly, panoramic images expose only a small portion of the film cassette 199 at a time, by sliding it past the narrow aperture 320.

ii. Panoramic Digital Cassette

In one embodiment, rather than using the standard film cassette 199, the digital cassette 200 is substituted.

The digital cassette moves in the panoramic cassette holder 3109 in the direction of the digital cassette movement relative to the x-ray beam center 3010. At the same time, the x-ray tube 100 is moving in the direction of the tube motion 3030. Additionally, the x-ray tube 100 and the panoramic cassette holder 3109 rotate about the sliding center of rotation 3050. The direction of the digital cassette holder 3020 is also shown in FIG. 30.

The panoramic projections create an anatomic cross-sectional view of the anatomic structure 3000. Again, importantly, the panoramic imaging sequential exposes, by small increments, the anatomic structure 3000 and also the digital cassette 200. The digital cassette 200 thereby captures an entire image.

iii. A Reduced Active Area Panoramic Digital Cassette

Figure 30:
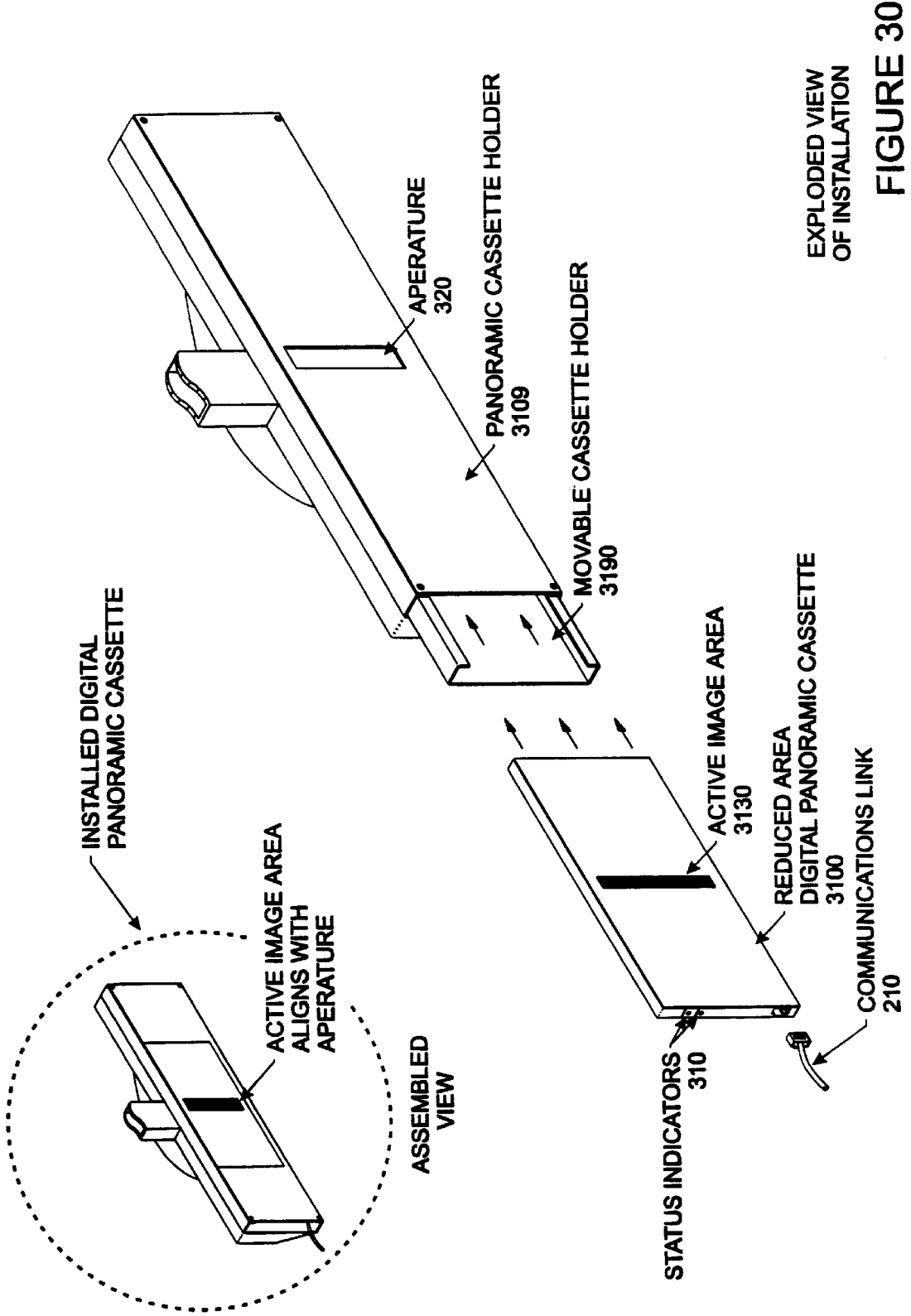
FIG. 30 illustrates a panoramic cassette holder and a digital panoramic cassette.

FIG. 30 shows a panoramic cassette holder 3109 and a reduced area panoramic digital cassette 3100. The panoramic cassette holder 3109 has a movable cassette holder 3190. The movable cassette holder 3190 moves a cassette across the aperture 320 during the exposure of the image. As mentioned previously, the reduced area panoramic digital cassette 3100 is a standard form factor digital cassette such as a 5"×12" or a 8"×10" cassette.

In one embodiment however, an active image area 3130 is much smaller than the entire cassette size. The smaller active image area 3130 substantially reduces the cost of the reduced area panoramic digital cassette 3100. The size of the imaging array system 450 can be greatly reduced to correspond to the active image area 3130. In such an embodiment, the active image area 3130 is held immediately behind the aperture 320 and the movable cassette holder 3190 is disabled from moving the reduced area panoramic digital cassette 3100. The reduced area panoramic digital cassette 3100 then captures frames during the exposure period and reconstructs a panoramic image representing the original motion of the movable cassette holder 3190.

One particular advantage of the reduced area panoramic digital cassette 3100 is that there is substantially more room within the housing to include specialized electronics, because the corresponding imaging array system panoramic imaging system 3250 is substantially smaller.

Important considerations in the reduced area panoramic digital cassette 3100 are that the individually captured frames must be reconstructed into a corresponding full size image, and the reduced area panoramic digital cassette 3100 should be prevented from moving while not having to modify, or only minimally modify, the panoramic cassette holder 3109. Remember, one important aspect of one embodiment of the invention is that it works relatively seamlessly in the installed base of x-ray machines 101. That is, no changes should ideally have to be made to the x-ray machine 101 to use not only a standard digital cassette 200 but also a reduced area panoramic digital cassette 3100 with an active image area 3130.

(1) Reduced Active Area Panoramic Cassette

Figure 31:
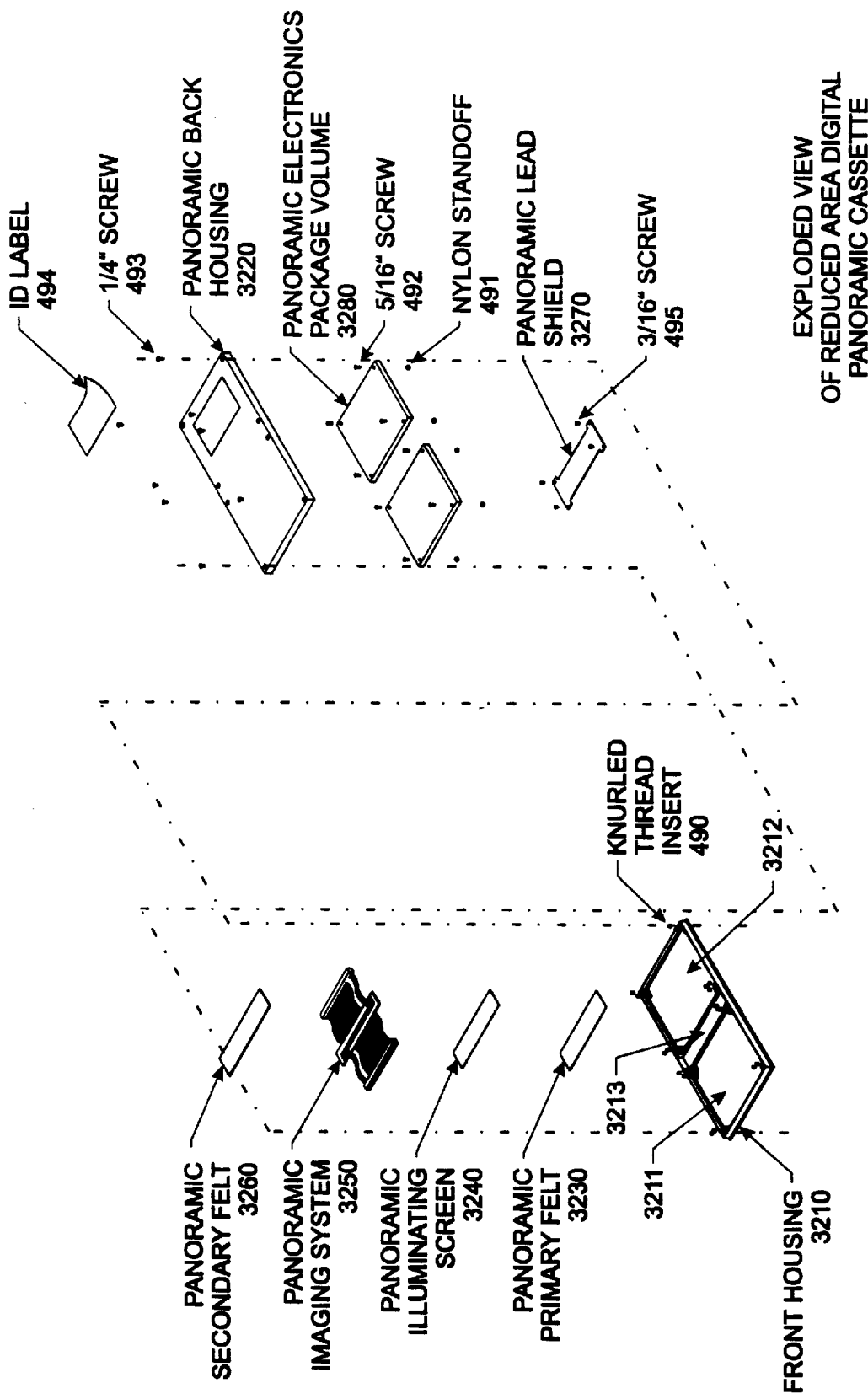
FIG. 31 illustrates a panoramic digital cassette.
Figure 32:
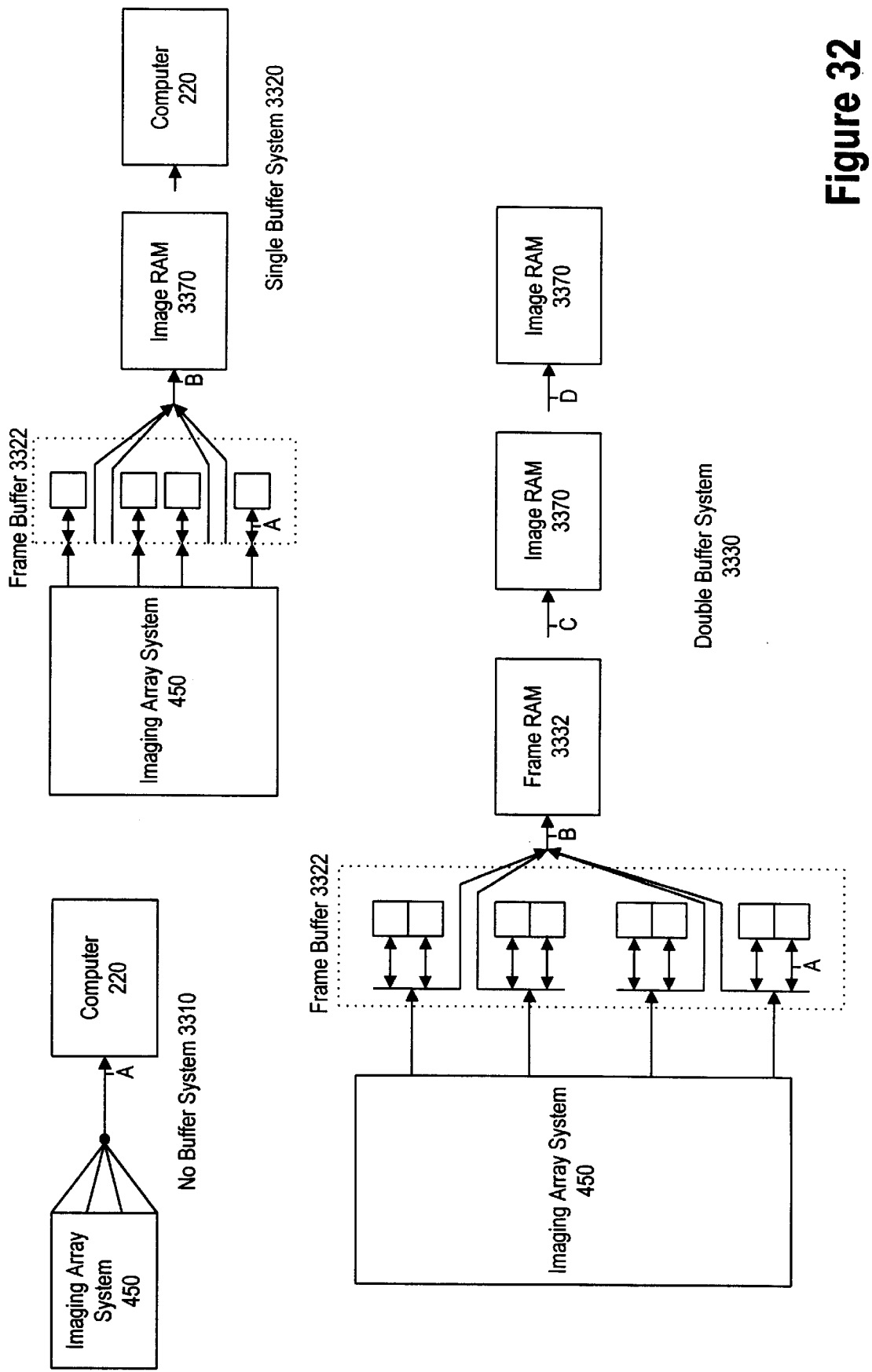
FIG. 32 illustrates a number of buffering systems for communicating a digital x-ray image to a computer.

FIG. 31 illustrates an exploded isometric view of a reduced area panoramic digital cassette 3100.

The components of a reduced area panoramic digital cassette 3100 are similar to that of the standard digital cassette 200. However, as shown the panoramic imaging system 3250 has an imaging array that is substantially smaller then the original imaging array system 450. In one embodiment, the active image area 3130 can be 0.2" wide. In this embodiment the panoramic electronics package volume 3280 can be much larger than in the standard digital cassette 200.

The reduced area panoramic digital cassette 3100, in one embodiment, includes a panoramic front housing 3210 and a panoramic back housing 3220. The panoramic front housing 3210 and the panoramic back housing 3220 have three distinct areas. The first area 3211 and the second area 3212 allow for larger panoramic electronics package volume 3280. The area 3213 is used to include the components of the panoramic imaging system 3250 as described below.

First a panoramic primary felt 3230 is inserted in the area 3213. Next, a panoramic illuminating screen 3240 is then inserted over the panoramic primary felt 3230. Next, the panoramic imaging system 3250 is laid on top of the panoramic illuminating screen 3240. Next, the panoramic secondary felt 3260 is laid on top of the panoramic imaging system 3250. Next, a panoramic lead shield 3270 is laid over the panoramic secondary felt 3260 and affixed to the panoramic front housing 3210 by, for example, three-sixteenth screw 495. Next, the panoramic electronics package volume 3280 can be inserted into the area 3211 and area 3212. The panoramic electronics package volume 3280 can be held down, for example, by five-sixteenth inch screw 492 and nylon standoff 491. Finally, in the panoramic back housing 3220 can be screwed down to complete the panoramic digital cassette. One quarter inch screw 493 can be used for this purpose. Next, the ID label 494 is applied to the panoramic back housing 3220.

A digital panoramic cassette can be created with other variations. For example, the panoramic imaging system 3250 has been placed in the center, or approximately in the center, of the panoramic front housing 3210 and panoramic back housing 3220. However, the area 3213 can be placed at either end of the cassette to allow for one continuous panoramic electronics package volume 3280. Importantly, different variations of the panoramic digital cassette internals are within the scope of the invention.

(2) The Panoramic Electronic Subsystem.

Generally the electronic subsystem of the panoramic digital cassette corresponds to the electronic system of the digital cassette 200. However, for the reduced active area imaging array system, the time required to collect a pixel value, $T_g$ 2350 is substantially decreased. This allows a much faster frame rate, for much faster access to the sensor array. However, the increased frame rate will also increase the bandwidth requirement of the system. Table 4 illustrates the tradeoffs associated with the desired dimensions of the array system 450 and the number of SVX chips. It also illustrates the maximum frame rate for a set of embodiments.

TABLE 4

| Desired Dimensions | $n_{gate}$ | Max Frame Rate (Hz) | SVX Chips |
| --- | --- | --- | --- |
| 16 × 20 | 3200 | 5 | 32 |
| 20 × 16 | 3840 | 4 | 24 |
| 8 × 10 | 1600 | 9.8 | 16 |
| 10 × 8 | 1920 | 8 | 12 |
| 5 × 12 | 960 | 16 | 18 |
| 12 × 5 | 2240 | 7 | 8 |
| 5 × 0.325 | 960 | 16 | 2 |
| 0.325 × 5 | 320 | 49 | 8 |

In one embodiment, because frames must be merged when a smaller active area is used, it has been found to be beneficial to include different buffering systems. These buffering systems can be used in the digital cassette 200.

No buffer system 3310 shows the imaging array system 450, or the panoramic imaging system 3250, with no buffering. That is, information from the imaging array system 450 is sent directly to the computer 220. Such a no buffer system 3310 requires a very fast communications link 210 and an efficient computer 220. However, the reduced area panoramic digital cassette 3100, with a smaller active imaging area, should capture multiple frames to generate the entire panoramic image. Capturing multiple frames requires significant bandwidth and buffering is a more cost effective solution, in one embodiment.

Table 5 illustrates the bandwidth requirements of a no buffer system 3310. Of course, with compression the maximum megabits per second may be greatly reduced.

TABLE 5

| Desired Dimensions | Bandwidth @ A Min | Bandwidth @ A Max | Bandwidth @ B Min | Bandwidth @ B Max | Total FB RAM |
| --- | --- | --- | --- | --- | --- |
| 16 × 20 | 25.6 kHz (39 μs) | 2 MHz (500 ns) | None | 64 MHz (15 ns) | 6,000 kB |
| 20 × 16 | 61.5 kHz (16 μs) | 2 Mhz (500 ns) | None | 48 MHz (20 ns) | 6,000 kB |
| 8 × 10 | 25.6 kHz (39 μs) | 2 MHz (500 ns) | None | 32 MHz (30 ns) | 3,000 kB |
| 10 × 8 | 30.7 kHz (32 μs) | 2 MHz (500 ns) | None | 24 MHz (40 ns) | 2,880 kB |
| 5 × 12 | 15.4 kHz (65 μs) | 2 MHz (500 ns) | None | 36 MHz (27 ns) | 2,160 kB |
| 12 × 5 | 35.8 kHz (28 μs) | 2 MHz (500 ns) | None | 16 MHz (62 ns) | 1,960 kb |
| 5 × 0.325 | 15.4 kHz (65 μs) | 2 MHz (500 ns) | None | 2 MHz (500 ns) | 120 kB |
| 0.325 × 5 | 5.1 kHz 196 μs) | 2 MHz (500 ns) | None | 16 MHz (62 ns) | 320 kB |

In another embodiment, a single buffer system 3320 is used such as was described for the digital cassette 200. The imaging array system 450, or the panoramic imaging system 3250 communicates the pixel values to the frame buffer 3322. The pixel values can then be stored in the image RAM 3370 or be sent directly to the computer 220. However in one embodiment, because the frame rate is relatively high, a single buffer system 3320 may not be optimal.

Double buffer system 3330 also includes a second a frame RAM 3332. Each SVX chip would be connected to frame buffer chips. The panoramic imaging system 3250 would write to one of the buffered chips while the CPU 2050 processes the previous pixel values stored in the other buffer chip.

Figure 33:
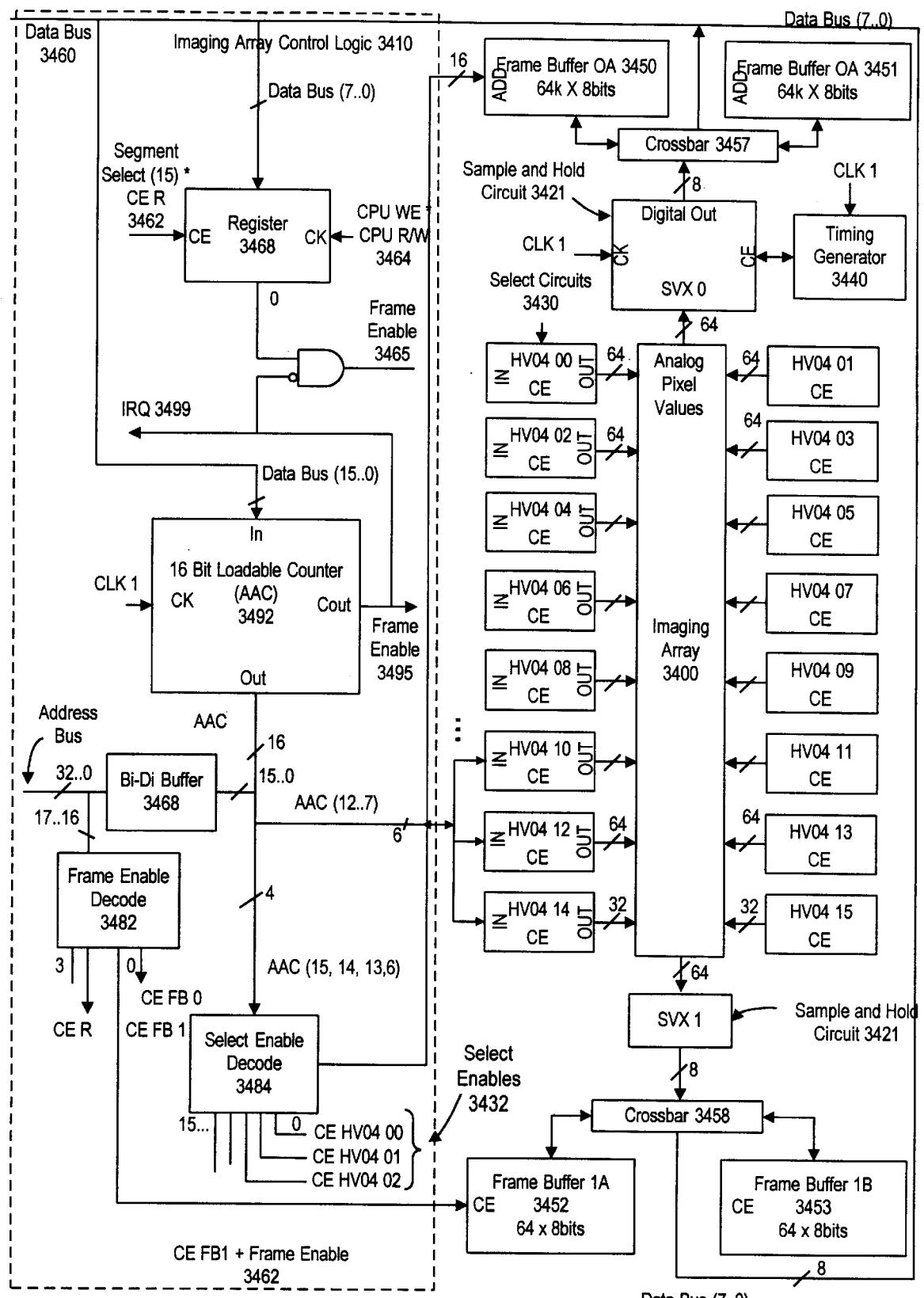
FIG. 33 illustrates an electronic control system for a panoramic digital cassette.

FIG. 33 illustrates an electronic control system for a panoramic digital cassette. The panoramic imaging electronic system includes essentially the same elements as that of the digital cassette electronic system however, the number of components is reduced. This reduces the cost of the electronics system. The electronics system for the reduced area panoramic digital cassette 3100 includes the imaging array 3400. Sixty-four data lines 2120 are output from the top and bottom of the imaging array 3400. individual rows of pixels are selected by the select circuits 3430. Select circuits 3430, include sixteen driver chips in one embodiment. Clock one from the clock generator 2080 is provided as inputs to the sample and hold circuit 3420, the sample and hold circuit 3421, and the timing generator 3440. The 8 bit digital output of the sample and hold circuit 3420 enters the cross bar 3457. The output of the sample and hold circuit 3421 hinders the cross bar 3458. These cross bars selectively couple and decouple the sample and hold circuits from the main data bus. Further, these cross bars select between the first frame buffer or the second frame buffer of the double frame buffer system 3320. Imaging array control logic 3410 includes a 16 bit loadable counter 3492. CPU 2050 can load this counter using the data bus to begin capturing a frame or series of frames. The counter generates the address lines for the frame buffers and the select lines for the drivers in the SVX chips. The addresses from the 16 bit loadable counter 3492 are used by the select enable decode 3484 to generate the select enables 3432. Each of the select enables 3432 enables a single circuit of the select circuits 3430. The bi-Di buffer 3486 optionally allows the address bus to be coupled to the select enable decode 3484. This allows the CPU 2050 to directly address the imaging array 3400 and acquire the pixel value for any pixel. Frame enable decode 3482 selectively enables one side or the other of the frame buffers. For example, the frame enable decode 3482 may enable the frame buffer 0A3450 or 0B34551. Other embodiments of the panoramic digital cassette electronics system can be implemented using different enable and select drivers and sensor components. Some or all of the imaging array control logic 3410 can be implemented in, for example, a gate array or field programmable logic device. Additionally, some or all of the components in the imaging array control logic 3410 can be implemented in the software.

(3) Mechanics of the motion detection

Figure 34:
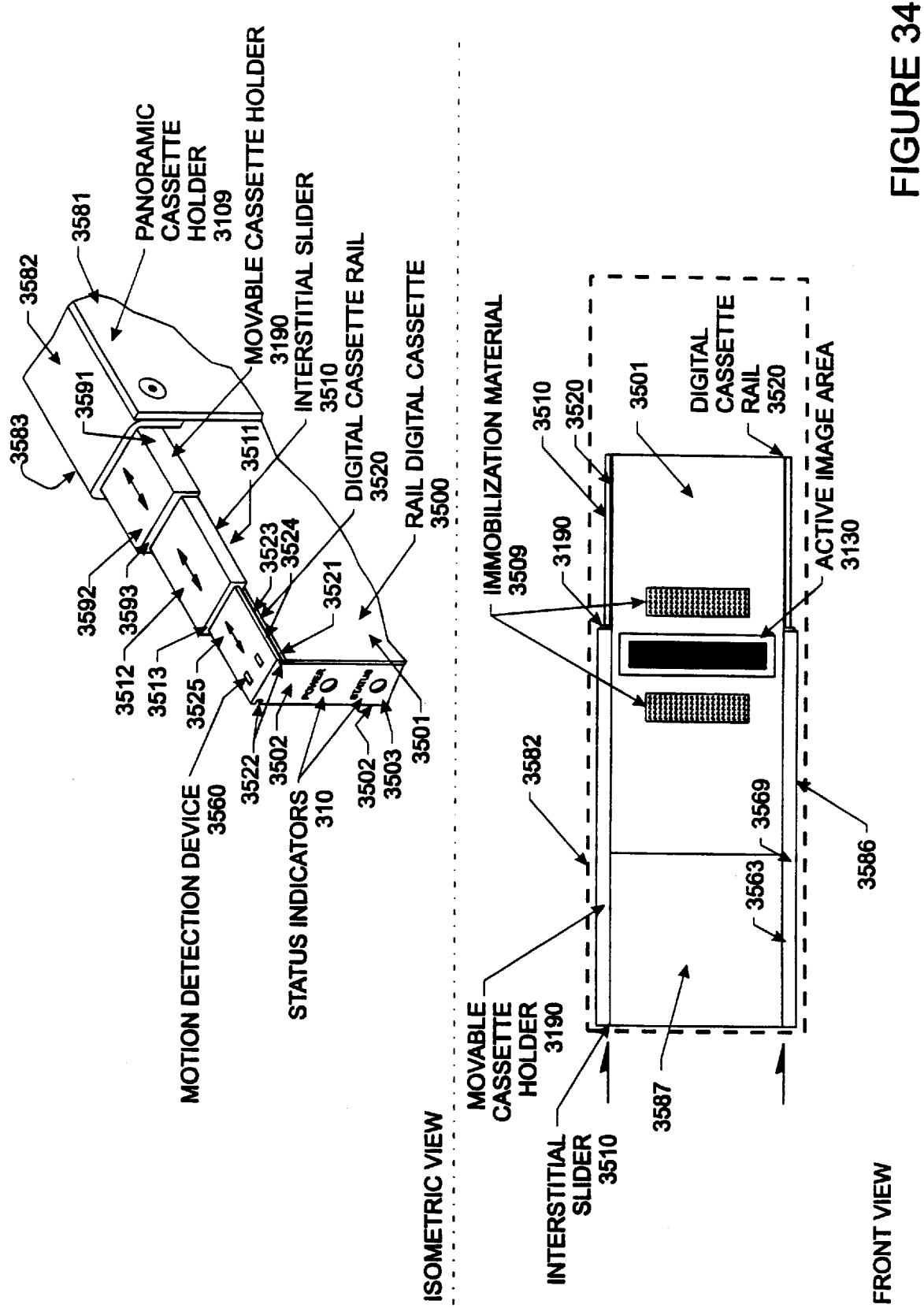
FIG. 34 illustrates a digital panoramic cassette having an interstitial slider.
Figure 36:
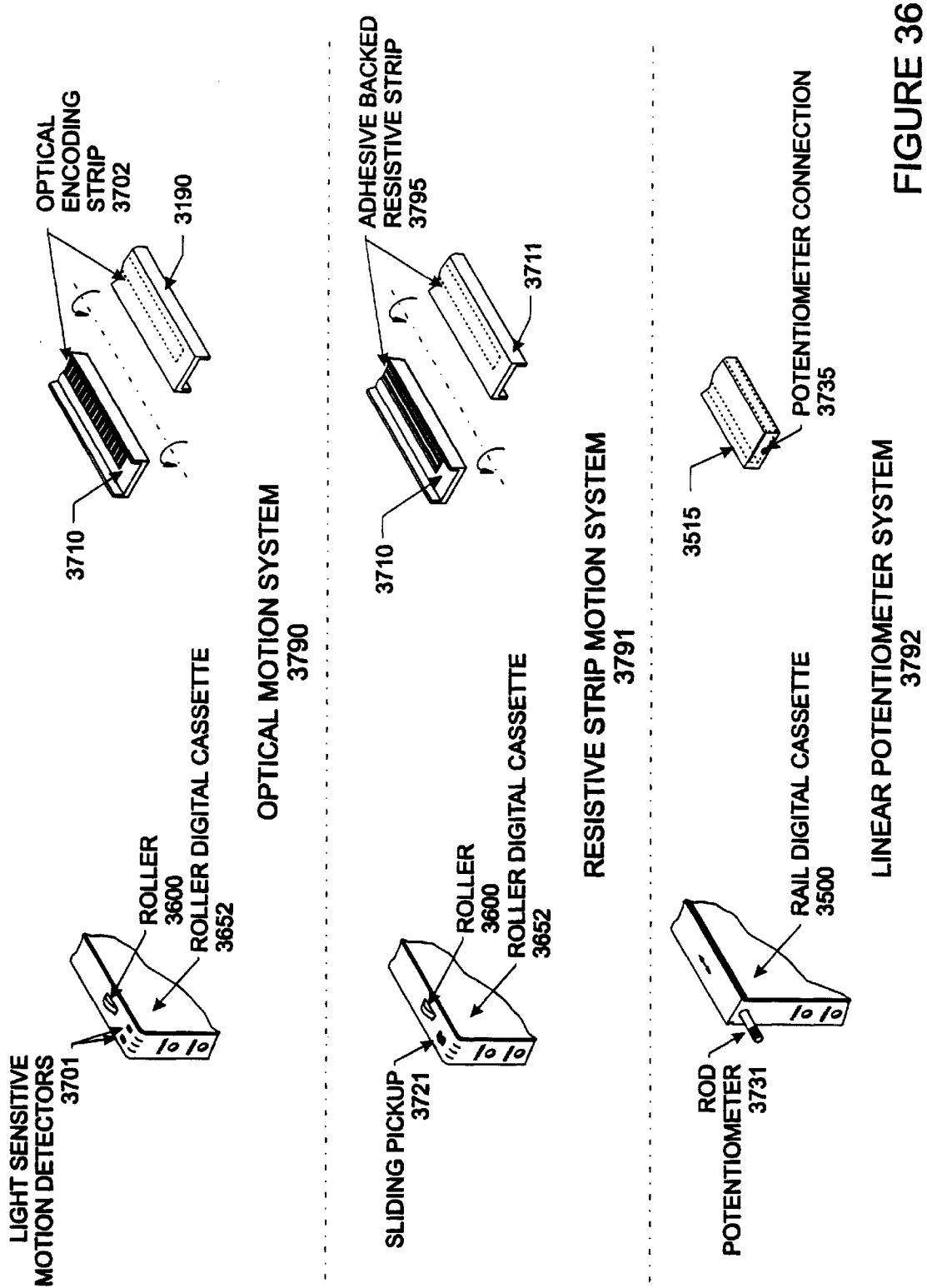
FIG. 36 illustrates a number of motion detection sensing mechanism for a digital panoramic cassette.

FIGS. 34, 35, and 36 illustrate different embodiments of the motion detection mechanical and electrical systems used. These motion detection embodiments allow a smaller active image area to be used to capture panoramic images by merging frames into one image. The merging of the frames is discussed below.

Panoramic cassette holder 3109 includes movable cassette holder 3190. Surface 3592 of movable cassette holder 3190 under surface 3582. The panoramic cassette holder 3109 includes a drive mechanism to cause the movable cassette holder 3190 to move during an x-ray exposure. The panoramic cassette holder 3109 and the movable cassette holder 3190 move a standard film cassette 199 past the aperture 320.

FIG. 34 shows a reduced area panoramic digital cassette 3100 modified to incorporate an interstitial slider into the top and the bottom of the cassette housing, creating a rail digital cassette 3500. The interstitial slider 3510 is designed to engage the movable cassette holder 3190 of the panoramic cassette holder 3109. The main body of the housing is to be fixed relative to the panoramic aperture 320. This can be accomplished by applying an immobilization material to the inside surface of the panoramic cassette holder 3109 and the corresponding surface on the rail digital cassette 3500's housing. During an x-ray exposure, the rail digital cassette 3500's housing will remain stationary while the interstitial sliders will traverse in conjunction with the motion of the panoramic cassette holder 3109's movable cassette holder 3190. Position and velocity will be determined by the electronics system using one of the sensing mechanism described below. Note, in one embodiment, the reduced area panoramic digital cassette 3100's housing and electronics are suitably modified to properly accommodate the function of the rails used in the rail digital cassette 3500.

The rail digital cassette 3500 includes a rail system that immobilizes substantially all of the digital cassette housing and thereby the active image area 3130. The immobilized active image area 3130 is fixed behind the aperture 320. This allows x-rays to continuously be presented onto the active image area 3130. The rail digital cassette 3500 includes a digital cassette rail 3520 and interstitial slider 3510. The movable cassette holder 3190 holds onto the interstitial slider 3510. The movable cassette holder 3190 then only moves the interstitial slider 3510 along the digital cassette rail 3520. Thus, the x-ray machine 101 is not altered to allow for the rail digital cassette 3500 with the active image area 3130. More specifically, the bottom of surface 3592 holds on to the surface 3512 of the interstitial slider 3510. Surface 3511 comes into contact with the bottom of surface 3591. Further, the surface 3513 comes in contact with the bottom of surface 3593. Thus, when the movable cassette holder 3190, as it would to move a standard film cassette 199, only the interstitial slider 3510 moves.

The interstitial slider 3510 moves along the digital cassette rail 3520, is mirrored on the opposite side of the digital cassette rail 3520, is defined by surface 3521, surface 3522, surface 3523, and surface 3524. The bottom of surface of 3512 of the interstitial slider 3510 slides over the surface 3525. Surface 3525 is formed by the edges of the front housing and back housing.

Immobilization material 3509 is affixed to surface 3501 of rail digital cassette 3500. The immobilization material 3509 could be, for example, Velcro or some adhesive material. The immobilization material 3509 prevents the rail digital cassette 3500 active image area 3130 from moving relative to the aperture 320. Of course other methods of immobilizing the main portion of the rail digital cassette 3500 can be employed. For example, brackets, snaps, clips, or other techniques could be used.

Note also that a second interstitial slider is incorporated into the bottom part of the rail digital cassette 3500.

Rail digital cassette 3500 includes motion detection device 3560. These motion detection devices are described in greater detail with regard to FIG. 36. However, importantly, the rail digital cassette 3500 can determine how fast and in which direction the movable cassette holder 3190 is moving during an image exposure. This information can be fed to the electronics system to reconstruct the image from the various captured frames.

FIG. 35 illustrates a roller digital cassette 3562. Roller digital cassette 3652 incorporates a roller 3600 instead of the interstitial slider 3510. A roller is incorporated on both the top and bottom of the main housing of the roller digital cassette 3652. Of course, the external housing may have to be modified slightly to incorporate the roller 3600. In the roller digital cassette 3652 the complexity of the interstitial slider 3510 is removed. Importantly, the main roller digital cassette 3652 housing with the active image area 3130 is immobilized during x-ray exposure. The movable cassette holder 3190 rolls over the roller 3600. That is, surface 3601 of the roller 3600 comes into contact with the bottom of surface 3592.

In one embodiment, roller 3600 is a roller bearing. Again, the immobilization material 3509 immobilizes the main housing. Of course, other immobilization techniques can be employed to prevent the roller digital cassette 3562 from moving during an exposure.

(4) Motion Sensing Mechanisms

Figure 37:
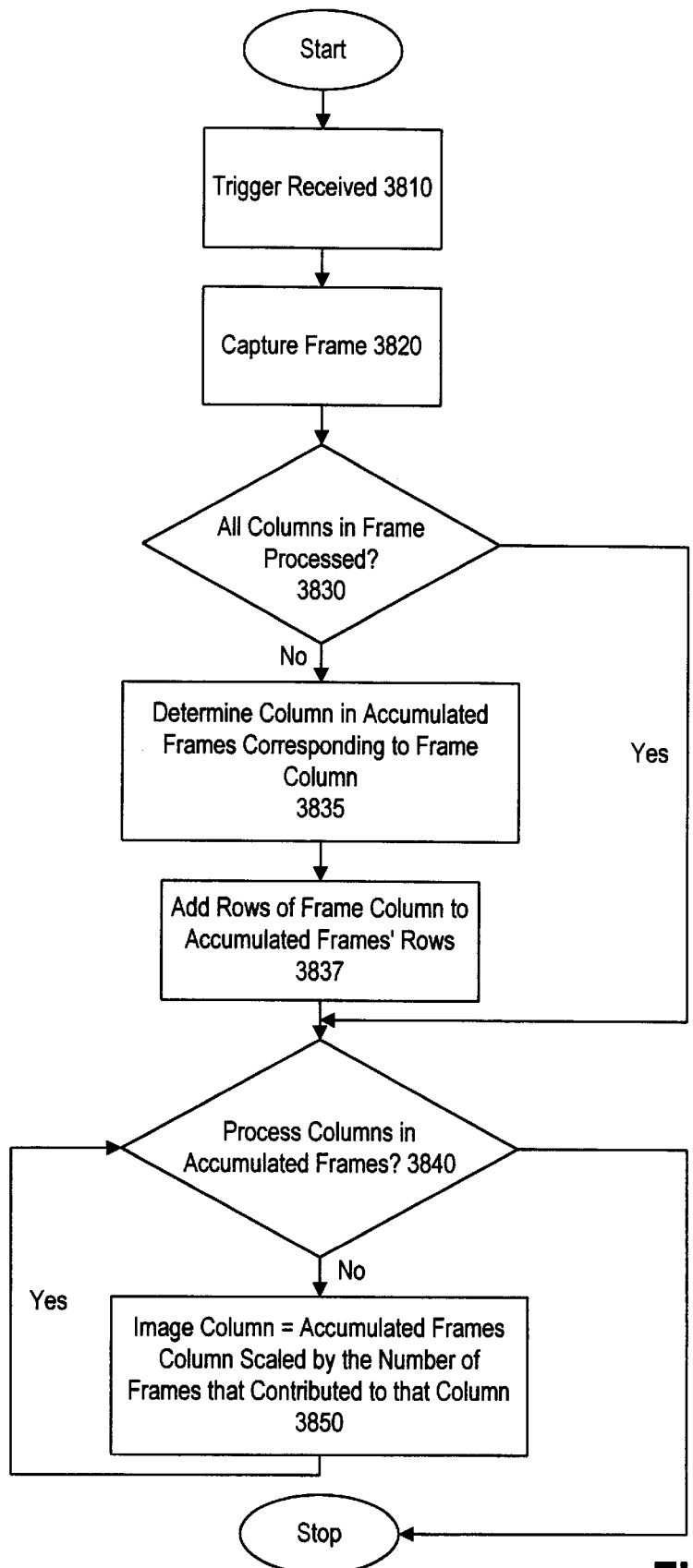
FIG. 37 illustrates an embodiment of a method of merging frames of a digital image to form the digital image.

FIG. 36 illustrates a number of motion detection sensing mechanism for digital panoramic cassette. Different motion sensing methods can be incorporated into the reduced area panoramic digital cassette 3100, rail digital cassette 3500 and the roller digital cassette 3562. In FIG. 37 optical encoding, resistive element sensing, and linear potentiometer sensing are given as examples. However, other methods of motion sensing can be used. For example, radar using one of the new integrated circuits available from Lawrence Livermore Labs of California could be used.

Optical motion system 3790 includes light sensitive motion detectors 3701 on the roller digital cassette 3652. The light sensitive motion detectors 3701 include a light emitting diode, or some other light producing device, and a photo detection diode. The optical encoding strip 3702 is affixed to the movable cassette holder 3190 (or the interstitial slider 3510). In one embodiment, an adhesive backed optical encoding strip 3702 is applied to surface 3710 of the movable cassette holder 3190. In one embodiment, the resolution of the optical encoding system will be equal or better than the resolution of the image array. For example, in one embodiment, if the panoramic imaging system 3250 array detects at 200 spots per inch then the optical motion system 3790 performs at a higher resolution, for example, 400 spots per inch.

In the optical motion system 3790, the movable cassette holder 3190, surface 3710, passes over roller 3600 and over light sensitive motion detectors 3701. The light sensitive motion detectors transmit the motion information to the electronic system. In one embodiment the optical encoding strip is included on both the top and bottom of the roller digital cassette 3652. Thus, position and velocity information of both the optical encoding strips can be correlated for more accuracy.

Resistive strip motion system 3791 includes a sliding pickup 3721 incorporated into the roller digital cassette 3652. In one embodiment, an adhesive backed resistive strip 3795 is attached surface 3710 of the movable cassette holder 3190 or the interstitial slider 3510. The sliding pickup 3721 in contact with the adhesive backed resistive strip 3795 sends information to electronics system providing velocity and position information. This information, can be used to combine the frames captured by the rail digital cassette 3500 or roller digital cassette 3562 into one image.

In another embodiment, a linear potentiometer system 3792 includes a potentiometer rod 3731 in the rail digital cassette 3500. The potentiometer rod 3731 couples to the interstitial slider 3570 via the potentiometer connection 3735. As the interstitial slider 3570 moves with the movable cassette holder 3190, the rail digital cassette 3500 can detect the position of the movable cassette holder 3190 from the position of the potentiometer rod 3731. A linear potentiometer system 3792 could also be employed on the roller digital cassette 3562 if the movable cassette holder 3190 is modified to include a potentiometer connection 3735.

Importantly, as mentioned above, the resolution of these systems should equal or better the resolution of the imaging array.

iv. Software System for Panoramic Digital Cassette

In one embodiment, where the panoramic digital cassette is a digital cassette 200, the core of the software system is essentially the same as that of the digital cassette 200.

In one embodiment, the software system for the reduced area panoramic digital cassette 3100 is similar to the software system for the digital cassette 200, as described in relation to FIG. 25 through FIG. 28. However, in this embodiment, overlapping frames are captured and merged into the final image. FIG. 37 illustrates on embodiment of a method for creating such an image.

At step 3810, the reduced area panoramic digital cassette 3100 receives a trigger to begin capturing an image. In one embodiment, the trigger corresponds to a signal from the motion detection device 3560 indicating that the movable cassette holder 3190 is moving.

At step 3820, a frame is captured. The frame is captured using a block similar to frame capture block 2550.

At step 3830, a test is made to determine whether all the columns in the most recently captured frame have been processed. If not, step 3835 and step 3837 are executed.

At step 3835, the present frame column is correlated with the corresponding column in the accumulated frames.

At step 3837, the rows of the present frame column are added to the corresponding rows in the corresponding accumulated frames.

Once all the columns of the frame have been added to the accumulated frames, then at step 3840, a test is made to determine whether all accumulated frames columns have been processed. If not, then step 3850 is executed.

At step 3850, an image column is generated from a corresponding accumulated frames column. The accumulated frames column is first scaled by the number of frames that contributed to that column.

The following pseudocode illustrates one implementation of the image collection and scaling steps of FIG. 37.

```
/* Collect_Image */
Collect_Image(
    short image[ ],    // collect the image here
    int icols,         // columns in image
    int step,          // step size, number of pixels
    int nstep,         // which step this is, starts at 0
    pix_t frame[ ],    // frame coming in
    int rows,          // rows in frame
    int cols)          // columns in frame
{
    for (int c=0; c < cols; c++)
        {
        short *img_pix = image + icols*(step*nstep+c);
        pix_t *fm_pix = frame + c*cols;
        for(int r = 0; r < rows; r++, img_pix++, fm_pix++)
            *im_pix += *fm_pix;
        }
}
Scale_Image{
    short image[ ],    // collect the image here
    int icols,         // columns in image
    int step,          // step size, number of pixels
    int cols)          // columns in frame
{
    foreach c (column in image)
        {
        int steps_affected = cols / steps;
        int nsteps = 1 + min(c/step, (icols-c)/step);
        if( nstep < steps_affected)
            foreach r (row in c)
                image [r,c,] = image [r,c] *
steps_affected/nstep;
        }
}
```

M. TOMOGRAPHY

Figure 38:
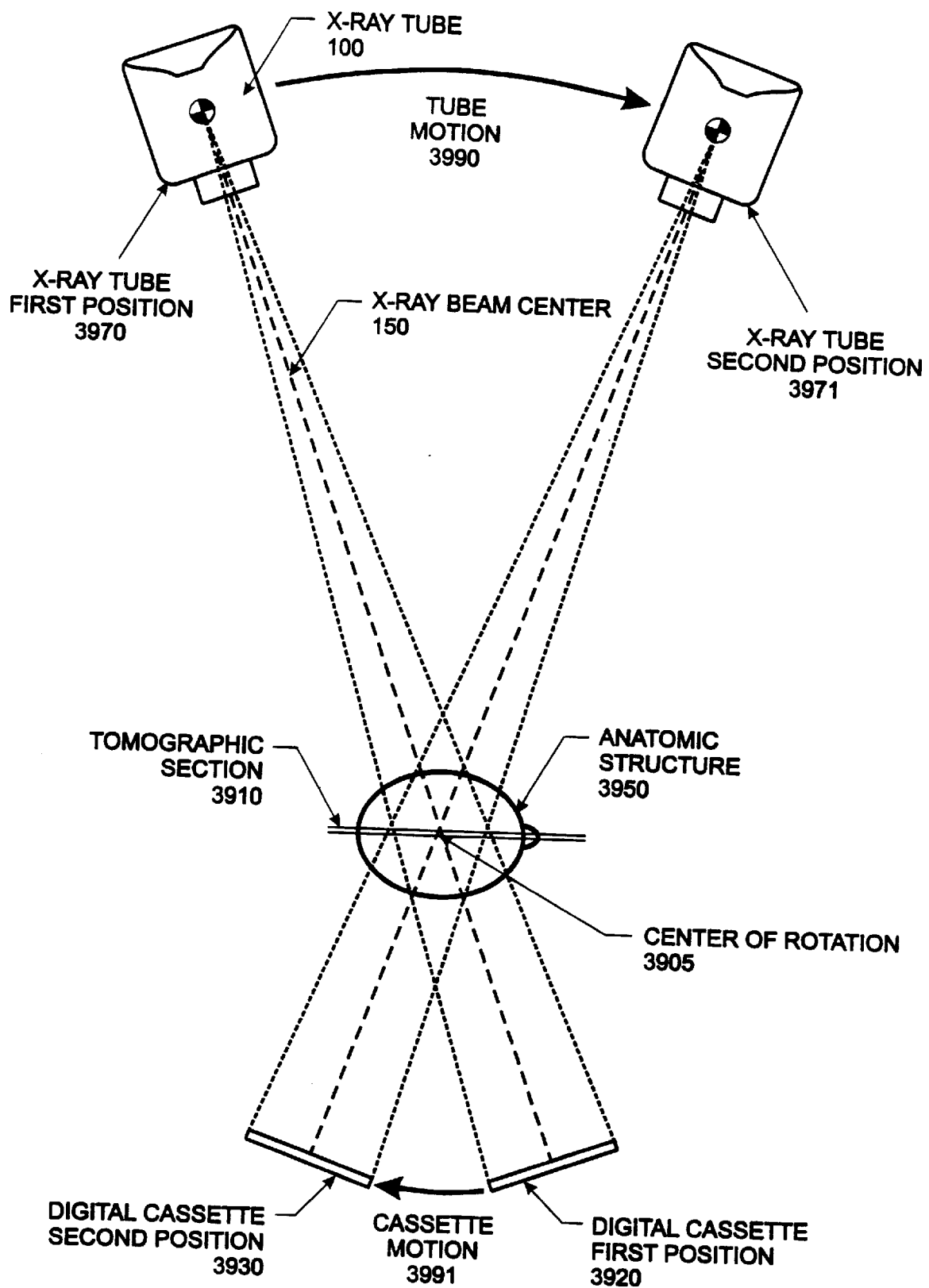
FIG. 38 illustrates the mechanics of taking a tomographic digital x-ray image.

FIG. 38 illustrates the mechanics of taking a tomographic digital x-ray image.

The tomographic principle can be used to create tomographic images that create cross sections of anatomic structures. That is, tomographic techniques produce an image that represents a slice or tomographic section 3910. The tomographic image can be produced by controlled reciprocal movement of the film cassette 199 (including the film) and the x-ray tube 100 during the x-ray exposure. This is shown as tube motion 3990 and cassette motion 3991. The reciprocal movement of the cassette and tube about the sliding center of rotation 3905 create the tomographic section 3910. Parts of the anatomic structure 3950 furthermost away from the center of rotation 3905 are blurred as the x-ray beam center 150 creates the image in the cassette. Therefore, only anatomic structures located near the center of rotation 3905 are clearly displayed on the tomographic images.

The thickness of the tomographic section 3910 are controlled by the motion of the x-ray beam and or the cassette motion 3991.

For film images the film integrates the exposure over time. For the digital cassette, the digital cassette must also integrate the images over time. This can be accomplished in two ways. First the natural storage capabilities of the imaging array system 450 can be used to integrate. Alternatively, frames can be captured and then merged in a technique similar to that described above for the panoramic images. However, the merging of the images is easier for the tomographic features because no pixel offsets need be accounted for.

In one embodiment, the digital cassette 200 begins at digital cassette position 3920 and ends at digital cassette second position 3930. The digital cassette 200 integrates the image over time.

In one embodiment, the tomographic sections 3910 are typically associated with only a small portion of the anatomic structure 3950. That is, only a small area of the tomographic section 3910 is of interest. For example, in some tomographic images the important area around the center of rotation 3905 is approximately only 2"×2". Therefore, in one embodiment, the digital cassette 200 is modified to have a smaller sensor array. In this embodiment, like the panoramic digital cassette, manufacturing costs savings are realized.

In one embodiment, the panoramic digital cassette has an array size that will allow for tomographic images to be taken with the same digital cassette. For example, one embodiment, panoramic digital cassette has an active imaging area of 5"×3".

Such an embodiment, the motion sensitive detector system is disabled for tomographic pictures. This is because the cassette holder 300 does not include a movable cassette holder 3190. Therefore, the digital cassette does not have to compensate for any movement.

What is claimed is:

1. A filmless digital x-ray cassette comprising:
   a standard sized x-ray cassette housing having external dimensions approximately equal to the external dimensions of a standard x-ray cassette;
   an array system having a plurality of light sensitive pixels, said array system being disposed at least partially within said standard sized x-ray cassette housing;
   an electronics system, coupled in communications with said array system, said electronics system converting pixel values received from said array system into a digital image, said electronics system comprising,
      an image capture program for converting said pixel values from said array system into a digital image,
      a cassette id circuit storing information for identifying said filmless digital x-ray cassette,
      an image identification program for using said information to identify said digital image as being captured from said filmless digital x-ray cassette; and
   a communications circuit, coupled to said electronics system, having a digital image output.

2. The filmless digital x-ray cassette of claim 1 wherein said standard sized x-ray cassette housing has a first internal surface and a second internal surface, and wherein said digital x-ray cassette further includes the following elements positioned between said first internal surface and said second internal surface:
   an illuminating screen positioned near said first internal surface and between said first internal surface and said second internal surface, said illuminating screen generating visible light in response to receiving x-ray light;
   said array system being positioned between said illuminating screen and said second internal surface, said array system further being positioned to receive said visible light;
   a second liner positioned between array system and said second internal surface;
   said electronics system at least being partially positioned between said second liner and said second internal surface; and
   wherein said second liner comprises a substance to substantially impede the transmission of x-ray light through to said electronics system.

3. The filmless digital x-ray cassette of claim 1 wherein said image identification program encodes said information into a portion of said digital image.

4. The filmless digital x-ray cassette of said claim 1 wherein said image identification program encodes said information with a portion of said digital image to identify said digital image.

5. The filmless digital x-ray cassette of claim 1 wherein said image identification program uses a public key authentication system to identify said digital image as being captured from said filmless digital x-ray cassette.

6. The filmless digital x-ray cassette of claim 1 wherein said information includes information assigned by an insurance company.

7. The filmless digital x-ray cassette of claim 1 further comprising a compression circuit, said compression circuit for compressing said digital image to reduce the storage and transmission requirements of said digital image.

8. The filmless digital x-ray cassette of claim 7 wherein said compression circuit is a lossless compression circuit.

9. The filmless digital x-ray cassette of claim 7 wherein said compression circuit is a lossy compression circuit.

10. The filmless digital x-ray cassette of claim 7 wherein said electronics system is further for associating capture date, image number, patient identify, and health care provider identity, with said digital image.

11. The filmless digital x-ray cassette of claim 10 wherein said electronics system is further for associating operator identity information with said digital image.

12. A digital x-ray machine comprising:
   an x-ray source;
   an x-ray cassette holder;
   a digital x-ray cassette positioned at least partially within said x-ray cassette holder and positioned to receive x-rays from said x-ray source; and
   an image identification system including a digital x-ray cassette identifier, said image identification system for using said digital x-ray cassette identifier to identify each image captured by said digital x-ray cassette as being captured by said digital x-ray cassette.

13. The digital x-ray machine of claim 12 further comprising a computer system for displaying digital x-ray images from said digital x-ray cassette and wherein said x-ray machine includes an electronics package that allows for wireless communications of said digital x-ray images from said digital cassette to said computer system.

14. The digital x-ray machine of claim 12 wherein said x-ray machine includes a shield defining an aperture for x-rays to pass through before being received at said digital x-ray cassette and wherein said digital x-ray cassette includes a digital sensor and wherein said digital x-ray cassette further includes a means for maintaining said digital sensor positioned to receive said x-rays through said aperture.

15. A direct capture digital x-ray system for capturing digital x-ray images, said system comprising:
   an x-ray machine having a standard sized x-ray cassette holder;
   a direct capture digital x-ray cassette positioned in said x-ray cassette holder;

a computer system coupled to communicate with said direct capture digital x-ray cassette, said computer system coupled to receive digital images from said direct capture digital x-ray cassette; and wherein, images received from said direct capture digital x-ray cassette are associated with an identifier that identifies the digital images as being associated with said direct capture digital x-ray cassette.

16. The direct capture digital x-ray system of claim 15 wherein said computer system associates, with each image received from said digital capture x-ray cassette, tag information, wherein said tag information is used to authenticate said image.

17. The direct capture digital x-ray system of claim 16 wherein said tag information is encoded into a digital signature that is associated with each image.

18. The direct capture digital x-ray system of claim 15 wherein said computer system includes a image receiving stand and wherein said direct capture digital x-ray cassette is adapted to be positioned on said image receiving stand, and wherein said direct capture digital x-ray cassette is for communicating said digital images to said computer system when said direct capture digital x-ray cassette is positioned on said image.

19. The direct capture digital x-ray system of claim 15 wherein said direct capture digital x-ray cassette includes a power source and wherein said image receiving stand includes a recharger for recharging said power source when said direct capture digital x-ray cassette is positioned on said image receiving stand.

* * * * *